(12) United States Patent
Hayoz et al.

(10) Patent No.: US 8,414,982 B2
(45) Date of Patent: Apr. 9, 2013

(54) PROCESS FOR THE PRODUCTION OF STRONGLY ADHERENT COATINGS

(75) Inventors: Pascal Hayoz, Hofstetten (CH); Stephan Ilg, Giebenach (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/792,747

(22) PCT Filed: Dec. 12, 2005

(86) PCT No.: PCT/EP2005/056683
§ 371 (c)(1),
(2), (4) Date: Jun. 12, 2007

(87) PCT Pub. No.: WO2006/067061
PCT Pub. Date: Jun. 29, 2006

(65) Prior Publication Data
US 2009/0092768 A1 Apr. 9, 2009

(30) Foreign Application Priority Data
Dec. 22, 2004 (EP) .................................. 04106822

(51) Int. Cl.
*C08F 4/00* (2006.01)
(52) U.S. Cl.
USPC ............ 427/519; 427/487; 427/496; 427/508
(58) Field of Classification Search .................. 427/519, 427/487, 496, 508
See application file for complete search history.

(56) References Cited

U.S. PATENT DOCUMENTS

| | | | | |
|---|---|---|---|---|
| 6,048,660 | A | 4/2000 | Leppard et al. | 430/270.1 |
| 6,548,121 | B1 | 4/2003 | Bauer et al. | 427/509 |
| 6,838,222 | B2 * | 1/2005 | Aoshima et al. | 430/176 |
| 2005/0147919 | A1 | 7/2005 | Kunz et al. | 430/311 |
| 2006/0073280 | A1 | 4/2006 | Bauer et al. | 427/372.2 |
| 2006/0159856 | A1 | 7/2006 | Kunz et al. | 427/402 |
| 2006/0246291 | A1 | 11/2006 | Kunz et al. | 428/411.1 |
| 2006/0257575 | A1 | 11/2006 | Macor et al. | 427/372.2 |
| 2006/0257681 | A1 | 11/2006 | Wolf et al. | 428/626 |
| 2007/0128441 | A1 | 6/2007 | Macor et al. | 428/411.1 |

FOREIGN PATENT DOCUMENTS

| | | |
|---|---|---|
| DE | 199 53 433 | 5/2001 |
| JP | 2000-126682 | 9/2000 |
| WO | 00/24527 | 5/2000 |
| WO | 03/064061 | 8/2003 |
| WO | WO 03/074718 * | 9/2003 |
| WO | 2004/103580 | 12/2004 |

OTHER PUBLICATIONS

Derwent Abstract No. 2001-466392/51 of DE 199 53 433.
C. Wang et al., J. Polym. Sci. Part A, vol. 31(1993) pp. 1307-1314.
H. Suhr, Plasma Chemistry and Plasma Processing vol. 3, No. 1, 1983 pp. 1-61.
H. Jacobasch et al., Farbe + Lack 99. Jahrgang Jul. 1993, pp. 602-607.
J. Friedrich et al., Surface and Coatings Technology, 59(1993) pp. 371-378.
Machine Translation of JP 2000-126682 (2000)—8 pages.

* cited by examiner

*Primary Examiner* — Robert S Walters, Jr.
(74) *Attorney, Agent, or Firm* — Shruti Costales

(57) ABSTRACT

The invention relates to a process for the production of strongly adherent coatings on an inorganic or organic substrate, wherein in a first step a) a low-temperature plasma, a corona discharge or a flame is caused to act on the inorganic or organic substrate, in a second step b) one or more defined photoinitiators or mixtures of defined photoinitiators with monomers, containing at least one ethylenically unsaturated group, or solutions, suspensions or emulsions of the afore-mentioned substances, are applied, preferably at normal pressure, to the inorganic or organic substrate, in a third step c) using suitable methods those afore-mentioned substances are dried and/or irradiated with electromagnetic waves and, optionally, in a fourth step d) on the substrate so pretreated is applied a further coating.

13 Claims, No Drawings

PROCESS FOR THE PRODUCTION OF STRONGLY ADHERENT COATINGS

The invention relates to a process for the production of strongly adhering coatings on inorganic or organic substrates, wherein a low-temperature plasma treatment, a corona discharge treatment, ozonization, ultra-violet-irradiation or a flame treatment is carried out on the inorganic or organic substrate, one or more photoinitiators are applied at normal pressure to the inorganic or organic substrate, and the substrate so precoated with photoinitiator is coated a final coating, printing ink etc. The invention relates also to novel photoinitiators.

The adhesion properties of coatings (e.g. finishes, paints, release layers, printing inks or adhesives) on inorganic or organic substrates, especially on non-polar substrates such as polyethylene, polypropylene or fluorine-containing polyolefins, are frequently inadequate. For that reason additional treatments have to be carried out in order to achieve satisfactory results. The adhesion can be improved by first applying special priming coatings, so-called primers, and only then applying the desired coating thereto.

A further possibility lies in exposing the substrates to be coated to a plasma treatment or corona treatment and then coating them, it being possible for a grafting process with e.g. acrylate monomers to be carried out between those two operations (J. Polym. Sci., Part A: Polym. Chem. 31, 1307-1314 (1993)).

The production of low-temperature plasmas and the plasma-assisted deposition of thin organic or inorganic layers, both under vacuum conditions and under normal pressure, have been known for some time. Fundamental principles and applications are described, for example, by H. Suhr, Plasma Chem. Plasma Process 3(1), 1, (1983).

It is also known that plastics surfaces can be subjected to a plasma treatment and as a result the subsequently applied finish exhibits improved adhesion to the plastics substrate. This is described by H. J. Jacobasch et al. in Farbe+Lack 99(7), 602-607 (1993) for low-temperature plasmas under vacuum conditions and by J. Friedrich et al. in Surf. Coat. Technol. 59, 371-6 (1993) for plasmas ranging from in vacuo up to normal pressure conditions, the low-temperature plasma changing into a corona discharge.

A process similar to the kind mentioned at the beginning is known from WO 00/24527. That process describes the plasma treatment of substrates with immediate vapour-deposition and grafting-on of photoinitiators in vacuo. A disadvantage, however, is that vapour-deposition requires the use of vacuum apparatus and, because of low deposition rates, is not very efficient and is not suitable for industrial applications having high throughput rates. A similar process is disclosed in WO 03/064061.

There is a need in the art for processes for the pretreatment of substrates that can readily be carried out in practice and are not too expensive in terms of apparatus by means of which the subsequent coating of those substrates is improved.

It has now been found that coatings having especially good adhesion can be obtained by applying a specific photoinitiator to a substrate to be coated, after that substrate has been subjected to a plasma treatment (low pressure and/or normal pressure plasmas), corona treatment or flame treatment, optionally drying, and irradiating the substrate so treated. The resulting coatings exhibit surprisingly good adhesion.

The invention therefore relates to a process for the production of a strongly adherent coating on an inorganic or organic substrate, wherein a) a low-temperature plasma treatment, a corona discharge treatment, ozonization or ultraviolet irradiation or a flame treatment is carried out on the inorganic or organic substrate, b) one or more photoinitiators or mixtures of photoinitiators with monomers or/and oligomers, containing at least one ethylenically unsaturated group, or solutions, suspensions or emulsions of the afore-mentioned substances, are applied to the inorganic or organic substrate, and c) using suitable methods those afore-mentioned substances are optionally dried and/or are irradiated with electromagnetic waves, characterized in that in step b) is used at least one photoinitiator of the formula I or Ia,

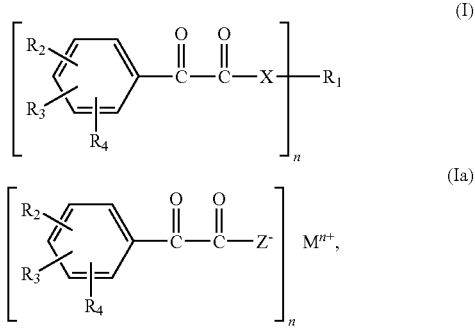

wherein n is a number from 1 to 4;

X is O, S or $NR_5$;

z is O or S;

$R_1$, when n is 1, is hydrogen, $C_1$-$C_{50}$alkyl, $C_2$-$C_{24}$alkenyl, $C_3$-$C_{25}$cycloalkyl; $C_2$-$C_{250}$alkyl interrupted by one or more $X_2$; $C_2$-$C_{24}$alkenyl interrupted by one or more $X_2$; $C_3$-$C_{25}$cycloalkyl interrupted by one or more $X_2$;

wherein said radicals $C_1$-$C_{50}$alkyl, $C_2$-$C_{24}$alkenyl, $C_3$-$C_{25}$cycloalkyl; $C_2$-$C_{250}$alkyl interrupted by one or more $X_2$; $C_2$-$C_{24}$alkenyl interrupted by one or more $X_2$; $C_3$-$C_{25}$cycloalkyl interrupted by one or more $X_2$; optionally are substituted by one or more A;

or $R_1$ is phenyl, optionally substituted by $A_1$;

or, when X is $NR_5$, $R_5$ and $R_1$ together with the N-atom may form a ring, besides the N-atom optionally comprising another group $NR_5$;

$R_1$, when n is 2, is a divalent linking group;

$R_1$, when n is 3, is a trivalent linking group;

$R_1$, when n is 4, is a tetravalent linking group;

M is an n-valent cation;

A is

$OR_9$, $SR_9$, $NR_{10}R_{11}$, halogen, unsubstituted phenyl, or phenyl substituted by one or more $C_1$-$C_{24}$alkyl, $C_3$-$C_{25}$cycloalkyl, $C_2$-$C_{24}$alkenyl, $C_2$-$C_{24}$alkinyl, phenyl, $OR_9$, $SR_9$, $COR_9$, $COOR_9$, $OCOR_9$, $CONR_{10}R_{11}$, $OCONR_{10}R_{11}$,

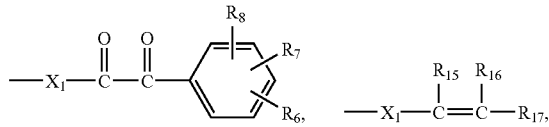 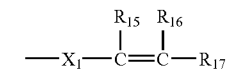

and/or

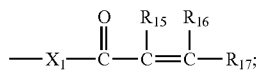

$A_1$ is $C_1$-$C_{24}$alkyl, $C_2$-$C_{24}$alkyl interrupted by one or more $X_2$; $C_2$-$C_{24}$alkenyl, $C_2$-$C_{24}$alkenyl interrupted by one or more $X_2$; $C_3$-$C_{25}$cycloalkyl; $C_3$-$C_{25}$cycloalkyl interrupted by one or more $X_2$; wherein said radicals $C_1$-$C_{24}$alkyl, $C_2$-$C_{24}$alkyl interrupted by one or more $X_2$, $C_2$-$C_{24}$alkenyl; $C_2$-$C_{24}$alkenyl interrupted by one or more $X_2$; $C_3$-$C_{25}$cycloalkyl; and $C_3$-$C_{25}$cycloalkyl interrupted by one or more $X_2$; optionally are substituted by one or more $C_2$-$C_{24}$alkinyl, phenyl, $OR_9$, $SR_9$, —$COR_9$, $COOR_9$,

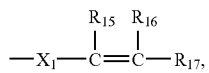

and/or

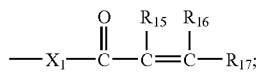

or $A_1$ is

$OR_9$, $SR_9$, $NR_{10}R_{11}$, unsubstituted phenyl, or phenyl substituted by one or more $C_1$-$C_{24}$alkyl, $C_2$-$C_{24}$alkenyl, $C_3$-$C_{25}$cycloalkyl, $C_2$-$C_{24}$alkinyl, phenyl, $OR_9$, $SR_9$, $COR_9$, $COOR_9$, $OCOR_9$, $CON_{10}R_{11}$, $OCONR_{10}R_{11}$,

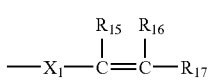

and/or

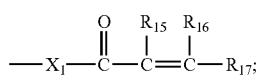

$R_2$, $R_3$ and $R_4$ independently of one another are hydrogen, halogen, CN, $C_1$-$C_{24}$alkyl, $C_2$-$C_{24}$alkyl interrupted by one or more $X_2$; $C_2$-$C_{24}$alkenyl, $C_2$-$C_{24}$alkenyl interrupted by one or more $X_2$; $C_3$-$C_{25}$cycloalkyl; $C_3$-$C_{25}$cycloalkyl interrupted by one or more $X_2$; wherein said radicals $C_1$-$C_{24}$alkyl, $C_2$-$C_{24}$alkyl interrupted by one or more $X_2$, $C_2$-$C_{24}$alkenyl, $C_2$-$C_{24}$alkenyl interrupted by one or more $X_2$, $C_3$-$C_{25}$cycloalkyl, and $C_3$-$C_{25}$cycloalkyl interrupted by one or more $X_2$; optionally are substituted by one or more $C_2$-$C_{24}$alkinyl, phenyl, halogen, $OR_9$, $SR_9$, $NR_{10}R_{11}$, $COR_9$, $COOR_9$, $OCOR_9$, $N(R_5)COR_9$, $CON(R_5)R_9$,

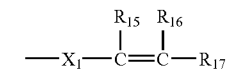

and/or

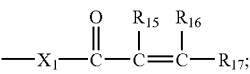

or $R_2$, $R_3$ and $R_4$ are

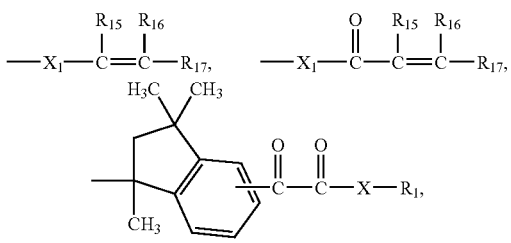

$OR_9$, $SR_9$, $NR_{10}R_{11}$, $COR_9$, $COOR_9$, $OCOR_9$, $N(R_5)COR_9$, $CON(R_5)R_9$, unsubstituted phenyl, or phenyl substituted by one or more $OR_9$, $SR_9$, $NR_{10}R_{11}$, $COR_9$, $COOR_9$, $OCOR_9$, $N(R_5)COR_9$, $CONR_{10}R_{11}$, $OCONR_{10}R_{11}$, $C_1$-$C_{24}$alkyl, $C_2$-$C_{24}$alkenyl, $C_3$-$C_{25}$cycloalkyl, $C_2$-$C_{24}$alkinyl, phenyl,

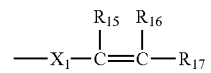

and/or

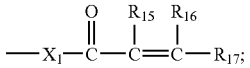

or $R_2$ and $R_3$ together form $C_1$-$C_6$alkylene or $R_2$ and $R_3$ together form a benzene ring that is condensed to the phenyl ring to which they are attached;

$R_5$ has one of the meanings as given for $R_1$, when n is 1; or $R_5$ is

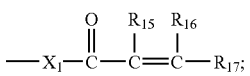

$X_1$ is a direct bond, O, S or $NR_{12}$;

$X_2$ is O, S, $NR_{12}$, CO, COO, OCO, $CONR_{12}$, $NR_{12}CO$, $OCONR_{12}$, $NR_{12}COO$, $NR_{12}CONR_{13}$, SO, $SO_2$, $CR_{12}=CR_{13}$, C≡C, N=C—$R_{12}$, $R_{12}C=N$,

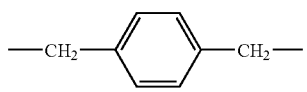

phenylene;

or phenylene substituted by $A_1$;

$R_6$, $R_7$ and $R_8$ independently of one another have the same meanings as given for $R_2$, $R_3$ and $R_4$;

$R_9$, $R_{10}$ and $R_{11}$ independently of one another are hydrogen, $C_1$-$C_{24}$alkyl; $C_2$-$C_{24}$alkyl interrupted by one or more $X_2$; $C_2$-$C_{24}$alkenyl; $C_2$-$C_{24}$alkenyl interrupted by one or more $X_2$; $C_3$-$C_{25}$cycloalkyl; $C_3$-$C_{25}$cycloalkyl interrupted by one or more $X_2$; wherein said radicals $C_1$-$C_{24}$alkyl; $C_2$-$C_{24}$alkyl interrupted by one or more $X_2$; $C_2$-$C_{24}$alkenyl; $C_2$-$C_{24}$alkenyl interrupted by one or more $X_2$; $C_3$-$C_{25}$cycloalkyl; and $C_3$-$C_{25}$cycloalkyl interrupted by one or more $X_2$; optionally are substituted by one or more $C_2$-$C_{24}$alkinyl, phenyl, halogen, CN, $OR_{12}$, $SR_{12}$, $COR_{12}$, $COOR_{12}$,

and/or

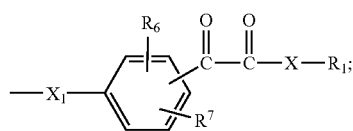

or $R_9$, $R_{10}$ and $R_{11}$ independently of one another are unsubstituted phenyl or phenyl substituted by one or more $COR_{12}$, $COOR_{12}$, $OCOR_{12}$, $CONR_{13}R_{14}$, $OCONR_{13}R_{14}$, $C_1$-$C_{2-4}$alkyl, $C_2$-$C_{24}$alkenyl, $C_3$-$C_{25}$cycloalkyl, $C_2$-$C_{24}$alkinyl, phenyl, $OR_{12}$, $SR_{12}$,

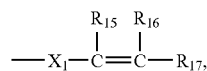

and/or

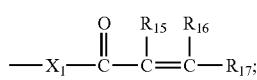

or $R_9$, $R_{10}$ and $R_{11}$ independently of one another are unsubstituted phenyl-$C_1$-$C_4$-alkyl or phenyl-$C_1$-$C_4$alkyl substituted by one or more $COR_{12}$, $COOR_{12}$, $OCOR_{12}$, $CONR_{13}R_{14}$, $OCONR_{13}R_{14}$, $C_1$-$C_{24}$alkyl, $C_3$-$C_{25}$cycloalkyl, $C_2$-$C_{24}$alkenyl, $C_2$-$C_{24}$alkinyl, phenyl, $OR_{12}$, $SR_{12}$,

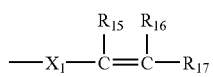

and/or

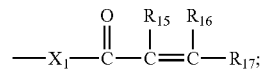

$R_{12}$, $R_{13}$ and $R_{14}$ independently of one another are hydrogen, phenyl, $C_1$-$C_{24}$alkyl; $C_2$-$C_{24}$alkyl, interrupted by one or more $X_3$; $C_2$-$C_{24}$alkenyl; $C_2$-$C_{24}$alkenyl interrupted by one or more $X_3$; $C_3$-$C_{25}$cycloalkyl; $C_3$-$C_{25}$cycloalkyl interrupted by one or more $X_3$; wherein said radicals phenyl, $C_1$-$C_{24}$alkyl; $C_2$-$C_{24}$alkyl, interrupted by one or more $X_3$; $C_2$-$C_{24}$alkenyl; $C_2$-$C_{24}$alkenyl interrupted by one or more $X_3$; $C_3$-$C_{25}$cycloalkyl; and $C_3$-$C_{25}$cycloalkyl interrupted by one or more $X_3$ optionally are substituted by one or more OH or halogen;

$X_3$ is O, S or $NR_5$; and $R_{15}$, $R_{16}$ and $R_{17}$ independently of one another are hydrogen, $C_1$-$C_{24}$alkyl, $CH_2$—COOH, COOH, or phenyl.

The invention further pertains to a process as described above, wherein d) a further coating, e.g. an ink, a laquer or a metallayer or an adhesion layer or release layer, is applied and dried or cured.

The process is simple to carry out and allows a high throughput per unit of time.

In the process according to the invention, after the photoinitator or photoinitiators, or a solution or dispersion thereof in a solvent or monomer, has or have been applied to the substrate which has been plasma-, corona-, ozonization-, ultra-violet-or flame-pretreated and after any drying step for evaporating off any solvent used, a fixing step for the photoinitiator is carried out by exposure to UV/VIS light. In the context of the present Application, the term "drying" includes both variants, both the removal of the solvent and the fixing of the photoinitiator.

In step c) of the above-described preferred process, the drying, that is to say the removal of the solvent, is optional. That step can be omitted, for example, when no solvent was used.

The fixing of the photoinitiator in step c) by irradiation with electromagnetic waves, especially UV/VIS radiation, must be carried out.

Process step b) in the above-described process is preferably carried out under normal pressure.

If, in process step b), mixtures of photoinitiators with monomers or/and oligomers are used, the use of mixtures of one or more photoinitiators with one or more monomers is preferred.

Possible ways of obtaining plasmas under vacuum conditions have been described frequently in the literature. The electrical energy can be coupled in by inductive or capacitive means. It may be direct current or alternating current; the frequency of the alternating current may range from a few kHz up into the MHz range. A power supply in the microwave range (GHz) is also possible.

The principles of plasma production and maintenance are described, for example, in the review article by H. Suhr mentioned above.

As primary plasma gases it is possible to use, for example, He, argon, xenon, $N_2$, $O_2$, $H_2$, $CO_2$, steam or air.

The process according to the invention is not sensitive per se in respect of the coupling-in of the electrical energy.

The process can be carried out batchwise, for example in a rotating drum, or continuously in the case of films, fibres or woven fabrics. Such methods are known and are described in the prior art.

The process can also be carried out under corona discharge conditions. Corona discharges are produced under normal pressure conditions, the ionised gas used being most frequently air. In principle, however, other gases and mixtures are also possible, as described, for example, in COATING Vol. 2001, No. 12, 426, (2001). The advantage of air as ionisation gas in corona discharges is that the operation can be carried out in an apparatus open to the outside and, for example, a film can be drawn through continuously between the discharge electrodes. Such process arrangements are known and are described, for example, in J. Adhesion Sci. Technol. Vol 7, No. 10, 1105, (1993). Three-dimensional workpieces can be treated with a plasma jet, the contours, for example, being followed with the assistance of robots.

The flame treatment of substrates is known to the person skilled in the art. Corresponding industrial apparatus, for example for the flame treatment of films, is commercially available. In such a treatment, a film is conveyed on a cooled cylindrical roller past the flame-treatment apparatus, which consists of a chain of burners arranged in parallel, usually along the entire length of the cylindrical roller. Details can be found in the brochures of the manufacturers of flame-treatment apparatus (e.g. esse Cl, flame treaters, Italy). The parameters to be chosen are governed by the particular substrate to be treated. For example, the flame temperatures, the flame intensity, the dwell times, the distance between substrate and burner, the nature of the combustion gas, air pressure, humidity, are matched to the substrate in question. As flame gases it is possible to use, for example, methane, propane, butane or a mixture of 70% butane and 30% propane.

The ozonization procedure is known to the person skilled in the art and for example described in Ullmans Encyclopedia of Industrial Research, Wiley-VCH Verlag GmbH 2002, chapter "Ozone"; or by R. N. Jagtap, Popular Plastics and Packaging, August 2004.

Ultra-violet irradiation is carried out as described below for step c) or d).

In the process according to the invention in step a) a plasma, corona-or flame treatment is preferred. In particular preferred in step a) is a corona treatment.

The inorganic or organic substrate to be treated can be in any solid form. The substrate is preferably in the form of a woven fabric, a fibre, a film or a three-dimensional workpiece. The substrate may be, for example, a thermoplastic, elastomeric, inherently crosslinked or cross-linked polymer, a metal, a metal oxide, a ceramic material, glass, leather or textile.

The pretreatment of the substrate in the form of plasma-, corona-or flame-treatment can, for example, be carried out immediately after the extrusion of a fibre or film, and also directly after film-drawing.

The substrate may already be pretreated by corona, plasma or flame by the provider. Advantageously, such substrates are again treated by corona plasma or flame before applying the formulation according to step b) of the process according to the invention. That is, irrespective of the a previous treatment of the substrate, e.g. by the provider, all steps a)-c), or a)-d), respectively, of the process according to the invention are carried out.

The inorganic or organic substrate is preferably a thermoplastic, elastomeric, inherently crosslinked or crosslinked polymer, a ceramic material or a glass, or metal, especially a thermoplastic, elastomeric, inherently crosslinked or crosslinked polymer.

Examples of thermoplastic, elastomeric, inherently crosslinked or crosslinked polymers are listed below.

1. Polymers of mono-and di-olefins, for example polypropylene, for example bisaxial oriented polypropylene (BOPP), polyisobutylene, polybutene-1, poly-4-methylpentene-1, polyisoprene or polybutadiene and also polymerisates of cyclo-olefins, for example of cyclopentene or norbornene; and also polyethylene (which may optionally be crosslinked), for example high density polyethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE).

Polyolefins, that is to say polymers of mono-olefins, as mentioned by way of example in the preceding paragraph, especially polyethylene and polypropylene, can be prepared by various processes, especially by the following methods:
a) by free radical polymerisation (usually at high pressure and high temperature);
b) by means of a catalyst, the catalyst usually containing one or more metals of group IVb, Vb, VIb or VII. Those metals generally have one or more ligands, such as oxides, halides, alcoholates, esters, ethers, amines, alkyls, alkenyls and/or aryls, which may be either π-or σ-coordinated. Such metal complexes may be free or fixed to carriers, for example to activated magnesium chloride, titanium(III) chloride, aluminium oxide or silicon oxide. Such catalysts may be soluble or insoluble in the polymerisation medium. The catalysts can be active as such in the polymerisation or further activators may be used, for example metal alkyls, metal hydrides, metal alkyl halides, metal alkyl oxides or metal alkyl oxanes, the metals being elements of group(s) Ia, IIa and/or IIIa. The activators may have been modified, for example, with further ester, ether, amine or silyl ether groups. Such catalyst systems are usually referred to as Phillips, Standard Oil Indiana, Ziegler (-Natta), TNZ (DuPont), metallocene or Single Site Catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono-and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and copolymers thereof with carbon monoxide, or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another or with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, for example polyamides.

4. Hydrocarbon resins (for example $C_5$-$C_9$) including hydrogenated modifications thereof (for example tackifier resins) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate and methacrylate, styrene/maleic anhydride, styrene/acrylonitrile/methyl acrylate; high-impact-strength mixtures consisting of styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.

7. Graft copolymers of styrene or $\alpha$-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), such as those known, for example, as so-called ABS, MBS, ASA or AES polymers.

8. Halogen-containing polymers, for example polychloroprene, chlorinated rubber, chlorinated and brominated copolymer of isobutylene/isoprene (halobutyl rubber), chlorinated or chlorosulfonated polyethylene, copolymers of ethylene and chlorinated ethylene, epichlorohydrin homo-and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from $\alpha,\beta$-unsaturated acids and derivatives thereof, such as polyacrylates and polymethacrylates, or polymethyl methacrylates, polyacrylamides and polyacrylonitriles impact-resistant-modified with butyl acrylate.

10. Copolymers of the monomers mentioned under 9) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, polyvinylbutyral, polyallyl phthalate, polyallylmelamine; and the copolymers thereof with olefins mentioned in Point 1.

12. Homo-and co-polymers of cyclic ethers, such as polyalkylene glycols, polyethylene oxide, polypropylene oxide or copolymers thereof with bisglycidyl ethers.

13. Polyacetals, such as polyoxymethylene, and also those polyoxymethylenes which contain comonomers, for example ethylene oxide; polyacetals modified with thermoplastic polyurethanes, acrylates or MBS.

14. Polyphenylene oxides and sulfides and mixtures thereof with styrene polymers or polyamides.

15. Polyurethanes derived from polyethers, polyesters and polybutadienes having terminal hydroxyl groups on the one hand and aliphatic or aromatic polyisocyanates on the other hand, and their initial products.

16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides derived from m-xylene, diamine and adipic acid; polyamides prepared from hexamethylenediamine and iso-and/or tere-phthalic acid and optionally an elastomer as modifier, for example poly-2,4,4-trimethylhexamethylene terephthalamide or poly-m-phenylene isophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS; and polyamides condensed during processing ("RIM polyamide systems").

17. Polyureas, polyimides, polyamide imides, polyether imides, polyester imides, polyhydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and also block polyether esters derived from polyethers with hydroxyl terminal groups; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol-formaldehyde, urea-formaldehyde and melamine-formaldehyde resins.

22. Drying and non-drying alkyd resins.

23. Unsaturated polyester resins derived from copolyesters of saturated and unsaturated dicarboxylic acids with polyhydric alcohols, and also vinyl compounds as crosslinking agents, and also the halogen-containing, difficultly combustible modifications thereof.

24. Crosslinkable acrylic resins derived from substituted acrylic esters, e.g. from epoxy acrylates, urethane acrylates or polyester acrylates.

25. Alkyd resins, polyester resins and acrylate resins that are crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of bisphenol-A diglycidyl ethers, bisphenol-F diglycidyl ethers, that are crosslinked using customary hardeners, e.g. anhydrides or amines with or without accelerators.

27. Natural polymers, such as cellulose, natural rubber, gelatin, or polymer-homologously chemically modified derivatives thereof, such as cellulose acetates, propionates and butyrates, and the cellulose ethers, such as methyl cellulose; and also colophonium resins and derivatives.

28. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The substrate can be a pure compound or a mixture of compounds containing at least one component as listed above.

The substrate can also be a multilayer construction containing at least one of the components listed above obtained e.g. by coextrusion, coating, lamination, sputtering etc.

The substrate can be the top layer or the bulk material of a three dimensional article.

The substrate can optionally be chemically or physically pretreated prior to the process steps of the invention.

The substrate can be e.g. a plastic part like e.g. a bumper, body part or other work piece from e.g. a car, truck, ship, aircraft, machine housing etc. or the substrate can for example be a plastic part from the inside or outside of a building. These examples restrict by no means other applications of the described process.

The substrate can for example be one as used in the commercial printing area, sheet-fed- or web-printing, posters, calendars, forms, labels, wrapping foils, tapes, credit cards, furniture profiles, etc. The substrate is not restricted to the use in the non-food area. The substrate may also be, for example, a material for use in the field of nutrition, e.g. as packaging for foodstuffs; cosmetics, medicaments, etc.

Where substrates have been pretreated according to processes of the invention it is also possible, for example, for substrates that usually have poor compatibility with one another to be adhesively bonded to one another or laminated.

The substrates are preferably labels and films, e.g. published in catalogues or in the internet by producers like DOW, ExxonMobil, Avery, UCB, BASF, Innovia, Klocke Gruppe, Raflatac, Treofan etc.

Within the context of the present invention, paper should also be understood as being an inherently crosslinked polymer, especially in the form of cardboard, which can additionally be coated with e.g. Teflon®. Such substrates are, for example, commercially available.

The thermoplastic, crosslinked or inherently crosslinked plastics is preferably a polyolefin, polyamide, polyacrylate, polycarbonate, polyester, polystyrene or an acrylic/melamine, alkyd or polyurethane surface-coating.

Polycarbonate, polyester, polyethylene and polypropylene are especially preferred as pure compounds or as main compounds of multilayer systems.

The plastics may be, for example, in the form of films, injection-moulded articles, extruded workpieces, fibres, felts or woven fabrics.

As inorganic substrates there come into consideration especially glass, ceramic materials, metal oxides and metals. They may be silicates and semi-metal or metal oxide glasses which are preferably in the form of layers or in the form of powders preferably having average particle diameters of from 10 nm to 2000 µm. The particles may be dense or porous. Examples of oxides and silicates are $SiO_2$, $TiO_2$, $ZrO_2$, MgO, NiO, $WO_3$, $Al_2O_3$, $La_2O_3$, silica gels, clays and zeolites. Preferred inorganic substrates, in addition to metals, are silica gels, aluminium oxide, titanium oxide and glass and mixtures thereof.

As metal substrates there come into consideration especially Fe, Al, Ti, Ni, Mo, Cr and steel alloys.

Photoinitiators suitable for use in the process according to the invention are of the formula I or Ia, as defined above. Said photoinitiators of the formula I or Ia are in particular suitable and mandatory in step b).

The meanings of the substituents defined in formulae I and Ia in the different radicals are explained below.

$C_1$-$C_{50}$alkyl is linear or branched and is, for example, $C_1$-$C_{24}$, $C_1$-$C_{18}$—, $C_1$-$C_{14}$-, $C_1$-$C_{12}$-, $C_1$-$C_8$-, $C_1$-$C_6$-or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl, icosyl, pentadecyl.

$C_1$-$C_{24}$alkyl, $C_1$-$C_{18}$alkyl, $C_1$-$C_{14}$alkyl, $C_1$-$C_{12}$alkyl, $C_1$-$C_8$alkyl, $C_1$-$C_6$alkyl and $C_1$-$C_4$alkyl have the same meanings as given above for $C_1$-$C_{50}$alkyl up to the corresponding number of C-atoms.

$C_2$-$C_{250}$alkyl interrupted by one or more $X_2$, that is by O, S, $NR_{12}$, CO, COO, OCO, $CONR_{12}$, $NR_{12}CO$, $OCONR_{12}$, $NR_{12}COO$, $NR_9COR_{10}$, SO, $SO_2$, $CR_{12}$=$CR_{13}$, C≡C, N=C—$R_{12}$, $R_{12}$C=N, phenylene; and/or phenylene substituted by $A_1$, for example, interrupted 1-125 times, for example 1-120, 1-100, 1-80, 1-60, 1-50, 1-30, 1-20, 1-15, 1-12, 1-7 times or once or twice. The alkyl is linear or branched. This produces structural units such as, for example, —$CH_2$—O—$CH_2$—,

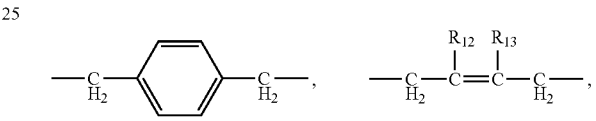

—$CH_2$—S—$CH_2$—, —$CH_2$—N($CH_3$)—$CH_2$—, —$CH_2CH_2$—O—$CH_2CH_2$—, —[$CH_2CH_2O$]$_y$, —[$CH_2CH_2O$]$_y$—$CH_2$—, where y=1-60, —($CH_2CH_2O$)$_7$ $CH_2CH_2$—, —$CH_2$—CH($CH_3$)—O—$CH_2$—CH($CH_3$)— or —$CH_2$—CH($CH_3$)—O—$CH_2$—$CH_2CH_2$—. Interrupting O-atoms are nonsuccessive. If $X_2$ is O the structural units for interrupted alkyl may also be derived from conventional polyethyleneglycols or polypropyleneglycols, or polytetrahydrofurane of diversified chain lengths. Preferred are such structures to be derived from commercially available polyethyleneglycols, polypropyleneglycols, and polytetrahydrofurane, with for example, MW up to 35000 for polyethyleneglycols, MW up to 35000 for polypropyleneglycols, and MW up to 50000 for polytetrahydrofurane.

Interrupted $C_2$-$C_{250}$alkyl is for example $C_2$-$C_{200}$-, $C_2$-$C_{180}$-, $C_2$-$C_{150}$-, $C_2$-$C_{125}$-, $C_2$-$C_{100}$-, $C_2$-$C_{80}$-, $C_2$-$C_{50}$-, $C_2$-$C_{24}$alkyl. $C_2$-$C_{200}$-, $C_2$-$C_{180}$-, $C_2$-$C_{150}$-, $C_2$-$C_{125}$-, $C_2$-$C_{100}$-, $C_2$-$C_{80}$-, $C_2$-$C_{50}$-, $C_2$-$C_{24}$alkyl interrupted by one or more $X_2$ have the same meanings as given for $C_2$-$C_{250}$alkyl interrupted by one or more $X_2$ up to the corresponding number of C-atoms.

Similar meanings apply for $C_2$-$C_{24}$alkyl interrupted by $X_3$.

If any of the definitions combined with one another lead to consecutive O-atoms, these should be considered excluded in the compounds of formula I and Ia in the context of the present application.

$C_2$-$C_{24}$alkenyl radicals are mono or polyunsaturated, linear or branched and are for example $C_2$-$C_{12}$-, $C_2$-$C_{10}$-, $C_2$-$C_8$-, $C_2$-$C_6$-or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_2$-$C_{24}$alkenyl interrupted by one or more $X_2$ produces similar units as described for interrupted alkyl, wherein one or more alkylene units will be replaced by unsaturated units, that is, the interrupted alkenyl is mono-or polyunsaturated and linear or branched.

Similar meanings apply for $C_2$-$C_{24}$alkenyl interrupted by $X_3$.

$C_3$-$C_{25}$Cycloalkyl is for example $C_4$-$C_{12}$-, $C_5$-$C_{10}$cycloalkyl. Examples are cyclopropyl, cyclopentyl, cyclohexyl, cyclooctyl, cyclo-dodecyl, especially cyclopentyl and cyclohexyl, preferably cyclohexyl. $C_3$-$C_{25}$cycloalkyl in the context of the present application is to be also understood as alkyl which at least comprises one ring. For example methyl-cyclopentyl, methyl-or dimethylcyclohexyl,

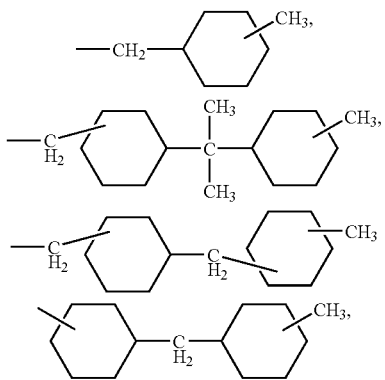

as well as bridged or fused ring systems, e.g.

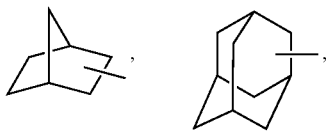

etc. are also meant to be covered by the term.

$C_2$-$C_{24}$alkinyl radicals are mono or polyunsaturated, linear or branched and are for example $C_2$-$C_8$-, $C_2$-$C_6$— or $C_2$-$C_4$alkinyl. Examples are ethinyl, propinyl, butinyl, 1-butinyl, 3-butinyl, 2-butinyl, pentinyl hexinyl, 2-hexinyl, 5-hexinyl, octinyl, etc.

Phenyl-$C_1$-$C_4$-alkyl is for example benzyl, phenylethyl, α-methylbenzyl, phenylbutyl, or α,α-dimethylbenzyl, especially benzyl.

Substituted phenyl is substituted one to four times, for example once, twice or three times, especially once. The substituents are for example in 2-, 3-, 4-, 2,4-, 2,6-, 2,3-, 2,5-, 2,4,6-, 2,3,4-, 2,3,5-position of the phenyl ring.

When X is $NR_5$, $R_5$ and $R_1$ together with the N-atom may form a ring, besides the N-atom optionally comprising another group $NR_5$ for example the following structures are formed

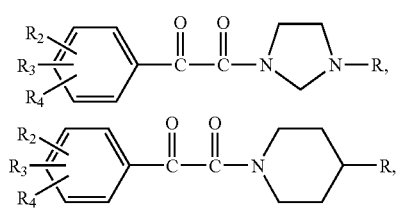

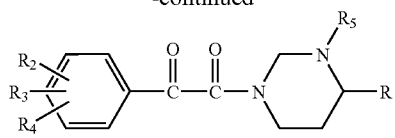

etc., wherein R is for example a group A as defined above, $R_2$, $R_3$, $R_4$ are as defined above. If n is 2, for example bridging structures as

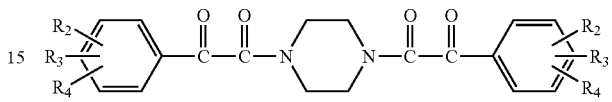

described by the above definition.

If $R_2$ and $R_3$ together form $C_1$-$C_6$alkylene or $R_2$ and $R_3$ together form a benzene ring that is condensed to the phenyl ring to which they are attached, for example structures of the following kind are encompassed

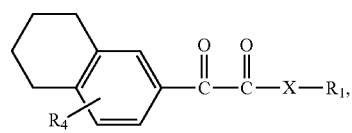

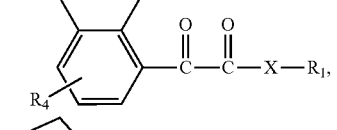

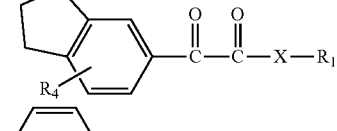

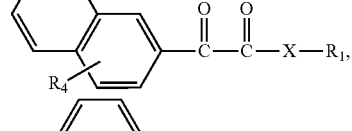

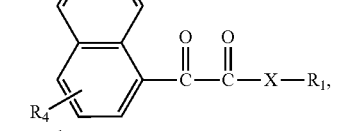

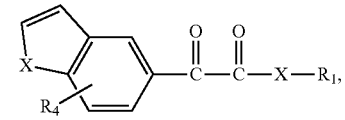

where $R_4$, X and $R_1$ are as defined above.

Halogen is fluorine, chlorine, bromine and iodine, especially fluorine, chlorine and bromine, preferably fluorine and chlorine.

If alkyl is substituted one or more times by halogen, then there are for example 1 to 3 or 1 or 2 halogen substituents on the alkyl radical.

M as an n-valent cation is for example $M_1$, a monovalent cation, $M_2$, a divalent cation, $M_3$, a trivalent cation or $M_4$, a tetravalent cation.

M is for example a metal cation in the oxidation state +1, such as $Li^+$, $Na^+$, $K^+$, $Cs^+$, an "onium" cation, such as ammonium-, phosphonium-, iodonium- or sulfonium cation, a metal cation in the oxidation state +2, such as $Mg^{2+}$, $Ca^{2+}$, $Zn^{2+}$, $Cu^{2+}$, a metal cation in the oxidation state +3, such as $Al^{3+}$, a metal cation in the oxidation state +4, such as $Sn^{4+}$ or $Ti^{4+}$. Examples for onium cations are ammonium, tetra-alkylammonium, tri-alkyl-aryl-ammonium, di-alkyl-di-aryl-ammonium, tri-aryl-alkyl-ammonium, tetra-aryl-ammonium, tetra-alkylphosphonium, tri-alkyl-aryl-phosphonium, di-alkyl-di-aryl-phosphonium, tri-aryl-alkyl-phosphonium, tetra-aryl-phosphonium. E.g. $N^+R_{18}R_{19}R_{20}R_{21}$ or $P^+R_{18}R_{19}R_{20}R_{21}$, wherein $R_{18}$, $R_{19}$, $R_{20}$, $R_2$, independently of one another are hydrogen, $C_1$-$C_{20}$alkyl, phenyl; $C_1$-$C_{20}$alkyl substituted by OH or phenyl; phenyl substituted by OH or $C_1$-$C_4$ alkyl.

$M_1$ is for example, a metal cation in the oxidation state +1, $N^+R_{18}R_{19}R_{20}R_{21}$ or $P^+R_{18}R_{19}R_{20}R_{21}$, wherein $R_{18}$, $R_{19}$, $R_{20}$, $R_2$, independently of one another are hydrogen, $C_1$-$C_{20}$alkyl, phenyl; $C_1$-$C_{20}$alkyl substituted by OH or phenyl; phenyl substituted by OH or $C_1$-$C_4$ alkyl.

$M_1$ is preferably $Li^+$, $Na^+$, $K^+$, $Cs^+$, $N^+R_{18}R_{19}R_{20}R_{21}$ or $P^+R_{18}R_{19}R_{20}R_{21}$; in particular $Li^+$, $Na^+$, $K^+$, $N^+R_{18}R_{19}R_{20}R_{21}$ or $P^+R_{18}R_{19}R_{20}R_{21}$.

$M_2$ is for example a metal cation in the oxidation state +2; such as for example $Mg^{2+}$, $Ca^{2+}$, $Zn^{2+}$, $M_2$ is preferably $Mg^{2+}$ or $Ca^{2+}$.

$M_3$ is a metal cation in the oxidation state +3; such as for example $Al^{3+}$;

$M_4$ is a metal cation in the oxidation state +4; such as for example $Sn^{4+}$ or $Ti^{4+}$.

The above-given examples for the definitions of the radicals are considered illustrative and non-limiting in view of the claimed scope.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

$R_1$ when n is 2, as a divalent linking group, for example is $C_1$-$C_{50}$alkylene; $C_2$-$C_{50}$alkylene interrupted by $X_2$; $C_2$-$C_{50}$alkenylene; $C_2$-$C_{50}$alkenylene interrupted by $X_2$; $C_4$-$C_{25}$cycloalkylene; $C_3$-$C_{25}$cycloalkylene interrupted by $X_2$; phenylene, biphenylene, wherein said $C_1$-$C_{50}$alkylene; $C_2$-$C_{50}$alkylene interrupted by $X_2$; $C_2$-$C_{50}$alkenylene; $C_2$-$C_{50}$alkenylene interrupted by $X_2$; $C_4$-$C_{25}$cycloalkylene; $C_3$-$C_{25}$cycloalkylene interrupted by $X_2$; phenylene and biphenylene optionally are substituted by one or more $A_2$; or $R_1$, when n is 2 is Z, CO-Z-CO,

[chemical structure]

[chemical structure]

or $R_1$, when n is 2 and X is $NR_5$, together with $R_5$ forms an aliphatic ring comprising the two N-atoms as heteroatoms;

x is an integer from 0 to 3, preferably 0 or 1, in particular 0;

Z is $C_2$-$C_{250}$alkylene; $C_2$-$C_{250}$alkylene interrupted by 0; wherein both $C_2$-$C_{250}$alkylene and $C_2$-$C_{250}$alkylene interrupted by 0 optionally are substituted by $A_2$;

$Z_1$ and $Z_2$ independently of each other are hydrogen or $C_1$-$C_{20}$alkyl, preferably H or $C_1$-$C_4$alkyl, in particular H or methyl;

$A_2$ is $OR_9$, $SR_9$, $NR_{10}R_{11}$, $COOR_9$, $COR_9$, $OCOR_9$, $CONR_{10}R_{11}$, $OCONR_{10}R_{11}$, CN, halogen, $C_5$-$C_{12}$cycloalkyl, phenyl, phenyl-$C_1$-$C_4$alkyl; phenyl substituted by $C_1$-$C_{12}$alkyl, halogen, CN, $OR_{12}$, $SR_{12}$ or $NR_{13}R_{14}$; or $A_2$ is

[chemical structure]

and/or

[chemical structure]

$X_2$ has one of the meanings as given above;

$R_1'$ has one of the meanings given for $R_1$, when n is 1; and $X_1'$ has one of the meanings given for $X_1$ above.

$R_1$ when n is 3, as a trivalent linking group for example is an alkanetriyl, optionally substituted, e.g. with OH, such as for example

[chemical structures]

etc.; $R_1$ when n is 4, as a tetravalent linking group for example is an alkanetetrayl, such as for example

[chemical structure]

etc.

$C_1$-$C_{50}$alkylene, means $C_1$-$C_{50}$alkanediyl, e.g. $C_1$-$C_{25}$-, $C_1$-$C_{12}$-, $C_1$-$C_8$-, $C_1$-$C_4$alkylene. Said alkylene is linear or branched. Examples are methylene, ethylene, propylene, isopropylene, butylene, pentylene, hexylene, heptylene, 2,4,4-trimethylpentylene, 2-ethylhexylene, octylene, nonylene, decylene, dodecylene, tetradecylene, pentadecylene, hexadecylene, octadecylene, icosylene, pentadecylene. $C_1$-$C_{25}$-, $C_1$-$C_{12}$-, $C_1$-$C_8$-, $C_1$-$C_4$alkylene have the same meanings as given above for $C_1$-$C_{50}$alkylene up to the corresponding number of C-atoms.

$C_3$-$C_{25}$Cycloalkylene ($C_3$-$C_{25}$Cycloalkyldiyl) is for example $C_4$-$C_{25}$-, $C_4$-$C_{12}$-, $C_5$-$C_{10}$cycloalkylene. Examples are cyclopropylene, cyclopentylene, cyclohexylene, cyclooctylene, cyclo-dodecylene, especially cyclopentylene and cyclohexylene, preferably cyclohexylen. $C_3$-$C_{25}$cycloalkylene in the context of the present application is to be also understood as alkylene (alkanediyl) which at least comprises one ring. For example methylcyclopentylene, methyl-or dimethylcyclohexylene,

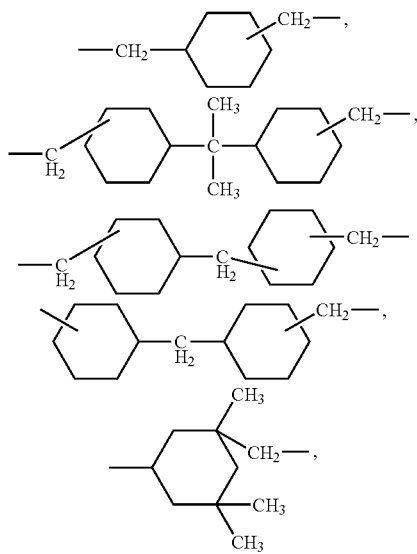

as well as bridged or fused ring systems, e.g.

etc. are also meant to be covered by the term.

The meanings of the other radicals are as described above.

n preferably is 1 or 2.

Preferred groups $R_1$ are substituted with A.

$R_1$ in particular is $C_2$-$C_{50}$alkyl, for example $C_2$-$C_{24}$— or $C_2$-$C_{12}$alkyl, interrupted by $X_2$, in particular by O.

A is for example $OR_9$, $NR_{19}R_{11}$ or

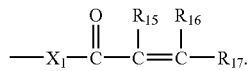

Preferably A is an acrylic group

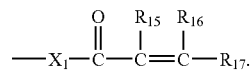

If one of $R_2$, $R_3$ and $R_4$ is other than hydrogen, the radical is for example in the 4-or 3-or 2-position of the phenyl ring, preferably in the 4-or 2-position, in particular in the 4-position, of the phenyl ring. If two of $R_2$, $R_3$ and $R_4$ are other than hydrogen, the radicals are for example in the 3,4-, 2,4-, 2,6-, preferably in the 3,4-or 2,4-, in particular in the 3,4-position of the phenyl ring. If $R_2$, $R_3$ and $R_4$ all are other than hydrogen the radicals are for example in the 3,4,5-, 2,4,6-or 2,3,4-position, in particular in the 2,4,6-or 3,4,5-position, of the phenyl ring.

$R_2$, $R_3$ and $R_4$ independently of one another are for example hydrogen, $OR_9$, $SR_9$, $NR_{10}R_{11}$ or

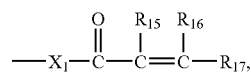

preferably $OR_9$.

The same definitions as given for $R_2$, $R_3$ and $R_4$ apply for $R_6$, $R_7$ and $R_8$.

$X_1$ is for example a direct bond, O or $NR_{12}$, preferably a direct bond or O.

$X_2$ is for example O, $NR_{12}$ or S, preferably O.

$R_5$ is for example hydrogen, $C_1$-$C_{50}$-, $C_1$-$C_{12}$-or $C_1$-$C_4$alkyl or together with $R_1$ and together with the N-atom forms a ring, besides the N-atom optionally comprising another group $NR_5$; preferably said ring comprises 6 atoms and is e.g.

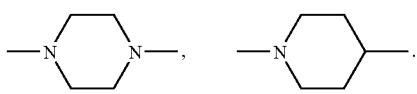

In particular $R_5$ is hydrogen or together with $R_1$ and with the N-atom forms a ring.

$R_9$ is for example hydrogen, $C_1$-$C_{24}$-, $C_1$-$C_{12}$-or $C_1$-$C_4$alkyl or $C_2$-$C_{12}$alkenyl or is a group

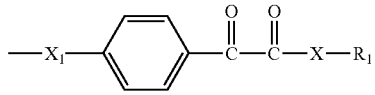

or $R_9$ is phenyl-$C_1$-$C_4$alkyl, in particular benzyl, substituted by

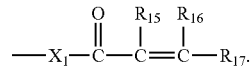

If $R_9$ is phenyl-$C_1$-$C_4$alkyl, in particular benzyl, substituted by

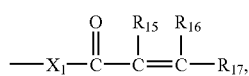

$X_1$ preferably is a direct bond.

$R_{10}$ and $R_{11}$ independently of one another are for example hydrogen, $C_1$-$C_{12}$-or $C_1$-$C_4$alkyl, preferably hydrogen or methyl.

$R_{15}$, $R_{16}$ and $R_{17}$ are for example $C_1$-$C_{12}$alkyl or hydrogen, in particular $C_1$-$C_4$alkyl, for example methyl, or hydrogen.

Interesting as photoinitiators in step b) of the process according to the invention in particular are compounds of the formula I or Ia, wherein
n is a number 1 or 2;
X is O or $NR_5$;
z is O;
$R_1$, when n is 1, is hydrogen, $C_1$-$C_{50}$alkyl, $C_2$-$C_{50}$alkyl interrupted by one or more $X_2$; $C_2$-$C_{24}$alkenyl, $C_2$-$C_{24}$alkenyl interrupted by one or more $X_2$;
wherein said radicals $C_1$-$C_{50}$alkyl, $C_2$-$C_{50}$alkyl interrupted by one or more $X_2$, $C_2$-$C_{24}$alkenyl and $C_2$-$C_{24}$alkenyl interrupted by one or more $X_2$ optionally are substituted by one or more A;
or, when X is $NR_5$, $R_5$ and $R_1$ together with the N-atom may form a ring, besides the N-atom optionally comprising another group $NR_5$;
$R_1$ when n is 2, as a divalent linking group is $C_1$-$C_{50}$alkylene or $C_2$-$C_{250}$alkylene interrupted by $X_2$; or $R_1$, when n is 2 and X is $NR_5$, together with $R_5$ forms an aliphatic ring comprising the two N-atoms as heteroatoms;
M is an n-valent cation;
A is

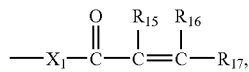

$OR_9$, or $NR_{10}R_{11}$;
$R_2$, $R_3$ and $R_4$ independently of one another are hydrogen, $C_1$-$C_{24}$alkyl, $OR_9$, $SR_9$, or $NR_{10}R_{11}$;
$R_5$ has one of the meanings as given for $R_1$, when n is 1; or $R_5$ is

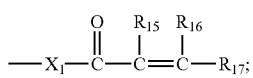

$X_1$ is a direct bond or O;
$X_2$ is O;
$R_6$ and $R_7$ have one of the meanings given for $R_2$, $R_3$ and $R_4$;
$R_9$, $R_{10}$ and $R_{11}$ independently of one another are hydrogen, $C_1$-$C_{24}$alkyl, $C_2$-$C_{24}$alkenyl; $C_2$-$C_{24}$alkenyl substituted by

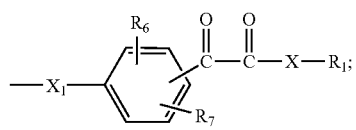

or $R_9$, $R_{10}$ and $R_{11}$ independently of one another are unsubstituted phenyl-$C_1$-$C_4$-alkyl; or phenyl-$C_1$-$C_4$-alkyl substituted by

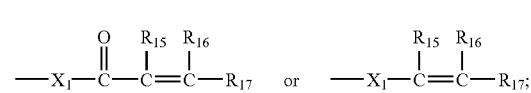

and
$R_{15}$, $R_{16}$ and $R_{17}$ independently of one another are hydrogen or $C_1$-$C_{24}$alkyl.

Preferred in the process of the invention are compounds of the formula I.

In one embodiment of the process according to the present invention oxo-phenyl-acetic acid 1-methyl-2-[2-(2-oxo-2-phenyl-acetoxy)-propoxy]-ethyl ester is not used in step b) of said process.

I. The compounds of the formula I can be prepared, for example, by reacting alcohols, thiols or amines e.g. diols (A) with arylglyoxalic monoesters (B), such as for example the corresponding methyl or ethyl ester, for example, in the presence of a catalyst:

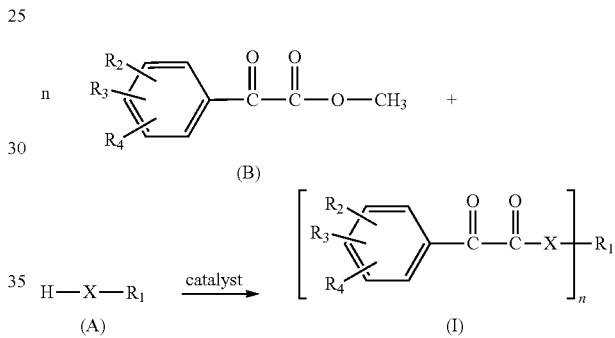

$R_1$, $R_2$, $R_3$, $R_4$, X and n are as defined above.

The catalyst used is one of the catalysts familiar to the skilled worker for such reactions, enzymes, heterogenous or homogenous catalysts, for example e.g. basic catalysts, such as for example sodium methylate, acid catalysts, such as for example p-toluenesulfonic acid, metal complexes, such as for example dibutyltin oxide etc.

II. A further possibility to obtain the compounds of the formula I is the (optionally base-catalysed) reaction of arylglyoxalic halides (C), preferably the chlorides, with an alcohol, thiol or amine, e.g. a diol (A):

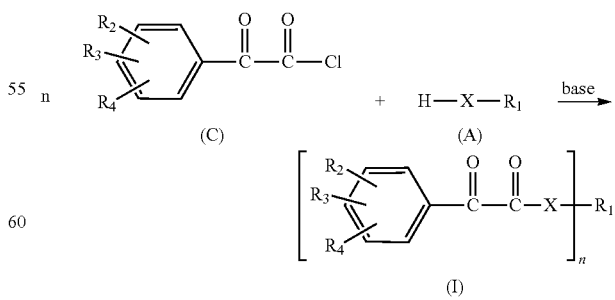

$R_1$, $R_2$, $R_3$, $R_4$, X and n are as defined above.

The bases to be used for such reactions are familiar to the skilled worker. Aqueous bases should not be employed.

Examples of suitable bases are carbonates, tertiary amine bases, such as triethylamine, or pyridine, for example.

III. It is also possible to obtain the compounds of the formula I, for example, by reacting alcohols, thiols or amines (A) with corresponding arylacetic esters (D) in the presence of a catalyst and with subsequent oxidation:

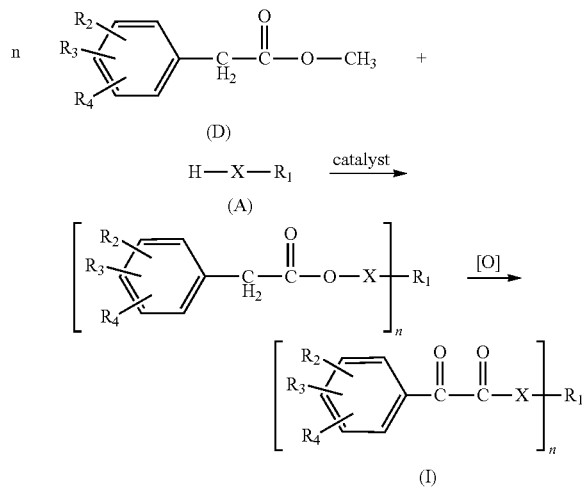

$R_1$, $R_2$, $R_3$, $R_4$, X and n are as defined above.

Examples of catalysts which can be employed are those described under I.

The oxidation step can take place, for example, as described in *J. Chem. Soc. Chem. Comm.* (1993), 323 or in *Synthesis* (1994), 915.

IV. A further suitable preparation method for the compounds of the formula I is, for example, the reaction of corresponding hydroxy-substituted arylacetic esters (E) with alcohols, thiols or amines (A) and with subsequent oxidation:

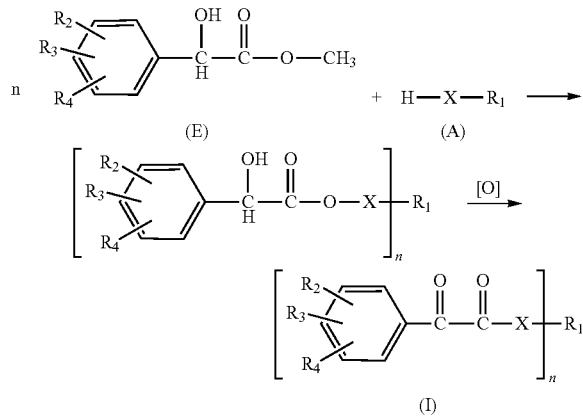

$R_1$, $R_2$, $R_3$, $R_4$, X and n are as defined above.

The oxidation can be carried out, for example, by the method described in *J. Chem. Soc. Chem. Comm.* (1994), 1807.

V. A further preparation option for the compounds of the formula I is the acid-catalysed reaction of arylcarboxylic cyanides (F) with alcohols, thiols or amines (A):

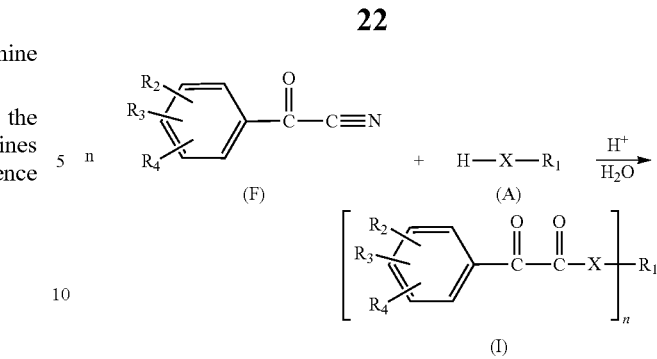

$R_1$, $R_2$, $R_3$, $R_4$, X and n are as defined above.

VI. The compounds of the formula I can also be obtained, for example, by Friedel-Crafts reaction of aryls with corresponding oxocarboxylic chlorides (H) in the presence of a Friedel Crafts catalyst, e.g. aluminium chloride:

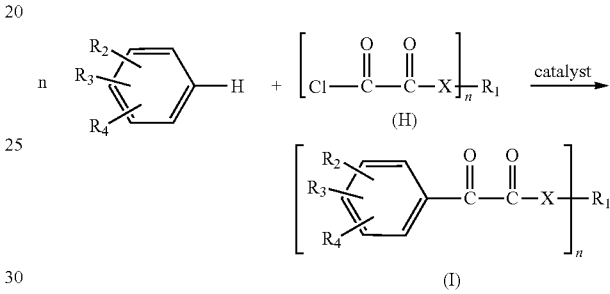

$R_1$, $R_2$, $R_3$, $R_4$, X and n are as defined above.

Catalysts which can be used are the catalysts which are familiar to the skilled worker and are customary for Friedel-Crafts reactions, examples being tin chloride, zinc chloride, aluminium chloride, titanium chloride or acid earths.

VII. The compounds of the formula I can be prepared, for example, by reacting alcohols, thiols or amines e.g. diols (A) with arylglyoxalic acids (J), for example, in the presence of a catalyst:

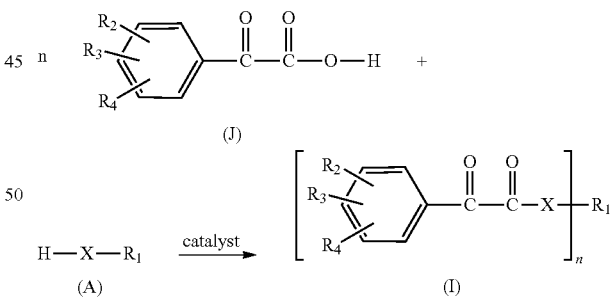

$R_1$, $R_2$, $R_3$, $R_4$, X and n are as defined above. X is preferably O.

The catalyst used is one of the catalysts familiar to the skilled worker for esterification reactions, enzymes, heterogenous or homogenous catalysts, for example ion exchange resins, acids, such as for example methanesulfonic acid, p-toluenesulfonic acid, sulphuric acid, hydrochloric acid etc. See e.g. examples 10 and 12.

VIII. The compounds of the formula Ia can for example be prepared by reaction of e.g. alkali metal hydroxides or earth alkali metal hydroxides with arylglyoxalic acids (J), preferably in water as solvent:

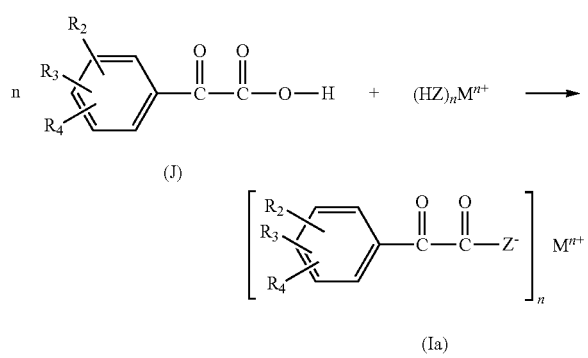

or by estersaponification of arylglyoxylic acid esters with metal hydroxides mentioned above.

$R_1$, $R_2$, $R_3$, $R_4$, Z, M and n are as defined above. Z is preferably O.

In the preparation of "asymmetric" compounds of the formula I or Ia, with n=2, i.e. those in which $R_2$, $R_3$, $R_4$ and $R_6$, $R_7$, $R_8$ have different definitions, the reaction is carried out using the appropriate, differing precursors, judiciously in a ratio of 1:1.

In general, the reactions I, III, IV and VII can be carried out without using a solvent, with one of the reaction components which is liquid, for example the diol, acting as solvent. It is also possible, however, to carry out the reactions in an inert solvent. Examples of suitable solvents are aliphatic or aromatic hydrocarbons such as alkanes and alkane mixtures, cyclohexane, benzene, toluene or xylene, for example. The boiling point of these solvents, however, should lie above that of the alcohol which is formed in the course of the reaction.

The other syntheses set out above are judiciously conducted in an inert solvent. Suitable examples are those indicated above.

In the case of reactions I, III and IV it is judicious to ensure that the alcohol which forms in the course of the reaction is removed from the reaction mixture. This takes place, for example, by distillation.

The reactions are carried out at different temperatures depending on the starting materials and solvents used. The temperatures and other reaction conditions required for the corresponding reactions are generally known and are familiar to the skilled worker.

The reaction products can be separated and purified by general, customary methods, for example by crystallization, distillation or chromatography.

The preparation of the starting materials required to synthesize the compounds of the formula I or Ia is generally known and is familiar to the skilled worker. The starting materials (B), (C), (D) and (F) where $R_2$, $R_3$ and $R_4$=H, indeed, are obtainable commercially.

For instance, the arylglyoxalic esters (B), for example, are obtained by Friedel-Crafts reaction from the aryls and from the corresponding oxocarboxylic methyl ester chloride, or by esterifying arylglyoxalic chlorides (C) with alcohols.

Arylglyoxalic chlorides (C) can be obtained, for example, by chlorinating the corresponding acid with, for example, $SOCl_2$.

Arylcarboxylic cyanides (F) can be obtained, for example, by reacting the corresponding acid chlorides with CuCN.

The preparation of arylacetic methyl esters (D) is possible, for example, by acid-catalysed reaction of aryl-$CH_2$—CN with methanol. This reaction is described, for example, in *Org. Syn. Coll. Vol. I,* 270. The corresponding aryl-$CH_2$-cyanides can be obtained, for example, from the corresponding chlorides using NaCN, as is disclosed, for example, in *Org. Syn. Coll. Vol, I,* 107 and *Org. Syn. Coll. Vol IV,* 576.

The synthesis of arylacetic ethyl esters (D) is to be found, for example, in *J. Chem. Soc. Chem. Comm* (1969), 515, the corresponding aryl bromide being reacted with $N_2CH_2COOC_2H_5$ in the presence of Li/diethyl ether, CuBr. Another method, the reaction of aryl bromides with ethyl acetate and NaH, is described, for example, in *J. Am. Chem. Soc.* (1959) 81, 1627. *J. Org. Chem.* (1968) 33, 1675 sets out the Grignard reaction of aryl bromides with $BrCH_2COOC_2H_5$ to give the arylacetic ethyl ester (D).

The preparation of the alcohols, thiols or amines (A) is familiar to the skilled worker and is widely described in the literature. Many of these compounds are obtainable commercially.

Subject of the invention are also those compounds of the formula I and Ia which are novel, in particular the compounds of examples 3, 4, 5, 6, 7, 9, 12, 13, 14, 15, 16, 18, 19, 20, 30, 32, 33, 34, 35, 36, 38, 39, 40, 41, 42, 43, 45, 46, 47, 48, 49, 50, 51, 52, 53, 54, 57, 60, 61, 62, 63, 65, 66, 67, 68 and 69 as described below.

Another embodiment of the invention are compounds of the formula Ib

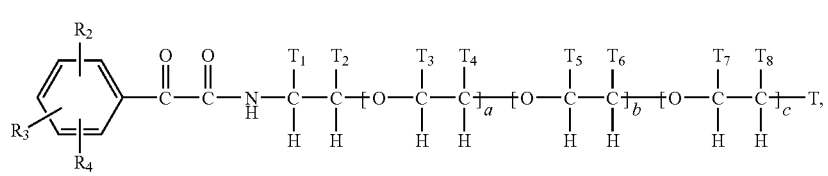

wherein $T_1$, $T_2$, $T_3$, $T_4$, $T_5$, $T_6$, $T_7$, $T_8$ independently of one another are hydrogen or $C_1$-$C_4$alkyl;

T is $NR_{12}COR_9$, $NR_{10}R_{11}$,

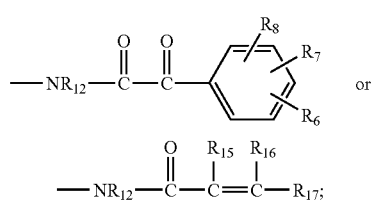

a, b, c independently of one another are an integer from 0 to 50, preferably from 0 to 10, where the total of a+b+c is 2 or higher; and $R_2$, $R_3$, $R_4$, $R_6$, $R_7$, $R_8$, $R_9$, $R_{10}$, $R_{11}$, $R_{12}$, $R_{15}$, $R_{16}$ and $R_{17}$ are as defined above.

Interesting in particular are compounds of the formula Ic

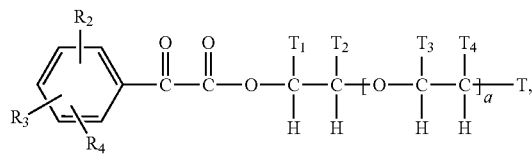

wherein $T_1, T_2, T_3, T_4, T_5, T_6, T_7, T_8$ independently of one another are hydrogen or $C_1$-$C_4$alkyl;
a is an integer from 4 to 50, preferably from 4 to 20;
T is

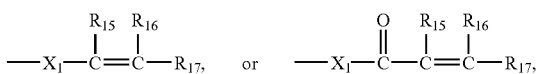

$OR_9$, $SR_9$, $NR_{10}R_{11}$, halogen, unsubstituted phenyl, or phenyl substituted by one or more $C_1$-$C_{24}$alkyl, $C_3$-$C_{25}$cycloalkyl, $C_2$-$C_{24}$alkenyl, $C_2$-$C_{24}$alkinyl, phenyl, $OR_9$, $SR_9$, $COR_9$, $COOR_9$, $OCOR_9$, $CON_{10}R_{11}$, $OCONR_{10}R_{11}$,

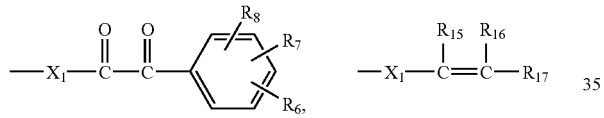

and/or

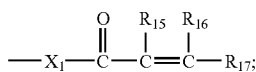

$R_2, R_3, R_4, R_6, R_7, R_8, R_9, R_{10}, R_{11}, R_{12}, X_1, R_{15}, R_{16}$ and $R_{17}$ are as defined above.

Also of interest are compounds of the formula (Id)

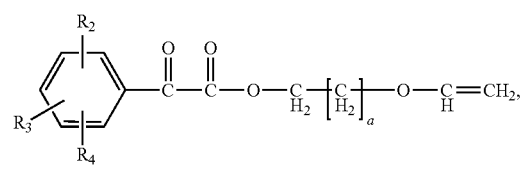

wherein
a is an integer from 1 to 7, preferably from 1 to 3; and
$R_2, R_3$, and $R_4$ are as defined above.

Another subject of the invention are compounds of the formula Ie

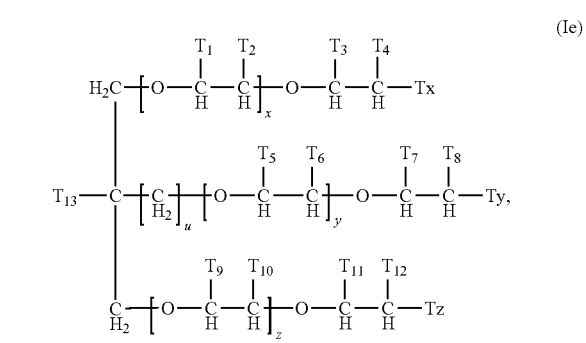

wherein
$T_1, T_2, T_3, T_4, T_5, T_6, T_7, T_8, T_9, T_{10}, T_{11}, T_{12}$ independently of one another are hydrogen or $C_1$-$C_4$alkyl;
$T_{13}$ is hydrogen or $C_1$-$C_4$alkyl, preferably hydrogen or ethyl;
$T_x, T_y, T_z$ independently of one another are $NR_{12}COR_9$, $NR_{10}R_{11}$,

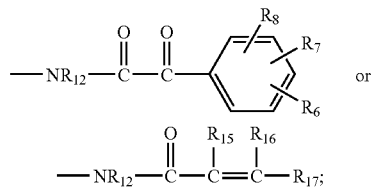

provided that at least one of $T_x$, $T_y$ or $T_z$ is

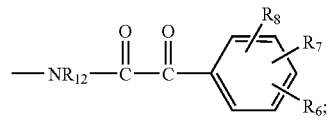

u is an integer from 0 to 10, preferably from 0 to 1;
x, y, z independently of one another are integers from 0 to 50, preferably from 4 to 50; and
$R_6, R_7, R_8, R_9, R_{10}, R_{11}, R_{12}, R_{15}, R_{16}$ and $R_{17}$ are as defined above.

The specific meanings of the defined radicals are as given above for the compounds of the formula I and Ia.
$T_1, T_2, T_3, T_4, T_5, T_6, T_7, T_8, T_9, T_{10}, T_{11}, T_{12}$, preferably independently of one another are hydrogen or methyl). $T_{13}$ is preferably hydrogen or ethyl;
T in formula Ic preferably is $OR_9$,

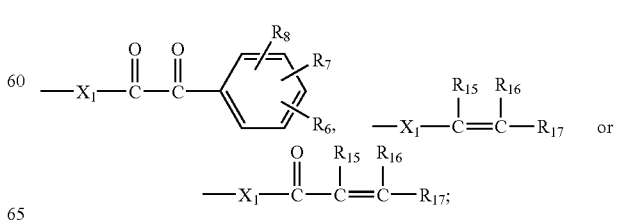

where $X_1$ is preferably O.

The compounds of the formula I, Ia, Ib, Ic, Id, and Ie are photoinitiators and are for example suitable to be used in a process as described above in steps b) and d), in particular in step b).

The preparation of the compounds of the formula Ib, Ic, Id and Ie is carried out according to the methods as described above for the compounds of the formula I.

The above photoinitiators of the formula I or Ia in the process according to the invention may be used singly or in any combination with one another or with further known photoinitiators and in principle any compounds and mixtures that form one or more free radicals when irradiated with electromagnetic waves. These include initiator systems consisting of a plurality of initiators and systems that function independently of one another or synergistically. In addition to coinitiators, for example amines, thiols, borates, enolates, phosphines, carboxylates and imidazoles, it is also possible to use sensitisers, for example acridines, xanthenes, thiazenes, coumarins, thioxanthones, triazines and dyes. A description of such compounds and initiator systems can be found e.g. in Crivello J. V., Dietliker K. K., (1999): Chemistry & Technology of UV & EB Formulation for Coatings, Inks & Paints, and in Bradley G. (ed.) Vol. 3: Photoinitiators for Free Radical and Cationic Polymerisation 2nd Edition, John Wiley & Son Ltd.

The photoinitiator of the formula I or Ia suitable for the process according to the invention in step b) may be either an initiator having an unsaturated group or an initiator not having such a group.

Known photoinitiators, that may be used in combination with the compound of the formula I or Ia are for example compounds and derivatives derived, from the following classes of compounds: benzoins, benzil ketals, acetophenones, hydroxyalkylphenones, aminoalkylphenones, mono- and bis-acylphosphine oxides, mono-and bisacylphosphine sulfides, acyloxyiminoketones, alkylamino-substituted ketones, such as Michler's ketone, peroxy compounds, dinitrile compounds, halogenated acetophenones, other phenylglyoxylates, other dimeric phenylglyoxalates, benzophenones, oximes and oxime esters, thioxanthones, coumarins, ferrocenes, titanocenes, onium salts, sulfonium salts, iodonium salts, diazonium salts, borates, triazines, bisimidazoles, polysilanes and dyes. It is also possible to use combinations of the compounds from the mentioned classes of compounds with one another and combinations with corresponding coinitiator systems and/or sensitisers.

Examples of such additional photoinitiator compounds are α-hydroxycyclohexylphenylketone or 2-hydroxy-2-methyl-1-phenyl-propanone, (4-methylthiobenzoyl)-1-methyl-1-morpholino-ethane, (4-morpholino-benzoyl)-1-benzyl-1-dimethylamino-propane, (4-morpholinobenzoyl)-1-(4-methylbenzyl)-1-dimethylamino-propane, (3,4-dimethoxybenzoyl)-1-benzyl-1-dimethylamino-propane, benzildimethylketal, (2,4,6-trimethyl benzoyl)-diphenylphosphinoxid, (2,4,6-trimethylbenzoyl)-ethoxy-phenylphosphinoxid, bis(2,6-dimethoxybenzoyl)-(2,4,4-trimethyl-pent-1-yl)phosphinoxid, bis(2,4,6-trimethylbenzoyl)-phenyl-phosphinoxid, bis(2,4,6-trimethylbenzoyl)-isopropylphosphinoxid, or bis(2,4,6-trimethylbenzoyl)-(2,4-dipentoxyphenyl)-phosphinoxid, dicyclopentadienyl-bis(2,6-difluor-3-pyrrolo)titan, bisacridine derivatives like 1,7-bis(9-acridinyl)heptane, oxime esters, for example 1-phenyl-1,2-propanedione-2-(o-benzoyl)oxime, 1-phenyl-1,2-propanedione-2-(o-ethoxycarbonyl)oxime or other oxime esters as for example described in GB 2339571 and US2001/0012596; as well as benzophenone, 4-phenylbenzophenone, 4-phenyl-3'-methylbenzophenone, 4-phenyl-2',4',6'-trimethylbenzophenone, 4-methoxybenzophenone, 4,4'-dimethoxybenzophenone, 4,4'-dimethylbenzophenone, 4,4'-dichlorobenzophenone, 4,4'-dimethylaminobenzophenone, 4,4'-diethylaminobenzophenone, 4-methylbenzophenone, 2,4,6-trimethylbenzophenone, 4-(4-methylthiophenyl)-benzophenone, 3,3'-dimethyl-4-methoxybenzophenone, methyl-2-benzoylbenzoat, 4-(2-hydroxyethylthio)-benzophenone, 4-(4-tolylthio)benzophenone, 4-benzoyl-N,N,N-trimethyl-benzolmethanaminiumchloride, 2-hydroxy-3-(4-benzoylphenoxy)-N,N,N-trimethyl-1-propanaminiumchloride monohydrate, 4-(13-acryloyl-1,4,7,10,13-pentaoxamidecyl)-benzophenone, 4-benzoyl-N,N-dimethyl-N-[2-(1-oxo-2-propenyl)oxy]ethyl-benzolmethanaminiumchloride; 2,2-dichloro-1-(4-phenoxyphenyl)-ethanone, 4,4'-bis(chloromethyl)-benzophenone, 4-methylbenzophenone, 2-methylbenzophenone, 3-methylbenzophenone, 4-chlorobenzophenone; as well as 2-chlorothioxanthone, 2,4-diethylthioxanthone, 2-isopropylthioxanthone, 3-isopropylthioxanthone, 1-chloro-4-propoxythioxanthone.

Further, photoinitiators having an unsaturated group may be used in combination with compounds of the formula I or Ia.

The publications indicated below provide specific examples of such photoinitiator compounds having an ethylenically unsaturated function, and the preparation thereof:

Unsaturated aceto-and benzo-phenone derivatives are described, for example, in U.S. Pat. Nos. 3,214,492, 3,429,852, 3,622,848 and U.S. Pat. No. 4,304,895, for example

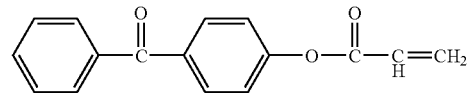

Also suitable, for example, are

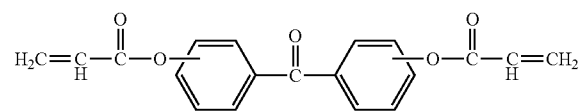

and further copolymerisable benzophenones, e.g. from UCB, Ebecryl P36 or in the form of Ebecryl P38 diluted in 30% tripropylene glycol diacrylate.

Copolymerisable, ethylenically unsaturated acetophenone compounds can be found, for example, in U.S. Pat. No. 4,922,004, for example

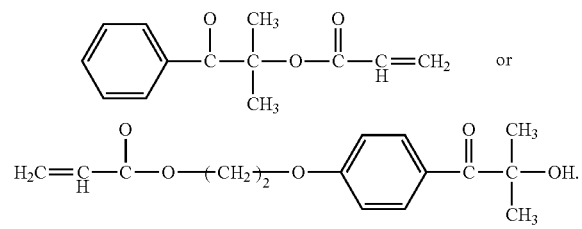

2-Acryloyl-thioxanthone has been published in Eur. Polym. J. 23, 985 (1987). Examples such as

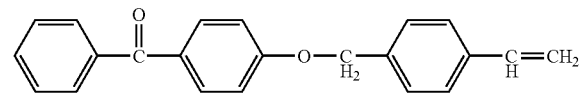

are described in DE 2 818 763. Further unsaturated carbonate-group-containing photoinitiator compounds can be found in EP 377 191. UVECRYL® P36 (already mentioned above), from UCB, is a benzophenone bonded to an acrylic function by ethylene oxide units (see Technical Bulletin 2480/885 (1985) from UCB or New. Polym. Mat. 1, 63 (1987)):

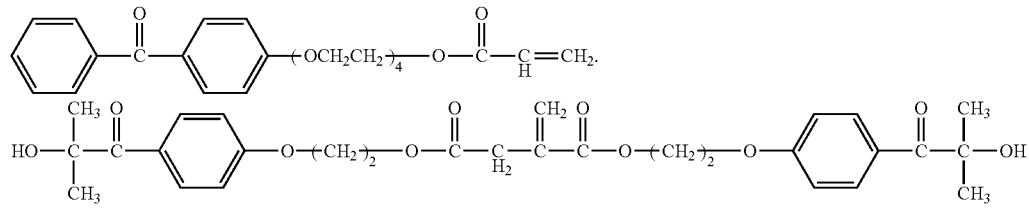

has been published in Chem. Abstr. 128: 283649r.

DE 195 01 025 gives further suitable ethylenically unsaturated photoinitiator compounds. Examples are 4-vinyloxycarbonyloxybenzophenone, 4-vinyloxycarbonyloxy-4'-chlorobenzophenone, 4-vinyloxycarbonyloxy-4'-methoxybenzophenone, N-vinyloxycarbonyl-4-aminobenzophenone, vinyloxycarbonyloxy-4'-fluorobenzophenone, 2-vinyloxycarbonyloxy-4'-methoxybenzophenone, 2-vinyloxycarbonyloxy-5-fluoro-4'-chlorobenzophenone, 4-vinyloxycarbonyloxyacetophenone, 2-vinyloxycarbonyloxyacetophenone, N-vinyloxycarbonyl-4-aminoacetophenone, 4-vinyloxycarbonyloxybenzil, 4-vinyloxycarbonyloxy-4'-methoxybenzil, vinyloxycarbonylbenzoin ether, 4-methoxybenzoinvinyloxycarbonyl ether, phenyl(2-vinyloxycarbonyloxy-2-propyl)-ketone, (4-isopropylphenyl)-(2-vinyloxycarbonyloxy-2-propyl)-ketone, phenyl-(1-vinyloxycarbonyloxy)-cyclohexyl ketone, 2-vinyloxycarbonyloxy-9-fluorenone, 2-(N-vinyloxycarbonyl)-9-aminofluorenone, 2-vinylcarbonyloxymethylanthraquinone, 2-(N-vinyloxycarbonyl)-aminoanthraquinone, 2-vinyloxycarbonyloxythioxanthone, 3-vinylcarbonyloxythioxanthone or

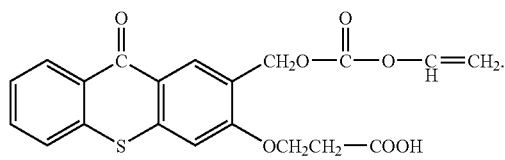

U.S. Pat. No. 4,672,079 discloses inter alia the preparation of 2-hydroxy-2-methyl(4-vinylpropiophenone), 2-hydroxy-2-methyl-p-(1-methylvinyl)propiophenone, p-vinylbenzoyl-cyclohexanol, p-(1-methylvinyl)benzoyl-cyclohexanol.

Also suitable are the reaction products, described in JP Kokai Hei 2-292307, of 4-[2-hydroxyethoxy) -benzoyl]-1-hydroxy-1-methyl-ethane (IRGACURE® 2959, Ciba Spezialitatenchemie) and isocyanates containing acryloyl or methacryloyl groups, for example

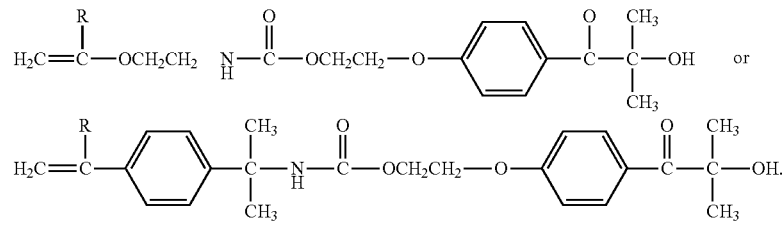

(wherein R = H or CH₃)

Further examples of suitable photoinitiators are

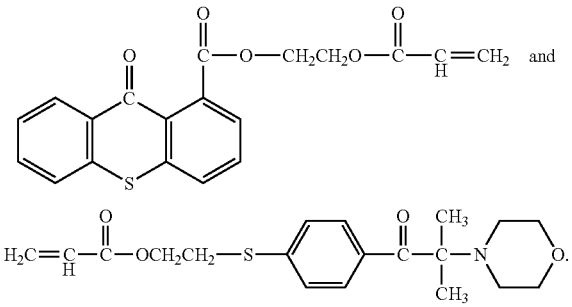

The following examples are described in Radcure '86, Conference Proceedings, 4-43 to 4-54 by W. Bäumer et al.

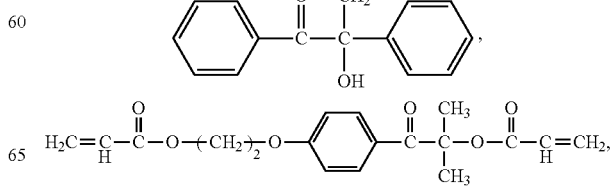

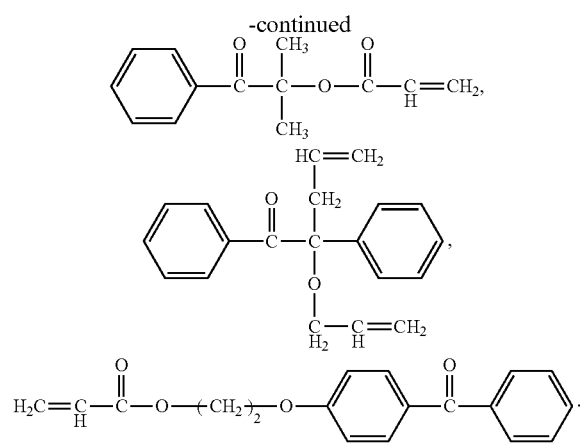

G. Wehner et al. report in Radtech '90 North America on

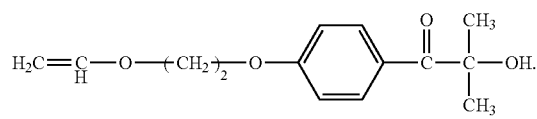

In the process according to the invention there are also suitable the compounds presented at RadTech 2002, North America loyl or methacryloyl groups or with other compounds containing acryloyl or methacryloyl groups, see e.g. U.S. Pat. No. 4,922,004.

Many of the photoinitiators to be optionally used in combination with the photoinitiators of the formula I are commercially available, e.g. under the trademark IRGACURE (Ciba Specialty Chemicals), ESACURE (Fratelli Lamberti), LUCIRIN (BASF), VICURE (Stauffer), GENOCURE, QUANTACURE (Rahn/Great Lakes), SPEEDCURE (Lambsons), KAYACURE (Nippon Kayaku), CYRACURE (Union Carbide Corp.), DoubleCure (Double Bond), EBECRYL P (UCB), FIRSTCURE (First Chemical), etc.

Commercially available unsaturated photoinitiators are, for example, 4-(13-acryloyl-1,4,7,10,13-pentaoxamidecyl)-benzophenone (UVECRYL P36 from UCB), 4-benzoyl-N,N-dimethyl-N-[2-(1-oxo-2-propenyl)oxy]ethylphenyl-methanaminiu-m chloride (Quantacure ABQ from Great Lakes), and some copolymerisable unsaturated tertiary amines (UVECRYL P101, UVECRYL P104, UVECRYL P105, UVECRYL P115 from UCB Radcure Specialties) or copolymerisable aminoacrylates (Photomer 4116 and Photomer 4182 from Ackros; Laromer LR8812 from BASF; CN381 and CN386 from Cray Valley).

In the process according to the invention, in particular in step b), it is possible to use either saturated or unsaturated photoinitiators of the formula I. In the process according to the invention it is of course also possible to employ mixtures of different photoinitiators, for example mixtures of saturated and unsaturated photoinitiators, as well as mixtures of compounds of the formula I with other photoinitiators.

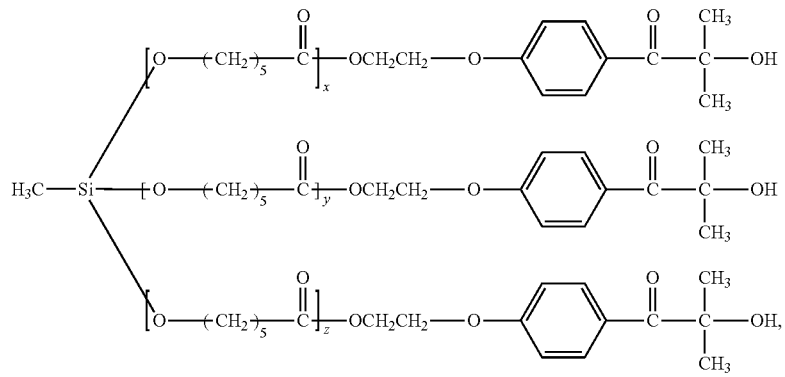

wherein x, y and z are an average of 3 (SiMFPI2) and

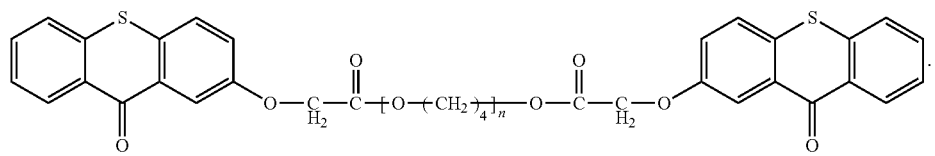

(MFPITX)

The preparation of such photoinitiator compounds is known to the person skilled in the art and has already been described in a large number of publications.

For example, compounds containing unsaturated groups can be prepared by reaction of 4-[2-hydroxyethoxy)-benzoyl]-1-hydroxy-1-methyl-ethane (IRGACURE®2959, Ciba Specialty Chemicals) with isocyanates containing acry- The photoinitiator, or where applicable the mixture of a plurality of photoinitiators and/or coinitiators, is applied to the corona-, plasma- or flame-pretreated substrate, for example, in pure form, that is to say without further additives, or in combination with a monomer or oligomer, or dissolved in a solvent. The initiator, or the initiator mixture, can also e.g. be in molten form. The initiator, or the initiator mixture, can also, for example, be dispersed, suspended or emulsified with water, a dispersant being added as necessary. Of course, it is also possible to use any mixture of the above-mentioned components, photoinitiator, monomer, oligomer, solvent, water.

Suitable dispersants, e.g. any surface-active compounds, preferably anionic and non-ionic surfactants, and also polymeric dispersants, are usually known to the person skilled in the art and are described, for example, in U.S. Pat. No. 4,965,294 and U.S. Pat. No. 5,168,087.

Suitable solvents are in principle any substances in which the photoinitiator, or the photoinitiators, can be converted into a state suitable for application, whether in the form of a solution or in the form of a suspension or emulsion. Suitable solvents are, for example, alcohols, such as ethanol, propanol, isopropanol, butanol, ethylene glycol etc., ketones, such as acetone, methyl ethyl ketone, acetonitrile, aromatic hydrocarbons, such as toluene and xylene, esters and aldehydes, such as ethyl acetate, ethyl formate, aliphatic hydrocarbons, e.g. petroleum ether, pentane, hexane, cyclohexane, halogenated hydrocarbons, such as dichloromethane, chloroform, or water, or alternatively oils, natural oils, castor oil, vegetable oil etc., and also synthetic oils. This description is on no account exhaustive and is given merely by way of example.

Alcohols, water and esters are preferred.

The monomers and/or oligomers containing at least one ethylenically unsaturated group, which optionally are used in step b) of the process according to the invention may contain one or more ethylenically unsaturated double bonds. They may be lower molecular weight (monomeric) or higher molecular weight (oligomeric). Examples of monomers having a double bond are alkyl and hydroxyalkyl acrylates and methacrylates, e.g. methyl, ethyl, butyl, 2-ethylhexyl and 2-hydroxyethyl acrylate, isobornyl acrylate and methyl and ethyl methacrylate. Further examples are acrylonitrile, acrylamide, methacrylamide, N-substituted (meth)acrylamides, vinyl esters, such as vinyl acetate, vinyl ethers, such as isobutyl vinyl ether, styrene, alkyl-and halo-styrenes, N-vinylpyrrolidone, vinyl chloride and vinylidene chloride, glycidyl (meth)acrylate.

Examples of monomers having more than one double bond are ethylene glycol diacrylate, 1,6-hexanediol diacrylate, propylene glycol diacrylate, dipropylene glycol diacrylate, tripropylene glycol diacrylate, neopentyl glycol diacrylate, hexamethylene glycol diacrylate and bisphenol-A diacrylate, 4,4'-bis(2-acryloyloxyethoxy)diphenylpropane, trimethylolpropane triacrylate, pentaerythritol triacrylate, pentaerythritol tetraacrylate, vinyl acrylate, divinylbenzene, divinyl succinate, diallyl phthalate, triallyl phosphate, triallyl isocyanurate, tris(hydroxyethyl) isocyanurate triacrylate (Sartomer 368; from Cray Valley) and tris(2-acryloylethyl) isocyanurate, ethyleneglycoldivinylether, diethyleneglycoldivinylether, triethyleneglycoldivinylether, polyethyleneglycol-mono-(meth)acrylate, polyethyleneglycol-di-(meth) acrylate, vinyl(meth)acrylate, CN435, SR415, SR9016 (Sartomer Company).

It is also possible to use acrylic esters of alkoxylated polyols, for example glycerol ethoxylate triacrylate, glycerol propoxylate triacrylate, trimethylolpropaneethoxylate triacrylate, trimethylolpropanepropoxylate triacrylate, pentaerythritol ethoxylate tetraacrylate, pentaerythritol propoxylate triacrylate, pentaerythritol propoxylate tetraacrylate, neopentyl glycol ethoxylate diacrylate or neopentyl glycol propoxylate diacrylate. The degree of alkoxylation of the polyols used may vary.

Examples of higher molecular weight (oligomeric) polyunsaturated compounds are acrylated epoxy resins, acrylated or vinyl-ether-or epoxy-group-containing polyesters, polyurethanes and polyethers. Further examples of unsaturated oligomers are unsaturated polyester resins, which are usually produced from maleic acid, phthalic acid and one or more diols and have molecular weights of about from 500 to 3000. In addition it is also possible to use vinyl ether monomers and oligomers, and also maleate-terminated oligomers having polyester, polyurethane, polyether, polyvinyl ether and epoxide main chains. In particular, combinations of vinyl-ether-group-carrying oligomers and polymers, as described in WO 90/01512, are very suitable, but copolymers of monomers functionalised with maleic acid and vinyl ether also come into consideration.

Also suitable are, for example, esters of ethylenically unsaturated carboxylic acids and polyols or polyepoxides, and oligomers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more such polymers.

Examples of unsaturated carboxylic acids are acrylic acid, methacrylic acid, crotonic acid, maleic acid, fumaric acid, itaconic acid, cinnamic acid and unsaturated fatty acids such as linolenic acid or oleic acid. Acrylic and methacrylic acid are preferred.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2-or 1,3-propanediol, 1,2-, 1,3-or 1,4-butanediol, pentanediol, hexanediol, octanediol, dodecanediol, diethylene glycol, triethylene glycol, polyethylene glycols from 200-35000, preferably from 200 to 1500, polypropylene glycols having molecular weights from 200-35000, preferably from 200 to 1500, polytetrahydrofuranes having molecular weights from 200-50000, preferably from 200 to 2000, 1,3-cyclopentanediol, 1,2-, 1,3-or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may have been partially or fully esterified by one or by different unsaturated carboxylic acid(s), it being possible for the free hydroxyl groups in partial esters to have been modified, for example etherified, or esterified by other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di-and tri-acrylate, 1,4-cyclohexane diacrylate, bisacrylates and bismethacrylates of polyethylene glycol having a molecular weight of from 200 to 1500, and mixtures thereof. Also suitable are the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2-or 1,3-propylenediamine, 1,2-, 1,3-or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine and di(β-aminoethoxy)-and di(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine trismethacrylamide, bis(methacrylamidopropoxy)ethane, β-methacrylamidoethyl methacrylate and N-[(β-hydroxyethoxy)ethyl]-acrylamide.

Specific examples are SARTOMER® 259, 344, 610, 603, 252 (provided by Cray Valley)

Suitable unsaturated polyesters and polyamides are derived, for example, from maleic acid and diols or diamines. The maleic acid may have been partially replaced by other dicarboxylic acids. They may be used together with ethylenically unsaturated comonomers, e.g. styrene. The polyesters and polyamides may also be derived from dicarboxylic acids and ethylenically unsaturated diols or diamines, especially from those having longer chains of e.g. from 6 to 20 carbon atoms. Examples of polyurethanes are those composed of saturated diisocyanates and unsaturated diols or unsaturated diisocyanates and saturated diols.

Polybutadiene and polyisoprene and copolymers thereof are known. Suitable comonomers include, for example, olefins, such as ethylene, propene, butene, hexene, (meth)acrylates, acrylonitrile, styrene and vinyl chloride. Polymers having (meth)acrylate groups in the side chain are likewise known. Examples are reaction products of novolak-based epoxy resins with (meth)acrylic acid; homo-or co-polymers of vinyl alcohol or hydroxyalkyl derivatives thereof that have been esterified with (meth)acrylic acid; and homo-and co-polymers of (meth)acrylates that have been esterified with hydroxyalkyl (meth)acrylates.

In the context of the present Application the term (meth) acrylate includes both the acrylate and the methacrylate.

An acrylate or methacrylate compound is especially used as the mono-or poly-ethylenically unsaturated compound.

Very special preference is given to polyunsaturated acrylate compounds, such as have already been mentioned above.

In process step b) for example a compound of the formula I, comprising an unsaturated group is used as such. Or, for example, a compound of the formula I, comprising an unsaturated group is used together with another photoinitiator, without an unsaturated group. Another possibility is to use a compound of the formula I without an unsaturated group in combination with another photoinitiator, comprising an unsaturated group. For example the use of a compound of the formula I, not comprising an unsaturated group together with a monomer or oligomer is suitable. Or, all combinations as mentioned above together with a monomer or oligomer may be employed. It's evident, that all combination may further be incorporated in a solvent, e.g. water.

The invention relates also to a process wherein the photoinitiators or mixtures thereof with monomers or oligomers are used in combination with one or more liquids (such as solvents, e.g. water) in the form of solutions, suspensions and emulsions.

Also of interest is a process wherein the photoinitiator used in process step b) or the mixture of photoinitiators is used in molten form.

After the application of the photoinitiator in step b) and step c), the workpiece can be stored or immediately processed further.

In the context of the present invention electromagnetic radiation is used in steps c) and d). Preferably this is UV/VIS radiation, which is to be understood as being electromagnetic radiation in a wavelength range from 150 nm to 700 nm. Preference is given to the range from 250 nm to 500 nm. Suitable lamps are known to the person skilled in the art and are commercially available.

A large number of the most varied kinds of light source may be used. Both point sources and planiform radiators (lamp arrays) are suitable. Examples are: carbon arc lamps, xenon arc lamps, medium-pressure, super-high-pressure, high-pressure and low-pressure mercury radiators doped, where appropriate, with metal halides (metal halide lamps), microwave-excited metal vapour lamps, excimer lamps, superactinic fluorescent tubes, fluorescent lamps, argon incandescent lamps, flash lamps, photographic floodlight lamps, light-emitting diodes (LED), electron beams and X-rays. The distance between the lamp and the substrate to be irradiated may vary according to the intended use and the type and strength of the lamp and may be, for example, from 2 cm to 150 cm. Also suitable are laser light sources, for example excimer lasers, such as Krypton-F lasers for irradiation at 248 nm. Lasers in the visible range may also be used.

As already mentioned, the above description of suitable radiation sources relates both to irradiation step c) (fixing of the photoinitiator) in the process according to the invention and the procedure of process step d).

Advantageously the dose of radiation used in process step c) is e.g. from 1 to 1000 mJ/cm$^2$, such as 1-800 mJ/cm$^2$, or, for example, 1-500 mJ/cm$^2$, e.g. from 5 to 300 mJ/cm$^2$, preferably from 10 to 200 mJ/cm$^2$.

The process according to the invention can be carried out within a wide pressure range, the discharge characteristics shifting as the pressure increases from a pure low-temperature plasma towards a corona discharge and finally changing into a pure corona discharge at an atmospheric pressure of about 1000-1100 mbar.

The process is preferably carried out at a process pressure of from $10^{-6}$ mbar up to atmospheric pressure (1013 mbar), especially in the range of from $10^{-4}$ to $10^{-2}$ mbar as a plasma process and at atmospheric pressure as a corona process. The flame treatment is usually carried out at atmospheric pressure.

The process is preferably carried out using as the plasma gas an inert gas or a mixture of an inert gas with a reactive gas in step a).

When a corona discharge is used, this can be done in any gas atmosphere. Preferred gases are air, carbon containing gases (e.g. $CO_2$, CO), nitrogen containing gases (e.g. $N_2$, $N_2O$, $NO_2$, NO), oxygen containing gases (e.g. $O_2$, $O_3$), hydrogen containing gases (e.g. $H_2$, HCl, HCN), sulfur containing gases (e.g. $SO_2$), noble gases (e.g. He, Ne, Ar, Kr, Xe) or water, singly or in the form of mixtures.

Most preferred main gases are air, $N_2$ or $CO_2$ singly or in the form of mixtures, where there might be added minor quantities of one or more dopant gases, like e.g. carbon containing gases (e.g. $CO_2$, CO), nitrogen containing gases (e.g. $N_2$, $N_2O$, $NO_2$, NO), oxygen containing gases (e.g. $O_2$, $O_3$), hydrogen containing gases (e.g. $H_2$, HCl, HCN), sulfur containing gases (e.g. $SO_2$), noble gases (e.g. He, Ne, Ar, Kr, Xe) or water, where minor quantity means that the sum of the dopant gases is less than 50%, preferably less than 40%, more preferably less than 30% and still more preferred less than 20% and even more preferred less than 10% of the total gas mixture.

Most preferred main gases are air or $N_2$, singly or in the form of a mixture.

Most preferred dopant gases are $CO_2$, $N_2O$ or $H_2$ singly or in the form of a mixture.

The photoinitiator (formulation/solution) layer deposited in step b) has a thickness up to 10 microns, preferably from e.g. a monomolecular layer to 5 microns, especially from 5 nm to 1 micron.

After carrying out step c) the photoinitiator (formulation) has preferably a thickness ranging up to 1 micron, from e.g. a monomolecular layer to 500 nm, especially from 5 nm to 200 nm.

The plasma treatment of the inorganic or organic substrate in step a) preferably takes place for from 1 ms to 300 s, especially from 10 ms to 200 s.

In principle, it is advantageous to apply the photoinitiator as quickly as possible after the plasma-, corona-or flame-pretreatment, but for many purposes it may also be acceptable to carry out reaction step b) after a time delay. It is preferable, however, to carry out process step b) immediately after process step a) or within 24 hours after process step a).

Of interest is a process wherein process step c) is carried out immediately after process step b) or within 24 hours after process step b).

After the plasma-, corona-or flame-pretreatment, it is therefore possible in process step b) to apply to the pretreated substrate, for example, 0.0001-100%, e.g. 0.001-50%, 0.01-20%, 0.01-10%, 0.01-5%, 0.1-5%, especially 0.1-1% of a photoinitiator having an unsaturated group or, for example, 0.0001-99.9999%, e.g. 0.001-50%, 0.01-20%, 0.01-10%, 0.01-5%, 0.1-5%, especially 0.1-1% of a photoinitiator, e.g. one without an unsaturated group, and e.g. 0.0001-99.9999%, e.g. 0.001-50%, 0.01-20%, 0.01-10%, 0.01-5%, 0.1-5%, especially 0.1-1% of a monomer, such as an acrylate, methacrylate, vinyl ether etc. based on the total formulation which preferably contains solvent(s) and optionally other compounds such as defoamers, emulsifiers, surfactants, anti-fouling agents, wetting agents and other additives customarily used in the industry, especially the coating and paint industries.

The application of the photoinitiators, or mixtures thereof with one another or with monomers or oligomers, undiluted, in the form of melts, solutions, dispersions, suspensions or emulsions, aerosols, can be carried out in various ways. Application can be effected by vapor deposition, immersion, spraying, coating, brush application, knife application, roller application, offset printing, gravure printing, flexo printing, ink jet printing, screen printing, spin-coating and pouring. In the case of mixtures of photoinitiators with one another and with coinitiators and sensitisers, all possible mixing ratios can be used.

The photoinitiator (formulation/solution) in step b) can be applied on the whole surface of the substrate, or can be applied only on selected areas.

Many possible methods of drying coatings are known and they can all be used in the claimed process, in step c) as well as in step d). For example, it is possible to use hot gases, IR radiators, microwaves and radio frequency radiators, ovens and heated rollers. Drying can also be effected, for example, by absorption, e.g. penetration into the substrate. This relates especially to the drying in process step c). Drying can take place, for example, at temperatures of from 0° C. to 300° C., for example from 20° C. to 200° C.

The irradiation of the coating in order to fix the photoinitiator in process step c) (and also to cure a formulation in process step d) can be carried out, as already mentioned above, using any sources that emit electromagnetic waves of wavelengths that can be absorbed by the photoinitiators used. Such sources are generally light sources that emit light in the range from 200 nm to 700 nm. It may also be possible to use electron beams. In addition to customary radiators and lamps it is also possible to use lasers and LEDs (Light Emitting Diodes).

Another source of UV-radiation (instead or in addition to UV-lamps) is for example corona treatment or plasma treatment as described above for step a). Said corona-or plasma treatment, in particular corona treatment, can also be applied in steps c) and/or d), especially in c). Preferably the irradiation in step c) is carried out with UV-lamps. Accordingly, in the context of the present invention the term "irradiation of the coating in order to fix the photoinitiator in process step c)" and "irradiation with electromagnetic waves" according to step c) besides a conventional irradiation via UV-lamps also encompasses a plasma-or corona treatment.

The whole area of the coating or parts thereof may be irradiated. Partial irradiation is of advantage when only certain regions are to be rendered adherent. Irradiation can also be carried out using electron beams.

The drying and/or irradiation (in steps c) and/or d)) can be carried out under air or under inert gas. Nitrogen gas comes into consideration as inert gas, but other inert gases, such as $CO_2$ or argon, helium etc. or mixtures thereof, can also be used. Suitable systems and apparatus are known to the person skilled in the art and are commercially available.

Strongly adherent coatings are important not only as protective layers or coverings, which may additionally be pigmented, but also for image-forming coatings, for example in resist and printing plate technology. In the case of image-forming processes, the irradiation can be effected through a mask or by writing using moving laser beams (Laser Direct Imaging—LDI). Such partial irradiation can be followed by a development or washing step in which portions of the applied coating are removed by means of solvents and/or water or mechanically.

When the process according to the invention is used in the production of image-forming coatings (imaging), the image-forming step can be carried out in process step c).

The invention therefore relates also to a process wherein portions of the photoinitiators, or mixtures thereof with monomers and/or oligomers, applied in process step b) that have not been crosslinked after irradiation in process step c) are removed by treatment with a solvent and/or water and/or mechanically.

The pretreated and photoinitiator-coated substrate can be subjected to a further process step d), which means to apply a further coating, which after drying and/or curing strongly adheres to the subtrate via the photoinitiator layer applied in step b).

Process step d) can be performed immediately after the coating and drying in accordance with process steps a), b) and c) or the coated substrate can be stored in the pretreated form.

The formulation applied in step d) may for example be d1) a customary photocurable composition to be cured with UV/VIS or an electron beam, or d2) a customary coating, such coating being dried, for example, in air or thermally. The drying can be effected, for example, also by absorption, for example by penetration into the substrate.

In step d) on the substrate pretreated according to steps a), b) and c) also d3) a metal, half-metal or metal oxide may be deposited as final coating.

The application of the formulations according to d1) and d2) can be performed in the same manner as described above for the formulation of step b). The further coating according to step d) in addition may be a metal layer.

A coating according to d1) is preferred.

Interesting therefore is a process, wherein the further coating d) is d1) a solvent or waterborne composition, comprising at least one polymerizable monomer, e.g. an epoxide or an ethylenically unsaturated monomer or oligomer, that is cured with UV/VIS radiation or electron beam; or d2) a solvent or waterborne customary drying coating, e.g. a printing ink or laquer; or d3) a metal layer.

A formulation curable by UV/VIS or an electron beam is for example a radically curable composition (d1.1), a cationically curable composition (d1.2) or a composition which cures or crosslinkes on the action of a base (d1.3).

Suitable ethylenically unsaturated compounds in step d1.1) may comprise one or more ethylenically unsaturated double bonds and are low molecular (monomer) or higher molecular (oligomer), e.g. monomers or oligomers as described above for step b).

Preferably the composition according to d1.1) in addition to at least one unsaturated monomer or oligomer comprises, at least one photoinitiator and/or coinitiator for the curing with UV/VIS radiation.

Accordingly, subject of the invention also is a process, wherein step d1.1) a photopolymerizable composition, comprising at least one ethylenically unsaturated monomer and/or oligomer and at least one photoinitiator and/or coinitiator, is applied to the substrate, which has been pretreated with steps a), b) and c), and is cured with UV/VIS radiation or electron beam, preferably with UV/VIS radiation.

As photoinitiator in the photocurable compositions according to step d1.1) compounds of the formula I may be used, but also, preferably, all other photoinitiators or photoinitiator systems known in the art.

Examples of suitable compounds are given above in connection with step b). In particular suitable are the described compounds other than the ones of formula I.

Preferably in the compositions according to step d1.1) photoinitiators without unsaturated groups are used.

The compositions used in process step d1.1) need not necessarily comprise a photoinitiator—for example they may be customary electron-beam-curable compositions (without photoinitiator) known to the person skilled in the art. Compositions comprising a photoinitiator are preferred.

The compositions can be applied in layer thicknesses of from about 0.1 µm to about 1000 µm, especially about from 1 µm to 100 µm. In the range of low layer thicknesses <50 µm, pigmented compositions e.g. are also referred to as printing inks.

The compositions may comprise further additives as for example light stabilizers, coinitiators and/or sensitizers.

As coinitiators there come into consideration, for example, sensitisers which shift or broaden the spectral sensitivity and thus bring about an acceleration of the photopolymerisation. They are especially aromatic carbonyl compounds, for example benzophenone, thioxanthone, especially isopropyl thioxanthone, anthraquinone and 3-acylcoumarin derivatives, terphenyls, styryl ketones, and also 3-(aroylmethylene)-thiazolines, camphor quinone, and also eosine, rhodamine and erythrosine dyes.

Amines, for example, can also be regarded as photosensitisers when the photoinitiator layer grafted on according to the invention consists of a benzophenone or benzophenone derivative.

Further examples of photosensitisers are
1. Thioxanthones

Thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di[2-(2-methoxyethoxy)ethoxycarbonyl]thioxanthone, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride;

2. Benzophenones

Benzophenone, 4-phenylbenzophenone, 4-methoxybenzophenone, 4,4'-dimethoxybenzophenone, 4,4'-dimethylbenzophenone, 4,4'-dichlorobenzophenone, 4,4'-dimethylaminobenzophenone, 4,4'-diethylaminobenzophenone, 4-methylbenzophenone, 2,4,6-trimethylbenzophenone, 4-(4-methylthiophenyl)-benzophenone, 3,3'-dimethyl-4-methoxybenzophenone, methyl-2-benzoyl benzoate, 4-(2-hydroxyethylthio)-benzophenone, 4-(4-tolylthio)-benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxamidecyl)-benzophenone, 4-benzoyl-N,N-dimethyl-N-[2-(1-oxo-2-propenyl)oxy]ethyl-benzenemethanaminium chloride;

3. 3-Acylcoumarins

3-Benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonyl-bis[5,7-di(propoxy)coumarin], 3,3'-carbonyl-bis(7-methoxycoumarin), 3,3'-carbonyl-bis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-dimethoxy-3-(1-naphthoyl)- coumarin, 3-benzoylbenzo[f]coumarin, 7-diethylamino-3-thienoylcoumarin, 3-(4-cyanobenzoyl)-5,7-dimethoxycoumarin;
4. 3-(Aroylmethylene)-thiazolines
3-Methyl-2-benzoylmethylene-β-naphthothiazoline, 3-methyl-2-benzoylmethylene-benzothiazoline, 3-ethyl-2-propionylmethylene-β-naphthothiazoline;
5. Other Carbonyl Compounds Acetophenone, 3-methoxyacetophenone, 4-phenylacetophenone, benzil, 2-acetylnaphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethylaminobenzylidene)-ketones, such as 2-(4-dimethylamino-benzylidene)-indan-1-one or 3-(4-dimethylaminophenyl)-1-indan-5-yl-propenone, 3-phenylthiophthalimide, N-methyl-3,5-di(ethylthio)phthalimide, N-methyl-3,5-di(ethylthio)phthalimide.

In addition to those additives it is also possible for the composition to comprise further additives, especially light stabilisers. The nature and amount of such additional additives is governed by the intended use of the coating in question and will be familiar to the person skilled in the art.

As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used singly or in the form of mixtures, with or without the use of sterically hindered amines (HALS).

Examples of such UV absorbers and light stabilisers are
1. 2-(2'-Hydroxyphenyl)-benzotriazoles, e.g. 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)-phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl)-phenybenzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$—COO (CH$_2$)$_3$]$_2$— wherein R=3'-tert-butyl-4'-hydroxy-5'-2H-benzotriazol-2-yl-phenyl.
2. 2-Hydroxybenzophenones, e.g. the 4-hydroxy, 4-methoxy, 4-octyloxy, 4-decyloxy, 4-dodecyloxy, 4-benzyloxy, 4,2', 4'-trihydroxy or 2'-hydroxy-4,4'-dimethoxy derivative.
3. Esters of unsubstituted or substituted benzoic acids, e.g. 4-tert-butyl-phenyl salicylate, phenyl salicylate, octylphenyl salicylate, dibenzoylresorcinol, bis(4-tert-butylbenzoyl)-resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.
4. Acrylates, e.g. α-cyano-β,β-diphenylacrylic acid ethyl ester or isooctyl ester, α-methoxycarbonylcinnamic acid methyl ester, α-cyano-β-methyl-p-methoxycinnamic acid methyl ester or butyl ester, α-methoxycarbonyl-p-methoxycinnamic acid methyl ester, N-(β-methoxycarbonyl-β-cyanovinyl)-2-methyl-indoline.
5. Sterically hindered amines, e.g. bis(2,2,6,6-tetramethylpiperidyl) sebacate, bis(2,2,6,6-tetramethyl piperidyl) succinate, bis(1,2,2,6,6-pentamethyl piperidyl) sebacate, n-butyl-3,5-di-tert-butyl-4-hydroxybenzylmalonic acid bis(1,2,2,6,6-pentamethylpiperidyl) ester, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl)-1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4,5]decane-2,4-dione, bis(1-octyloxy-2,2,6,6-tetramethylpiperidyl) sebacate, bis(1-octyloxy-2,2,6,6-tetramethylpiperidyl) succinate, condensation product of N,N'-bis(2,2,6,6-tetramethyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4,5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione.
6. Oxalic acid diamides, e.g. 4,4'-dioctyloxyoxanilide, 2,2'-diethoxyoxanilide, 2,2'-dioctyloxy-5,5'-di-tert-butyl oxanilide, 2,2'-didodecyloxy-5,5'-di-tert-butyl oxanilide, 2-ethoxy-2'-ethyl oxanilide, N,N'-bis(3-dimethylaminopropyl) oxalamide, 2-ethoxy-5-tert-butyl-2'-ethyl oxanilide and a mixture thereof with 2-ethoxy-2'-ethyl-5,4'-di-tert-butyl oxanilide, mixtures of o-and p-methoxy-and also of o-and p-ethoxy-di-substituted oxanilides.
7. 2-(2-Hydroxyphenyl)-1,3,5-triazines, e.g. 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[4-(dodecyloxy/tridecyloxy-2-hydroxypropyl)oxy-2-hydroxyphenyl]-4,6-bis(2,4-dimethylphenyl)-1,3,5-triazine.

In addition to the light stabilisers mentioned above, other stabilisers, for example, such as phosphites or phosphonites, are also suitable.

8. Phosphites and phosphonites, e.g. triphenyl phosphite, diphenylalkyl phosphites, phenyldialkyl phosphites, tris (nonylphenyl)phosphite, trilauryl phosphite, trioctadecyl phosphite, distearyl-pentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, bis-isodecyloxy-pentaerythritol diphosphite, bis(2,4-di-tert-butyl-6-methylphenyl)pentaerythritol diphosphite, bis(2,4,6-tri-tert-butylphenyl) pentaerythritol diphosphite, tristearyl sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl) methyl phosphite, bis(2,4-di-tert-butyl-6-methylphenyl) ethyl phosphite.

Depending upon the field of use, it is also possible to use additives customary in the art, e.g. antistatics, flow improvers and adhesion promoters.

The compositions may also be pigmented when a suitable photoinitiator is chosen, it being possible for coloured pigments as well as white pigments to be used.

Subject of the invention also is a process, wherein after irradiation in process step d) portions of the coating are removed by treatment with a solvent and/or water and/or mechanically.

Compositions applied in process step d1) or d2) are, for example, pigmented or unpigmented surface coatings, release layers, inks, ink-jet inks; printing inks, for example screen printing inks, offset printing inks, flexographic printing inks; or overprint varnishes; or primers; or printing plates, offset printing plates; powder coatings, adhesives or repair coatings, repair varnishes or repair putty compositions.

The compositions according to d1.2) comprise cationically curable components and an initiator to start the crosslinking. Examples for cationically curable components are resins and compounds that can be cationically polymerised by alkyl-or aryl-containing cations or by protons. Examples thereof include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. These include also modified surface-coating resins, such as, for example, acrylic-modified polyester and alkyd resins. Examples of individual types of resins that are included under the terms acrylic, polyester and alkyd resins are described, for example, in Wagner, Sarx/Lackkunstharze (Munich, 1971), pages 86 to 123 and 229 to 238, or in Ullmann/Encyclopädie der techn. Chemie, 4$^{th}$ edition, volume 15 (1978), pages 613 to 628, or Ullmann's Encyclopedia of Industrial Chemistry, Verlag Chemie, 1991, Vol. 18, 360 ff., Vol. A19, 371 ff. The surface-coating preferably comprises an amino resin. Examples thereof include etherified and non-etherified melamine, urea, guanidine and biuret resins. Of special importance is acid catalysis for the curing of surface-coatings comprising etherified amino resins, such as, for example, methylated or butylated melamine resins (N-methoxymethyl-or N-butoxymethyl-melamine) or methylated/butylated glycolurils.

It is possible, for example, to use all customary epoxides, such as aromatic, aliphatic or cycloaliphatic epoxy resins. These are compounds having at least one, preferably at least two, epoxy group(s) in the molecule. Examples thereof are the glycidyl ethers and 5-methyl glycidyl ethers of aliphatic or cycloaliphatic diols or polyols, e.g. those of ethylene glycol, propane-1,2-diol, propane-1,3-diol, butane-1,4-diol, diethylene glycol, polyethylene glycol, polypropylene glycol, glycerol, trimethylolpropane or 1,4-dimethylolcyclohexane or of 2,2-bis(4-hydroxycyclohexyl)propane and N,N-bis (2-hydroxyethyl)aniline; the glycidyl ethers of di-and polyphenols, for example of resorcinol, of 4,4'-dihydroxyphenyl-2,2-propane, of novolaks or of 1,1,2,2-tetrakis(4-hydroxyphenyl)ethane. Examples thereof include phenyl glycidyl ether, p-tert-butyl glycidyl ether, o-icresyl glycidyl ether, polytetrahydrofuran glycidyl ether, n-butyl glycidyl ether, 2-ethylhexyl glycidyl ether, $C_{12/15}$alkyl glycidyl ether and cyclohexanedimethanol diglycidyl ether. Further examples include N-glycidyl compounds, for example the glycidyl compounds of ethyleneurea, 1,3-propyleneurea or 5-dimethyl-hydantoin or of 4,4'-methylene-5,5'-tetramethyldihydantoin, or compounds such as triglycidyl isocyanurate.

Further examples of glycidyl ether components that are suitable for the formulations are glycidyl ethers of polyhydric phenols obtained by the reaction of polyhydric phenols with an excess of chlorohydrin, such as, for example, epichlorohydrin (e.g. glycidyl ethers of 2,2-bis(2,3-epoxypropoxyphenol)propane. Further examples of glycidyl ether epoxides that can be used in connection with the present invention are described, for example, in U.S. Pat. No. 3,018,262 and in "Handbook of Epoxy Resins" by Lee and Neville, McGraw-Hill Book Co., New York (1967).

There is also a large number of commercially available glycidyl ether epoxides that are suitable, such as, for example, glycidyl methacrylate, diglycidyl ethers of bisphenol A, for example those obtainable under the trade names EPON 828, EPON 825, EPON 1004 and EPON 1010 (Shell); DER-331, DER-332 and DER-334 (Dow Chemical); 1,4-butanediol diglycidyl ethers of phenolformaldehyde novolak, e.g. DEN-431, DEN-438 (Dow Chemical); and resorcinol diglycidyl ethers; alkyl glycidyl ethers, such as, for example, $C_8$-$C_{10}$glycidyl ethers, e.g. HELOXY Modifier 7, $C_{12}$-$C_{14}$glycidyl ethers, e.g. HELOXY Modifier 8, butyl glycidyl ethers, e.g. HELOXY Modifier 61, cresyl glycidyl ethers, e.g. HELOXY Modifier 62, p-tert-butylphenyl glycidyl ethers, e.g. HELOXY Modifier 65, polyfunctional glycidyl ethers, such as diglycidyl ethers of 1,4-butanediol, e.g. HELOXY Modifier 67, diglycidyl ethers of neopentyl glycol, e.g. HELOXY Modifier 68, diglycidyl ethers of cyclohexanedimethanol, e.g. HELOXY Modifier 107, trimethylolethane triglycidyl ethers, e.g. HELOXY Modifier 44, trimethylolpropane triglycidyl ethers, e.g. HELOXY Modifier 48, polyglycidyl ethers of aliphatic polyols, e.g. HELOXY Modifier 84 (all HELOXY glycidyl ethers are obtainable from Shell).

Also suitable are glycidyl ethers that comprise copolymers of acrylic esters, such as, for example, styrene-glycidyl methacrylate or methyl methacrylate-glycidyl acrylate. Examples thereof include 1:1 styrene/glycidyl methacrylate, 1:1 methyl methacrylate/glycidyl acrylate, 62.5:24:13.5 methyl methacrylate/ethyl acrylate/glycidyl methacrylate.

The polymers of the glycidyl ether compounds can, for example, also comprise other functionalities provided that these do not impair the cationic curing.

Other suitable glycidyl ether compounds that are commercially available are polyfunctional liquid and solid novolak glycidyl ether resins, e.g. PY 307, EPN 1179, EPN 1180, EPN 1182 and ECN 9699.

It will be understood that mixtures of different glycidyl ether compounds may also be used. The glycidyl ethers are, for example, compounds of formula X

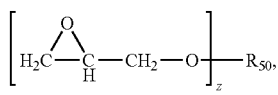

wherein z is a number from 1 to 6; and $R_{50}$ is a mono-to hexa-valent alkyl or aryl radical.

Preference is given, for example, to glycidyl ether compounds, wherein z is the number 1, 2 or 3; and $R_{50}$, when z=1, is unsubstituted or $C_1$-$C_{12}$alkyl-substituted phenyl, naphthyl, anthracyl, biphenylyl, $C_1$-$C_{20}$alkyl, or $C_2$-$C_{20}$alkyl interrupted by one or more oxygen atoms, or $R_{50}$, when z=2, is 1,3-phenylene, 1,4-phenylene, $C_6$-$C_{10}$cycloalkylene, unsubstituted or halo-substituted $C_1$-$C_{40}$alkylene, $C_2$-$C_{40}$alkylene interrupted by one or more oxygen atoms, or a group

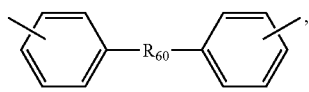

or $R_{50}$, when z=3, is a radical

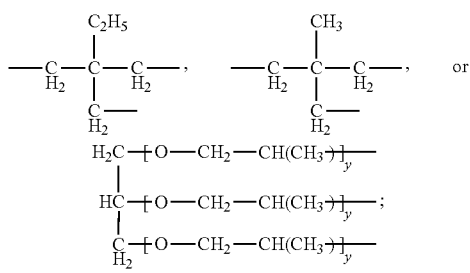

y is a number from 1 to 10; and $R_{60}$ is $C_1$-$C_{20}$alkylene, oxygen or

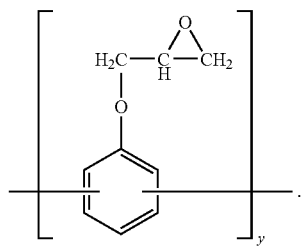

Further examples are polyglycidyl ethers and poly(β-methylglycidyl)ethers obtainable by the reaction of a compound containing at least two free alcoholic and/or phenolic hydroxy groups per molecule with the appropriate epichlorohydrin under alkaline conditions, or alternatively in the presence of an acid catalyst with subsequent alkali treatment. Mixtures of different polyols may also be used. Such ethers can be prepared with poly(epichlorohydrin) from acyclic alcohols, such as ethylene glycol, diethylene glycol and higher poly(oxyethylene) glycols, propane-1,2-diol and poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylol-propane, pentaerythritol and sorbitol, from cycloaliphatic alcohols, such as resorcitol, quinitol, bis(4-hydroxycyclohexyl)methane, 2,2-bis(4-hydroxycyclohexyl)propane and 1,1-bis-(hydroxymethyl)cyclohex-3-ene, and from alcohols having aromatic nuclei, such as N,N-bis(2-hydroxyethyl)aniline and p,p'-bis(2-hydroxyethylamino)diphenylmethane. They can also be prepared from mononuclear phenols, such as resorcinol and hydroquinone, and polynuclear phenols, such as bis(4-hydroxyphenyl)methane, 4,4-dihydroxydiphenyl, bis(4-hydroxyphenyl)sulfone, 1,1,2,2-tetrakis(4-hydroxyphenyl)ethane, 2,2-bis(4-hydroxyphenyl)-propane (bisphenol A) and 2,2-bis(3,5-dibromo-4-hydroxyphenyl)propane. Further hydroxy compounds suitable for the preparation of polyglycidyl ethers and poly(β-methylglycidyl)ethers are the novolaks obtainable by the condensation of aldehydes, such as formaldehyde, acetaldehyde, chloral and furfural, with phenols, such as, for example, phenol, o-cresol, m-cresol, p-cresol, 3,5-dimethylphenol, 4-chlorophenol and 4-tert-butylphenol.

Poly(N-glycidyl) compounds can be obtained, for example, by dehydrochlorination of the reaction products of epichlorohydrin with amines containing at least two amino-hydrogen atoms, such as aniline, n-butylamine, bis(4-aminophenyl)methane, bis(4-aminophenyl)-propane, bis(4-methylaminophenyl)methane and bis(4-aminophenyl)ether, sulfone and sulfoxide. Further suitable poly(N-glycidyl) compounds include triglycidyl isocyanurate, and N,N'-diglycidyl derivatives of cyclic alkyleneureas, such as ethyleneurea and 1,3-propyleneurea, and hydantoins, such as, for example, 5,5-dimethylhydantoin.

Poly(S-glycidyl) compounds are also suitable. Examples thereof include the di-S-glycidyl derivatives of dithiols, such as ethane-1,2-dithiol and bis(4-mercaptomethylphenyl)ether. There also come into consideration epoxy resins in which the glycidyl groups or β-methyl glycidyl groups are bonded to hetero atoms of different types, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethyl-hydantoin and 2-glycidyloxy-1,3-bis(5,5-dimethyl-1-glycidylhydantoin-3-yl)propane.

Preference is given to diglycidyl ethers of bisphenols. Examples thereof include diglycidyl ethers of bisphenol A, e.g. ARALDIT GY 250, diglycidyl ethers of bisphenol F and diglycidyl ethers of bisphenol S. Special preference is given to diglycidyl ethers of bisphenol A.

Further glycidyl compounds of technical importance are the glycidyl esters of carboxylic acids, especially di-and polycarboxylic acids. Examples thereof are the glycidyl esters of succinic acid, adipic acid, azelaic acid, sebacic acid, phthalic acid, terephthalic acid, tetra-and hexa-hydrophthalic acid, isophthalic acid or trimellitic acid, or of dimerised fatty acids.

Examples of polyepoxides that are not glycidyl compounds are the epoxides of vinylcyclohexane and dicyclopentadiene, 3-(3',4'-epoxycyclohexyl)-8,9-epoxy-2,4-dioxaspiro-[5.5]undecane, the 3',4'-epoxycyclohexylmethyl esters of 3,4-epoxycyclohexanecarboxylic acid, (3,4-epoxycyclohexyl-methyl 3,4-epoxycyclohexanecarboxylate), butadiene diepoxide or isoprene diepoxide, epoxidised linoleic acid derivatives or epoxidised polybutadiene.

Further suitable epoxy compounds are, for example, limonene monoxide, epoxidised soybean oil, bisphenol-A and bisphenol-F epoxy resins, such as, for example, ARALDIT® GY 250 (A), ARALDIT® GY 282 (F), ARALDIT® GY 285 (F).

Further suitable cationically polymerisable or crosslinkable components can be found, for example, also in U.S. Pat. No. 3,117,099, U.S. Pat. No. 4,299,938 and U.S. Pat. No. 4,339,567.

From the group of aliphatic epoxides there are suitable especially the monofunctional symbol α-olefin epoxides having an unbranched chain consisting of 10, 12, 14 or 16 carbon atoms. Because nowadays a large number of different epoxy compounds are commercially available, the properties of the binder can vary widely. One possible variation, for example depending upon the intended use of the composition, is the use of mixtures of different epoxy compounds and the addition of flexibilisers and reactive diluents.

The epoxy resins can be diluted with a solvent to facilitate application, for example when application is effected by spraying, but the epoxy compound is preferably used in the solvent-less state. Resins that are viscous to solid at room temperature can be applied hot.

Also suitable are all customary vinyl ethers, such as aromatic, aliphatic or cycloaliphatic vinyl ethers and also silicon-containing vinyl ethers. These are compounds having at least one, preferably at least two, vinyl ether groups in the molecule. Examples of vinyl ethers suitable for use in the compositions according to the invention include triethylene glycol divinyl ether, 1,4-cyclohexanedimethanol divinyl ether, 4-hydroxybutyl vinyl ether, the propenyl ether of propylene carbonate, dodecyl vinyl ether, tert-butyl vinyl ether, tert-amyl vinyl ether, cyclohexyl vinyl ether, 2-ethylhexyl vinyl ether, ethylene glycol monovinyl ether, butanediol monovinyl ether, hexanediol monovinyl ether, 1,4-cyclohexanedimethanol monovinyl ether, diethylene glycol monovinyl ether, ethylene glycol divinyl ether, ethylene glycol butylvinyl ether, butane-1,4-diol divinyl ether, hexanediol divinyl ether, diethylene glycol divinyl ether, triethylene glycol divinyl ether, triethylene glycol methylvinyl ether, tetraethylene glycol divinyl ether, pluriol-E-200 divinyl ether, polytetrahydrofuran divinyl ether-290, trimethylolpropane trivinyl ether, dipropylene glycol divinyl ether, octadecyl vinyl ether, (4-cyclohexyl-methyleneoxyethene)-glutaric acid methyl ester and (4-butoxyethene)-iso-phthalic acid ester.

Examples of hydroxy-containing compounds include polyester polyols, such as, for example, polycaprolactones or polyester adipate polyols, glycols and polyether polyols, castor oil, hydroxy-functional vinyl and acrylic resins, cellulose esters, such as cellulose acetate butyrate, and phenoxy resins.

Further cationically curable formulations can be found, for example, in EP 119425.

If desired, the cationically curable composition can also contain free-radically polymerisable components, such as ethylenically unsaturated monomers, oligomers or polymers as described above. Suitable materials contain at least one ethylenically unsaturated double bond and are capable of undergoing addition polymerisation.

Advantageously, the formulations comprise at least one photoinitiator. Suitable examples are known to the person skilled in the art and commercially available in a considerable number.

Representative examples are for example disclosed by J. V. Crivelleo and K. Dietliker in Photoinitiators for Free Radical Cationic & Anionic Photopolymerisation, $2^{nd}$ Ed. Vol III, Wiley. Examples are benzoyl peroxides (as e.g. described in U.S. Pat. No. 4,950,581, column 19, lines 17-25), or aromatic sulfonium salts, as e.g. disclosed in WO 03/008404 and WO 03/072567, phosphonium or iodonium salts, such as are described, for example, in U.S. Pat. No. 4,950,581, column 18, line 60 to column 19, line 10, WO 99/35188, WO 98/02493, WO 99/56177 and U.S. Pat. No. 6,306,555. Further suitable initiators are oximesulfonates.

Suitable sulfonium salts are obtainable, for example, under the trade names CYRACURE® UVI-6990, CYRACURE® UVI-6974 (Union Carbide), DEGACURE® KI 85 (Degussa), SP-55, SP-150, SP-170 (Asahi Denka), GE UVE 1014 (General Electric), SARCAT® KI-85 (=triarylsulfonium hexafluorophosphate; Sartomer), SARCAT® CD 1010 (=mixed triarylsulfonium hexafluoroantimonate; Sartomer); SARCAT® CD 1011(=mixed triarylsulfonium hexafluorophosphate; Sartomer).

Suitable iodonium salts are e.g. tolylcumyliodonium tetrakis(pentafluorophenyl)borate, 4-[(2-hydroxy-tetradecyloxy)phenyl]phenyliodonium hexafluoroantimonate or hexafluorophosphate (SARCAT® CD 1012; Sartomer), tolylcumyliodonium hexafluorophosphate, 4-isobutylphenyl-4'-methylphenyliodonium hexafluorophosphate (IRGACURE® 250, Ciba Specialty Chemicals), 4-octyloxyphenyl-phenyliodonium hexafluorophosphate or hexafluoroantimonate, bis(dodecylphenyl)iodonium hexafluoroantimonate or hexafluorophosphate, bis(4-methylphenyl)iodonium hexafluorophosphate, bis(4-methoxyphenyl)iodonium hexafluorophosphate, 4-methylphenyl-4'-ethoxyphenyliodonium hexafluorophosphate, 4-methylphenyl-4'-dodecylphenyliodonium hexafluorophosphate, 4-methylphenyl-4'-phenoxyphenyliodonium hexafluorophosphate. Of all the iodonium salts mentioned, compounds with other anions are, of course, also suitable. The preparation of iodonium salts is known to the person skilled in the art and described in the literature, for example U.S. Pat. Nos. 4,151,175, 3,862,333, 4,694,029, EP 562897, U.S. Pat. Nos. 4,399,071, 6,306,555, WO 98/46647 J. V. Crivello, "Photoinitiated Cationic Polymerization" in: UV Curing: Science and Technology, Editor S. P. Pappas, pages 24-77, Technology Marketing Corporation, Norwalk, Conn. 1980, ISBN No. 0-686-23773-0; J. V. Crivello, J. H. W. Lam, Macromolecules, 10, 1307 (1977) and J. V. Crivello, Ann Rev. Mater. Sci. 1983, 13, pages 173-190 and J. V. Crivello, Journal of Polymer Science, Part A: Polymer Chemistry, Vol. 37, 4241-4254 (1999).

Specific examples of oxime sulfonates are α-(octylsulfonyloxyimino)-4-methoxybenzylcyanide, 2-methyl-α-[5-[4-[[methyl-sulfonyl]oxy]imino]-2(5H)-thienylidene]-benzeneacetonitrile, 2-methyl-α-[5-[4-[[(n-propyl)sulfonyl]oxy]imino]-2(5H)-thienylidene]-benzeneacetonitrile, 2-methyl-α-[5-[4-[[(camphoryl)sulfonyl]oxy]imino]-2(5H)-thienylidene]-benzeneacetonitrile, 2-methyl-α-[5-[4-[[(4-methylphenyl)sulfonyl]oxy]imino]-2(5H)-thienylidene]-benzeneacetonitrile, 2-methyl-α-[5-[4-[[(n-octyl)sulfonyl]oxy]imino]-2(5H)-thienylidene]-benzeneacetonitrile, 2-methyl-α-[5-[[[[4-[[(4-methylphenyl)sulfonyl]oxy]phenyl]sulfonyl]oxy]imino]-2(5H)-thienylidene]-benzeneacetonitrile, 1,1'-[1,3-propanediylbis(oxy-4,1-phenylene)]bis[2,2,2-trifluoro-bis [O-(trifluoromethylsulfonyl)oxime]-ethanone, 1,1'-[1,3-propanediylbis(oxy-4,1-phenylene)]bis[2,2,2-trifluoro-bis[O-(propylsulfonyl)oxime]-ethanone, 1,1'-[1,3-propanediylbis(oxy-4,1-phenylene)]bis[2,2,2-trifluoro-bis[O-((4-methylphenyl)sulfonyl)oxime]-ethanone, α-(methylsulfonyloxyimino)-4-methoxybenzylcyanide, α-(methylsulfonyloxyimino)-3-methoxybenzylcyanide, α-(methylsulfonyloxyimino)-3,4-dimethylbenzylcyanide, α-(methylsulfonyloxyimino)-thiophene-3-acetonitrile, α-(isopropylsulfonyloxyimino)-thiophene-2-acetonitrile, cis/trans-α-(dodecylsulfonyloxyimino)-thiophene-2-acetonitrile.

Suitable oximesulfonates and their preparation can be found, for example, in WO 00/10972, WO 00/26219, GB 2348644, U.S. Pat. No. 4,450,598, WO 98/10335, WO 99/01429, EP 780729, EP 821274, U.S. Pat. No. 5,237,059, EP 571330, EP 241423, EP 139609, EP 361907, EP 199672, EP 48615, EP 12158, U.S. Pat. No. 4,136,055, WO 02/25376, WO 02/98870, WO 03/067332 and WO 04/74242. A summary of further photolatent acid donors is given in the form of a review by M. Shirai and M. Tsunooka in Prog. Polym. Sci., Vol. 21, 1-45 (1996). and in J. Crivello, K. Dietliker, "Photoinititiators for Free Radical Cationic & Anionic Photopolymerisation", $2^{nd}$ Edition, Volume III in the Series "Chemistry & Technology of UV & EB Formulation for Coatings, Inks & Paints", John Wiley/SITA Technology Limited, London, 1998, chapter III (p. 329-463).

It is evident for the person skilled in the art, that also the cationically curable formulations may further comprise customary additives, sensitizers, pigments and colorants etc. Examples are given above.

The base-catalysed polymerization, addition, condensation or substitution reaction may be carried out with low molecular mass compounds (monomers), with oligomers, with polymeric compounds, or with a mixture of such compounds. Examples of reactions which can be conducted both on monomers and on oligomers/polymers using the photoinitiators of the invention are the Knoevenagel reaction and the Michael addition reaction.

Of particular interest are compositions comprising an anionically polymerizable or crosslinkable organic material. The organic material may be in the form of monofunctional or polyfunctional monomers, oligomers or polymers.

Particularly preferred oligomeric/polymeric systems are binders such as are customary in the coatings industry.

Examples of base-catalysable binders of this kind are:
a) two-component systems comprising hydroxyl-containing polyacrylates, polyesters and/or polyethers and aliphatic or aromatic polyisocyanates;
b) two-component systems comprising functional polyacrylates and polyepoxide, the polyacrylate containing thiol, amino, carboxyl and/or anhydride groups, as described, for example, in EP 898202;
c) two-component systems comprising (poly)ketimines and aliphatic or aromatic polyisocyanates;
d) two-component systems comprising (poly)ketimines and unsaturated acrylic resins or acetoacetate resins or methyl α-acrylamidomethylglycolate;
e) two-component systems comprising (poly)oxazolidines and polyacrylates containing anhydride groups or unsaturated acrylic resins or polyisocyanates;
f) two-component systems comprising epoxy-functional polyacrylates and carboxyl-containing or amino-containing polyacrylates;
g) polymers based on allyl glycidyl ether;
h) two-component systems comprising a (poly)alcohol and/or (poly)thiol and a (poly)isocyanate;
i) two-component systems comprising an α,β-ethylenically unsaturated carbonyl compound and a polymer containing activated $CH_2$ groups, the activated $CH_2$ groups being present either in the main chain or in the side chain or in both, as is described, for example, in EP 161697 for (poly)malonate groups. Other compounds containing activated $CH_2$ groups are (poly)acetoacetates and (poly)cyanoacetates;
k) Two-component systems comprising a polymer containing activated $CH_2$ groups, the activated $CH_2$ groups being present either in the main chain or in the side chain or in both, or a polymer containing activated $CH_2$ groups such as (poly)acetoacetates and (poly)cyanoacetates, and a polyaldehyde crosslinker, such as terephthalaldehyde. Such systems are described, for example, in Urankar et al., Polym. Prepr. (1994), 35, 933.

The components of the system react with one another under base catalysis at room temperature to form a crosslinked coating system which is suitable for a large number of applications. Because of its already good weathering stability it is also suitable, for example, for exterior applications and can where necessary be further stabilized by UV absorbers and other light stabilizers.

Further suitable components in the compositions include epoxy systems. Suitable epoxy resins are described above in connection with the cationically curable systems.

The curable component may also comprise compounds which are converted into a different form by exposure to bases. These are, for example, compounds which under base catalysis alter their solubility in suitable solvents, by elimination of protective groups, for example. Examples are chemically amplified photoresist formulations which react under base catalysis, as described, for example, by Leung in Polym. Mat. Sci. Eng. 1993, 68, 30. Examples for basically curable components as well as the corresponding initiator compounds are to be found in WO 98/32756, WO 98/38195, WO 98/41524, EP 898202, WO 00/10964, EP 1243632, WO 03/33500, WO 97/31033.

The compositions contain the photoinitiator in an amount, for example, of from 0.01 to 20% by weight, preferably from 0.01 to 10% by weight, based on the curable component.

In addition, the photopolymerizable mixtures may include various customary additives known to the person skilled in the art, e.g. thermal inhibitors, fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibres of other natural products, synthetic fibres, plasticizers, lubricants, emulsifiers, pigments, rheological additives, catalysts, levelling assistants, optical brighteners, flameproofing agents, antistatics, blowing agents. In addition to the additives indicated above it is also possible for additional coinitiators or sensitizers to be present. Examples are given above.

The formulations which cure upon the action of a base comprise a base-releasing compound. As photolatent bases there come into consideration, for example, capped amine compounds, for example generally the photolatent bases known in the art. Examples are compounds of the classes: o-nitrobenzyloxycarbonylamines, 3,5-dimethoxy-α,α-dimethylbenzyloxycarbonylamines, benzoin carbamates, derivatives of anilides, photolatent guanidines, generally photolatent tertiary amines, for example ammonium salts of α-ketocarboxylic acids, or other carboxylates, benzhydrylammonium salts, N-(benzophenonylmethyl)-tri-N-alkylammonium triphenylalkyl borates, photolatent bases based on metal complexes, e.g. cobalt amine complexes, tungsten and chromium pyridinium pentacarbonyl complexes, anion-generating photoinitators based on metals, such as chromium and cobalt complexes "Reinecke salts" or metalloporphyrins. Examples thereof are published in J. V. Crivello, K. Dietliker "Photoinitiators for Free Radical, Cationic & Anionic Photopolymerisation", Vol. III of "Chemistry & Technology of UV & EB Formulation for Coatings, Inks & Paints", 2nd Ed., J. Wiley and Sons/SITA Technology (London), 1998.

Suitable compounds are for example disclosed in WO 98/32756, WO 98/38195, WO 98/41524, EP 898202, WO 00/10964, EP 1243632, WO 03/33500, WO 97/31033.

The coating used in process step d2) also may be a radically opr cationically crosslinking formulation as well as formulation which is cured upon the action of a base. Said formulations may for example cure by drying or thermally, optionally with corresponding thermal initiators being present. The person skilled in the art is familiar with suitable compositions. d2) is preferably a printing ink.

Such printing inks are known to the person skilled in the art, are used widely in the art and are described in the literature.

They are, for example, pigmented printing inks and printing inks coloured with dyes.

A printing ink is, for example, a liquid or paste-form dispersion that comprises colorants (pigments or dyes), binders and also optionally solvents and/or optionally water and additives. In a liquid printing ink, the binder and, if applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks.

Suitable pigments, like the printing ink formulations customary in the art, are generally known and widely described.

Printing inks comprise pigments advantageously in a concentration of, for example, from 0.01 to 40% by weight, preferably from 1 to 25% by weight, especially from 5 to 10% by weight, based on the total weight of the printing ink.

The printing inks can be used, for example, for intaglio printing, flexographic printing, screen printing, offset printing, lithography or continuous or dropwise ink-jet printing on material pre-treated in accordance with the process of the invention using generally known formulations, for example in publishing, packaging or shipping, in logistics, in advertising, in security printing or in the field of office equipment.

Suitable printing inks are both solvent-based printing inks and water-based printing inks.

Of interest are, for example, printing inks based on aqueous acrylate. Such inks are to be understood as including polymers or copolymers that are obtained by polymerisation of at least one monomer containing a group

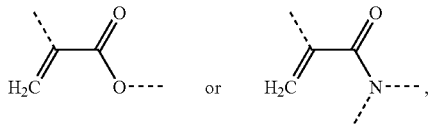

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclo, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations.

For intaglio or flexographic printing, a printing ink is usually prepared by dilution of a printing ink concentrate and can then be used in accordance with methods known per se.

The printing inks may, for example, also comprise alkyd systems that dry oxidatively.

The printing inks are dried in a known manner customary in the art, optionally with heating of the coating.

A suitable aqueous printing ink composition comprises, for example, a pigment or a combination of pigments, a dispersant and a binder.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids.

The arylsulfonic acid/formaldehyde condensation products are obtainable, for example, by sulfonation of aromatic compounds, such as naphthalene itself or naphthalene-containing mixtures, and subsequent condensation of the resulting arylsulfonic acids with formaldehyde. Such dispersants are known and are described, for example, in U.S. Pat. No. 5,186,846 und DE-A-197 27 767. Suitable oxalkylated phenols are likewise known and are described, for example, in U.S. Pat. No. 4,218,218 und DE-A-197 27 767. Suitable non-ionic dispersants are, for example, alkylene oxide adducts, polymerisation products of vinylpyrrolidone, vinyl acetate or vinyl alcohol and co-or ter-polymers of vinyl pyrrolidone with vinyl acetate and/or vinyl alcohol.

It is also possible, for example, to use polymeric acids which act both as dispersants and as binders.

Examples of suitable binder components that may be mentioned include acrylate-group-containing, vinyl-group-containing and/or epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP-A-704 469, EP-A-12 339). Furthermore, in order to obtain the desired viscosity the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary especially for (aqueous) ink-jet inks and in the printing and coating industries, for example preservatives (such as glutardialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally ≦1% by weight, based on the weight of the preparation.

Printing inks suitable in process step d2) include, for example, those comprising a dye (with a total content of dyes of e.g. from 1 to 35% by weight, based on the total weight of the ink). Dyes suitable for colouring such printing inks are known to the person skilled in the art and are widely available commercially, e.g. from Ciba Spezialitätenchemie AG, Basel.

Such printing inks may comprise organic solvents, e.g. water-miscible organic solvents, for example $C_1$-$C_4$alcohols, amides, ketones or ketone alcohols, ethers, nitrogen-containing heterocyclic compounds, polyalkylene glycols, $C_2$-$C_6$alkylene glycols and thioglycols, further polyols, e.g. glycerol and $C_1$-$C_4$alkyl ethers of polyhydric alcohols, usually in an amount of from 2 to 30% by weight, based on the total weight of the printing ink.

The printing inks may also, for example, comprise solubilisers, e.g. ε-caprolactam.

The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 4 to 9, especially from 5 to 8.5.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria.

Such additives are usually used in amounts of from 0.01 to 1% by weight, based on the total weight of the printing ink.

The printing inks may also be prepared in customary manner by mixing the individual components together, for example in the desired amount of water.

As already mentioned, depending upon the nature of the use, it may be necessary for e.g. the viscosity or other physical properties of the printing ink, especially those properties which influence the affinity of the printing ink for the substrate in question, to be adapted accordingly.

The printing inks are also suitable, for example, for use in recording systems of the kind in which a printing ink is expressed from a small opening in the form of droplets which are directed towards a substrate on which an image is formed. Suitable substrates are, for example, textile fibre materials, paper, plastics or aluminium foils pretreated by the process according to the invention. Suitable recording systems are e.g. commercially available ink-jet printers.

Preference is given to printing processes in which aqueous printing inks are used.

Examples for coatings according to d3) are metals, half-metals or metal oxides, for example deposited from the gas phase.

Examples for metals, half-metals and metal oxides to be deposited on the pre-treated substrate after the pre-treatment are the following: zinc, copper, nickel, gold, silver, platinum, palladium, chromium, molybdenum, aluminum, iron, titanium. Preferred are gold, silver, chromium, molybdenum, aluminum or copper, especially aluminum and copper. Interesting further are the following half-metals and metal oxides: aluminum oxide, chromium oxide, iron oxide, copper oxide and silicon oxide.

Preferred are gold, Silver, chromium, molybdenum, aluminum or copper.

The metals, half-metals or metal oxides are evaporated under vacuum conditions and deposited onto the substrate which is pretreated with the photoinitiator layer. This deposition may take place while irradiating with electromagnetic radiation. On the other hand, it is possible to carry out the irradiation after the deposition of the metal. The pot-temperatures for the deposition step depend on the metal which is used and preferably are for example in the range from 300 to 2000° C., in particular in the range from 800 to 1800° C.

The UV radiation during the deposition step can for example be produced by an anodic light arc, while for the UV radiation after the deposition the usual lamps as described above are also suitable.

Preferably, an irradiation with electromagnetic radiation is carried out in step d3), either during the deposition of the metal, half-metal or metal oxide or after the deposition.

The substrates coated with the metals are for example suitable as diffusion inhibiting layers, for electromagnetic shields or they can be used as decorative elements, for decorative foils, or for foils used for packaging, for example, for food packaging.

Subject of the invention also is a strongly adherent coating obtained by any process as described above.

The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

Example 1

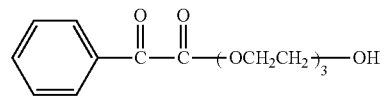

25.00 g (0.153 mol) Methylphenylglyoxalate are mixed with 132.84 g (0.809 mol) of triethyleneglycol and 0.26 g (0.0039 mol) of lithium acetate. The mixture is stirred overnight at 75° C., where the methanol is separated via distillation. The reaction mixture is cooled and poured on 100 ml water. The aqueous solution is then extracted with ethyl acetate. The organic phase is dried over MgSO$_4$, filtrated and evaporated. The product is purified by column chromatography and obtained as yellowish oil. $^1$H-NMR data (ppm, in CDCl$_3$): 8.03 2H d, 7.65 1H d×d, 7.53 2H d×d, 4.55 2H d×d, 3.82 2H d×d, 3.68 6H m, 3.61 2H d×d, 2.60 1H S.

Example 2

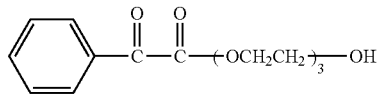

The compound of example 2 is synthesized according to the compound of example 1 using diethyleneglycol instead of triethyleneglycol. The compound is obtained as yellowish oil. $^1$H-NMR data (ppm, in CDCl$_3$): 8.02 2H d, 7.66 1H d×d, 7.53 2H d×d, 4.55 2H d×d, 3.85 2H d×d, 3.73 2H d×d, 3.63 2H d×d, 2.78 1H s.

Example 3

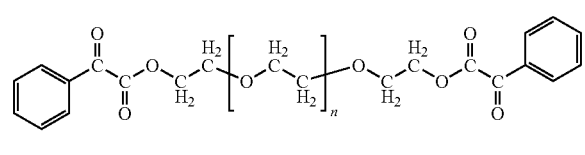

n = 11-12

The compound of example 3 is prepared by transesterification according to the compound of example 1, but with a ratio of 2 equivalents of methylphenylglyoxalate to 1 equivalent of polyethyleneglycol 600 (PEG600). The compound is obtained as yellowish oil. $^1$H-NMR data (ppm, in CDCl$_3$): 8.01 4H d, 7.65 2H d×d, 7.50 4H d×d, 4.53 4H d×d, 3.81 4H d×d, 3.69-3.62 44H m.

Example 4

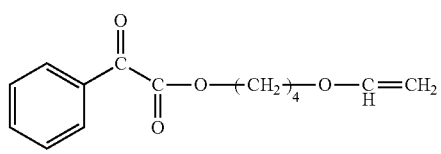

21.25 g (0.129 mol) of methylphenylglyoxalate, 22.55 g (0.194 mol) of 1,4-butanediol-monovinylether and 0.22 g (0.003 mol) of lithium acetate are mixed together and heated to 80° C. overnight. The reaction mixture is then cooled to room temperature and poured on water. The aqueous phase is extracted with ethyl acetate, and the organic phase is dried over MgSO$_4$, filtered and evaporated. The product is purified by column chromatography and obtained as yellowish oil. $^1$H-NMR data (ppm, in CDCl$_3$): 8.01 2H d, 7.67 1H d×d, 7.52 2H d×d, 6.46 1H d×d, 4.42 2H t, 4.18 1H d, 3.98 1H d, 3.73 2H t, 1.93-1.77 4H m.

Example 5

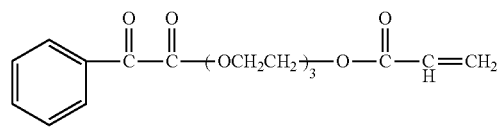

10.00 g (0.035 mol) of the triethyleneglycolester of example 1 are dissolved together with 4.30 g (0.042 mol) of triethylamine in 5 ml of dimethylformamide. The mixture is stirred at room temperature and 3.52 g (0.039 mol) acrylic acid chloride are added slowly. The product is treated with water, and the aqueous solution is then extracted with ethylacetate. The organic phase is dried over MgSO$_4$, filtered and evaporated. The product is purified by column chromatography and obtained as yellowish oil. $^1$H-NMR data (ppm, in CDCl$_3$): 8.03 2H d, 7.65 1H d×d, 7.50 2H d×d, 6.41 1H d, 6.13 1H d×d, 5.82 1H d, 4.53 2H d×d, 4.30 2H d×d, 3.83 2H d×d, 3.75-3.65 6H m.

Example 6

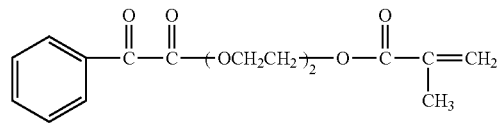

The compound of example 6 is prepared by reacting the compound of example 2 with methacrylic acid chloride according to example 5. The compound is obtained as yellowish oil. $^1$H-NMR data (ppm, in CDCl$_3$): 8.02 2H d, 7.63 1H d×d, 7.52 2H d×d, 6.09 1H s, 5.52 1H s, 4.55 2H d×d, 4.31 2H d×d, 3.85 2H d×d, 3.75 2H d×d, 1.91 3H s.

Example 7

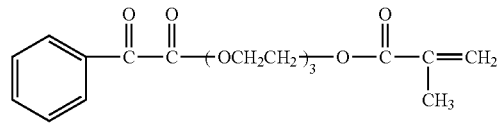

The compound of example 7 is made from the compound of example 1 according to the compound of example 5 using methacrylic acid chloride instead of acrylic acid chloride. The compound is obtained as yellowish oil. $^1$H-NMR data (ppm, in CDCl$_3$): 8.02 2H d, 7.65 1H dxd, 7.53 2H dxd, 6.08 1H s, 5.51 1H s, 4.52 2H dxd, 4.27 2H dxd, 3.81 2H dxd, 3.74-3.36 6H m, 1.92 3H s.

Example 8

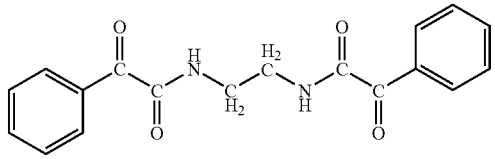 [SMILES: O=C(NCCNC(=O)C(=O)c1ccccc1)C(=O)c1ccccc1]

4.00 g (0.024 mol) of Methylphenylglyoxalate are mixed with 0.72 g (0.012 mol) of ethylenediamine in 10 ml of dimethylformamide and heated to 100° C. for 2 hours. The mixture is poured on water, and the precipitate filtered and washed with water and dried. The product is obtained as yellowish powder. $^1$H-NMR data (ppm, in DMSO-d$_6$): 9.05 2H s, 8.02 4H d, 7.72 2H dxd, 7.54 4H dxd, 3.46 4H d.

Example 9

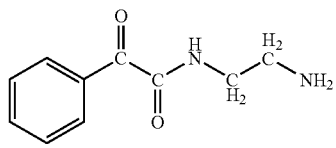 [SMILES: NCCNC(=O)C(=O)c1ccccc1]

The compound of example 9 is synthesized in analogy to the compound of example 8 with higher amounts of ethylenediamine. The compound is obtained as yellowish powder. $^1$H-NMR data (ppm, in DMSO-d$_6$): 8.54 1H s, 7.84 2H d, 7.47-7.30 3H m, 3.79 2H t, 3.33 2H m, 2.50 2H s.

Example 10

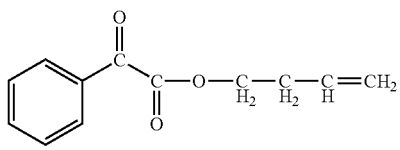

10.00 g (0.066 mol) Phenylglyoxylic acid are mixed with 14.4 g (0.199 mol) of 3-buten-1-ol and 0.4 g (0.002 mol) of para-toluenesulfonic acid in 100 ml toluene. The reaction mixture is refluxed and the water is separated by a Dean-Starck-distillation. The reaction mixture is then cooled to room temperature, poured on water and the aqueous phase is extracted with ethyl actetate. The organic phase is dried over MgSO$_4$ and evaporated. The product is purified by column chromatography and obtained as yellowish oil. $^1$H-NMR data (ppm, in CDCl$_3$): 8.03 2H d, 7.66 1H dxd, 7.53 2H dxd, 5.91-5.78 1H m, 5.24-5.12 2H m, 4.46 2H t, 2.57 2H dxt.

Example 11

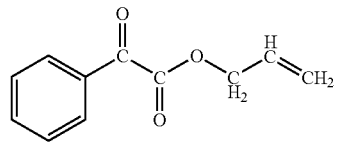

The compound of example 11 is synthesized according to the compound of example 10 with allylic alcohol instead of 3-buten-1-ol. The compound is obtained as yellowish oil. $^1$H-NMR data (ppm, in CDCl$_3$): 8.02 2H d, 7.63 1H dxd, 7.48 2H dxd, 6.05-5.94 1H m, 5.45 1H d, 5.32 1H d, 4.87 2H d.

Example 12

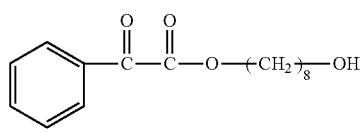

25.00 g (0.166 mol) Benzoylformic acid is mixed with 24.35 g (0.166 mol) of 1,8-octanediol in 100 ml of toluene. 0.095 g (0.0005 mol) para-toluenesulfonic acid is added, and the mixture is refluxed with a Dean-Starck to separate the water for 1 hour. The reaction mixture is cooled to room temperature and poured on to water. The aqueous mixture is extracted with ethyl acetate. The organic phase is dried over MgSO$_4$ and evaporated. The product is purified by column chromatography and obtained as yellowish oil. $^1$H-NMR data (ppm, in CDCl$_3$): 8.02 2H d, 7.67 1H dxd, 7.52 2H dxd, 4.39 2H t, 3.63 2H t, 1.82-1.27 12H m.

Example 13

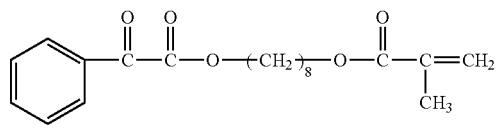

The compound of example 13 is synthesized from the compound of example 12 according to the method of example 7. The compound is obtained as yellowish oil. $^1$H-NMR data (ppm, in CDCl$_3$): 8.02 2H d, 7.66 1H dxd, 7.53 2H dxd, 6.12 1H s, 5.56 1H s, 4.41 2H t, 4.12 2H t, 1.96 3H s, 1.83-1.38 12H m.

Example 14

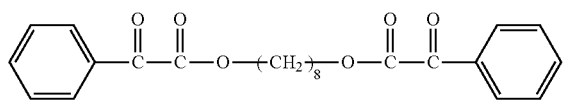

The compound of example 14 is synthesized according to example 12, but with an excess of benzoylformic acid compared to the di-alcohol. The product is purified by column chromatography and obtained as yellowish oil. $^1$H-NMR data (ppm, in CDCl$_3$): 8.02 4H d, 7.65 2H dxd, 7.53 4H dxd, 4.38 4H t, 1.82-1.73 4H m, 1.44-1.20 8H m.

Example 15

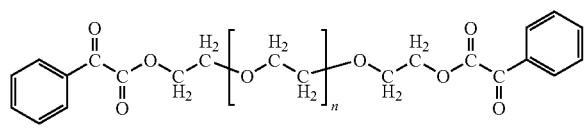

n = 20-21

The compound of example 15 is obtained by transesterification of two equivalents of methylphenylglyoxalate and 1 equivalent of polyethyleneglycol 1000. The product is obtained as yellowish wax. $^1$H-NMR data (ppm, in CDCl$_3$): 8.00 4H d, 7.78 2H dxd, 7.63 4H dxd, 4.52 4H dxd, 3.74 4H dxd, 3.60-3.41 80H m.

Example 16

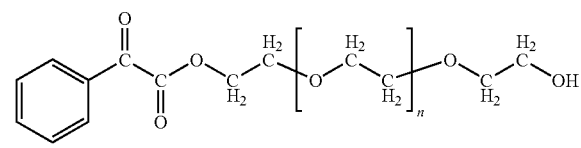

n = 4-5

The compound of example 16 is synthesized by transesterification according to example 3, with polyethyleneglycol 300 instead of polyethyleneglycol 600 and the molecular ratio of methylphenylglyoxalate to polyethyleneglycol 300 is 1:1. The product is obtained as yellowish oil. $^1$H-NMR data (ppm, in CDCl$_3$): 8.02 2H d, 7.61 1H dxd, 7.51 2H dxd, 4.51 2H dxd, 3.77 2H dxd, 3.70-3.55 11H m.

Example 17

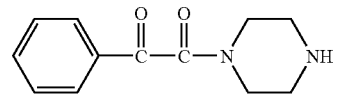

The compound of example 17 is synthesized according to the compound of example 9, with piperazine instead of ethylenediamine. The product is obtained as yellowish oil. $^1$H-NMR data (ppm, in DMSO-d$_6$): 7.90 2H d, 7.74 1H dxd, 7.61 2H dxd, 3.57 2H m, 3.17 2H m, 2.76 2H m, 2.61 2H m.

Example 18

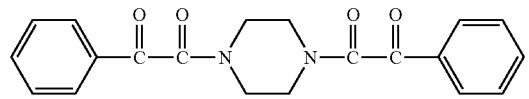

The compound of example 18 is synthesized according to the compound of example 8, with piperazine instead of ethylenediamine. The product is obtained as white powder. $^1$H-NMR data (ppm, in DMSO-d$_6$): two isomers visible on NMR time scale 7.97-7.89 4H m, 7.80-7.76 2H m, 7.64-7.59 4H m, 3.82 2H s, 3.64 2H m, 3.49 2H m, 3.30 2H s.

Example 19

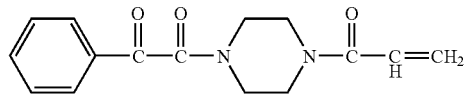

0.42 g of compound 17 is diluted together with 0.41 g of triethylamine and 0.0005 g hydroquinonemonomethylether in 20 ml of dimethylformamide, and the solution is stirred at 25° C. Then 0.35 g of acrylic-acid-chloride is added dropwise to this solution. A precipitate forms. After 2 hours of reaction, 50 ml water and 50 ml methylenechloride are added. The phases are separated and the organic phase is then washed three times with 50 ml of water. The solvent is dried and evaporated. The product is purified over silica gel column chromatography. The product is obtained as yellowish oil. $^1$H-NMR data (ppm, in DMSO-d$_6$): 7.92 2H d, 7.76 1H dxd, 7.63 2H dxd, 6.85-6.68 1H m, 6.13 1H d, 5.72 1H m, 3.72-3.65 4H m, 3.53 2H m, 3.31 2H m.

Example 20

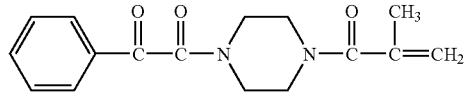

The compound of example 20 is synthesized according to example 19, with methacrylicacid chloride instead of acrylicacid chloride. The product is obtained as yellowish resin. ¹H-NMR data (ppm, in DMSO-d₆): 7.92 2H d, 7.78 1H d×d, 7.63 2H d×d, 5.22 1H s, 5.03 1H s, 3.69-3.63 4H m, 3.48-3.44 2H m, 3.31 2H m, 1.86 3H s.

Example 21

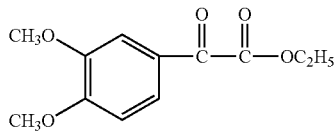

81.82 g of aluminumchloride are suspended in 1 liter of methylenechloride, and the mixture is cooled to 0° C. 57.10 g of veratrole and 57.58 g of oxalicacid-monoethylester-chloride are dissolved in 550 ml of methylenechloride, and the mixture is slowly added to the first suspension upon stirring. The reaction mixture is then stirred for a further 3 hours and poured onto 3 kg of ice. Once the ice is molten, the phases are separated. The organic phase is washed two times with water and then dried over MgSO₄. The solvent is evaporated and the product is chromatographed over silica gel. The product is obtained as yellow oil. ¹H-NMR data (ppm, in CDCl₃): 7.61 1H d, 7.54 1H s, 6.91 1H d, 4.42 2H q, 3.95 3H s, 3.92 3H s, 1.40 3H t.

Example 22

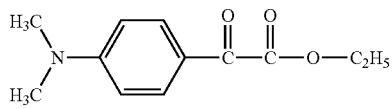

139.47 g of titaniumtetrachloride are suspended in 1 liter methylenechloride, and the mixture is cooled to 0° C. 60.00 g of N,N-dimethylaniline and 68.98 g of oxalicacid-monoethylester-chloride are dissolved in 400 ml of methylenechloride, and the mixture is slowly added to the first suspension upon stirring. The reaction mixture is then stirred for a further 1 hour and poured onto 2 liters of ice/water mixture. Once the ice is molten, the phases are separated. The organic phase is washed two times with water and then dried over MgSO₄. The product is recrystallized form ethanol and is obtained as yellow powder. ¹H-NMR data (ppm, in CDCl₃): 7.92 2H d, 6.66 2H d, 4.43 2H q, 3.12 6H s, 1.43 3H t.

Example 23

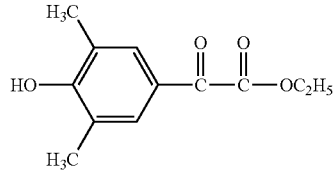 [SMILES: CCOC(=O)C(=O)c1cc(C)c(O)c(C)c1]

The compound of example 23 is synthesized according to the compound of example 21, with 2,6-dimethylphenol instead of veratrole. The product is obtained as a yellow powder. ¹H-NMR data (ppm, in CDCl₃): 7.69 2H s, 5.69 1H s, 4.45 2H q, 2.30 6H s, 1.43 3H t.

Example 24

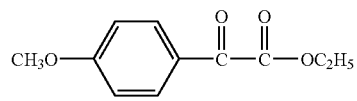

The compound of example 24 is synthesized according to the compound of example 21, with anisole instead of veratrole. The product is obtained as yellow oil. ¹H-NMR data (ppm, in CDCl₃): 8.00 2H d, 6.97 2H d, 4.43 2H q, 3.89 3H s, 1.42 3H t.

Example 25

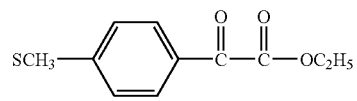

The compound of example 25 is synthesized according to example 21, with thioanisole instead of veratrole. The product is obtained as yellow oil. ¹H-NMR data (ppm, in CDCl₃): 7.90 2H d, 7.25 2H d, 4.43 2H q, 2.51 3H s, 1.40 3H t.

Example 26

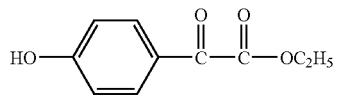

The compound of example 26 is synthesized according to the compound of example 21, with phenol instead of veratrole. The product is chromatographed over silicagel and obtained as yellowish powder. ¹H-NMR data (ppm, in CDCl₃): 7.99 2H d, 6.95 2H d, 6.26 1H d, 4.46 2H q, 1.44 3H t.

Example 27

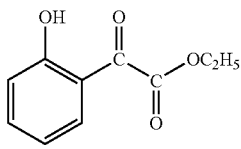 [SMILES: CCOC(=O)C(=O)c1ccccc1O]

The compound of example 27 is synthesized according to the compound of example 21, with phenol instead of veratrole. The product is chromatographed over silicagel and obtained as yellow oil. ¹H-NMR data (ppm, in CDCl₃): 11.23 1H s, 7.72 1H d, 7.60 1H d×d, 7.05 1H d, 6.98 1H d×d, 4.47 2H q, 1.46 3H t.

¹H-NMR data (ppm, in CDCl₃): 7.66 2H s, 6.13-6.00 1H m, 5.40 1H d, 5.25 1H d, 4.41 2H q, 4.33 2H d, 2.30 6H s, 1.40 3H t.

Example 28

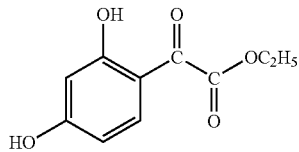 [SMILES: CCOC(=O)C(=O)c1ccc(O)cc1O]

The compound of example 28 is synthesized according to the compound of example 21, with resorcinol instead of veratrole. The resorcinol is dissolved in a 1:1 mixture of methylenechloride/sulfolane for better solubility. The product is obtained as greenish solid.

¹H-NMR data (ppm, in DMSO-d₆): 10.97 1H s, 10.79 1H s, 7.62 1H d, 6.43 1H d, 6.37 1H s, 4.28 2H q, 1.28 3H t.

Example 31

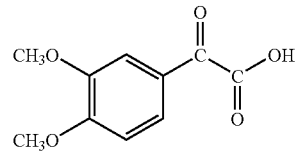

45 g of compound 21 are added slowly to a solution of 9 g NaOH in 100 ml of water at 50° C. The ester saponifies and compound 31 is then precipitated by the addition of concentrated HCl. The product is extracted with ethylacetate, the organic phase is dried over MgSO₄ and evaporated. The product is obtained as yellow powder. ¹H-NMR data (ppm, in DMSO-d₆): 7.55 1H d, 7.43 1H s, 7.16 1H d, 3.89 3H s, 3.84 3H s.

Example 29

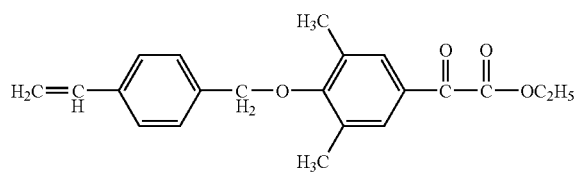 [SMILES: C=Cc1ccc(COc2c(C)cc(C(=O)C(=O)OCC)cc2C)cc1]

13.13 g of compound 23 and 19.42 g of sodium carbonate are added to 20 ml of dimethylformamide and the mixture is heated to 100° C. 27.06 g of p-chloromethylstyrene is added to the mixture and the mixture is stirred for 2 hours at 100° C. Then the mixture is cooled to room temperature and is poured on an ice-water mixture. The product is extracted with ethylacetate and purified by column chromatography over silica gel. The product is obtained as yellowish powder. ¹H-NMR data (ppm, in CDCl₃): 7.75 2H s, 7.48 2H d, 7.20 2H d, 6.77 1H d×d, 5.82 1H d, 5.32 1H d, 4.89 2H s, 4.48 2H q, 2.36 6H s, 1.46 3H t.

Example 32

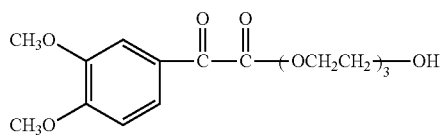

The compound of example 32 is synthesized according to the compound of example 1, starting from compound 21. The product is obtained as yellow oil. ¹H-NMR data (ppm, in CDCl₃): 7.65 1H d, 7.55 1H s, 6.92 1H d, 4.53 2H d×d, 3.96 2H s, 3.93 3H s, 3.83 2H d×d, 3.70-3.64 6H m, 3.58 2H d×d, 2.49 1H s.

Example 30

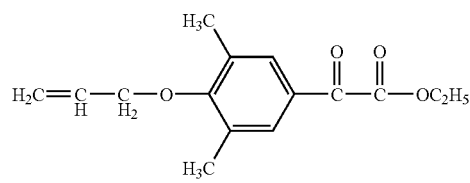

The compound of example 30 is synthesized according to the compound of example 29, starting from compound 23 and allylbromide. The product is obtained as a yellowish oil.

Example 33

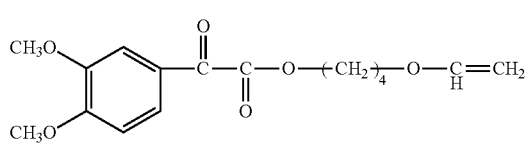

The compound of example 33 is synthesized according to example 4, starting from compound 21. The product is obtained as yellow oil. ¹H-NMR data (ppm, in CDCl₃): 7.60

1H d, 7.53 1H s, 6.90 1H d, 6.43 1H dxd, 4.41 2H t, 4.15 1H d, 3.97 1H d, 3.95 3H s, 3.92 3H s, 3.71 2H t, 1.93-1.73 4H m.

Example 34

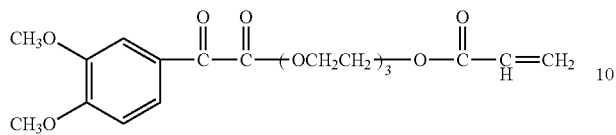

The compound of example 34 is synthesized according to the compound of example 5, starting from compound 32. The product is obtained as yellow oil. $^1$H-NMR data (ppm, in CDCl$_3$): 7.68 1H d, 7.58 1H s, 6.94 1H d, 6.43 1H d, 6.15 1H dxd, 5.84 1H d, 4.55 2H dxd, 4.32 2H dxd, 3.99 3H s, 3.96 3H s, 3.86 2H dxd, 3.77 2H dxd, 3.75-3.67 4H m.

Example 35

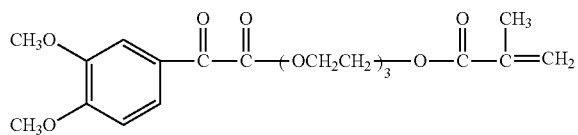

The compound of example 35 is synthesized according to example 7, starting from compound 32. The product is obtained as yellow oil. $^1$H-NMR data (ppm, in CDCl$_3$): 7.67 1H d, 7.57 1H s, 6.94 1H d, 6.13 1H s, 5.58 1H s, 4.54 2H dxd, 4.30 2H dxd, 3.99 3H s, 3.96 3H s, 3.85 2H dxd, 3.75 2H dxd, 3.72-3.67 4H m, 1.95 3H s.

Example 36

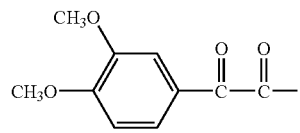

n = 11-12

The compound of example 36 is prepared according to the compound of example 3, starting from compound 21. The compound is obtained as yellow oil. $^1$H-NMR data (ppm, in CDCl$_3$): 7.65 2H d, 7.55 2H s, 6.93 2H d, 4.53 4H dxd, 3.97 6H s, 3.94 6H s, 3.82 4H dxd, 3.70-3.63 44H m.

Example 37

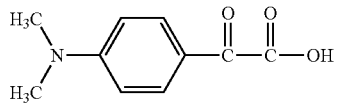

The compound of example 37 is synthesized according to the compound of example 31 starting from compound 22. The product is obtained as yellow powder. $^1$H-NMR data (ppm, in DMSO-d$_6$): 7.72 2H d, 6.78 2H d, 3.06 6H s.

Example 38

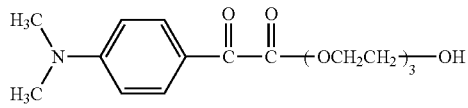

The compound of example 38 is synthesized according to example 1, starting from compound 22. The product is obtained as orange oil. $^1$H-NMR data (ppm, in CDCl$_3$): 7.89 2H d, 6.63 2H d, 4.49 2H dxd, 3.81 2H dxd, 3.71-3.63 6H m, 3.59-3.56 2H m, 3.07 6H s, 2.64 1H s.

Example 39

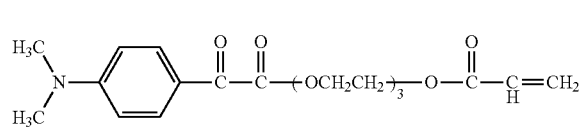

The compound of example 39 is synthesized according to the compound of example 5, starting from compound 38. The product is obtained as brownish oil. $^1$H-NMR data (ppm, in CDCl$_3$): 7.89 2H d, 6.65 2H d, 6.42 1H d, 6.14 1H dxd, 5.83 1H d, 4.51 2H dxd, 4.29 2H dxd, 3.83 2H dxd, 3.74 2H dxd, 3.73-3.66 4H m, 3.10 6H s.

Example 40

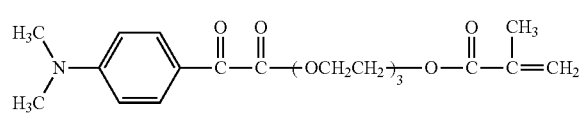

The compound of example 40 is synthesized according to the compound of example 7, starting from compound 38. The product is obtained as yellow oil. $^1$H-NMR data (ppm, in CDCl$_3$): 7.91 2H d, 6.66 2H d, 6.13 1H s, 5.58 1H s, 4.52 2H dxd, 4.29 2H dxd, 3.84 2H dxd, 3.76 2H dxd, 3.72-3.67 4H m, 3.12 6H s, 1.95 3H s.

Example 41

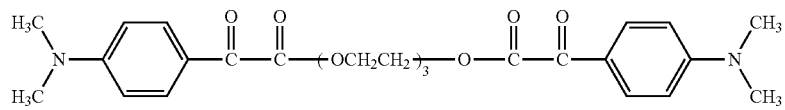

The compound of example 41 is synthesized according to the compound of example 1 with a ratio of 2:1 for compound 22 against triethyleneglycol. The product is obtained as yellow powder. $^1$H-NMR data (ppm, in CDCl$_3$): 7.90 4H d, 6.65 4H d, 4.50 4H t, 3.83 4H t, 3.71 4H s, 3.11 12H s.

Example 42

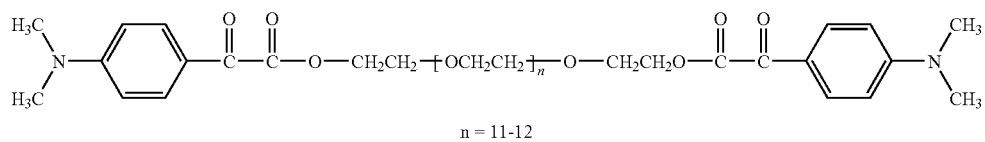

n = 11-12

The compound of example 42 is prepared according to the compound of example 3, starting from compound 22. The compound is obtained as orange oil. $^1$H-NMR data (ppm, in CDCl$_3$): 7.90 4H d, 6.66 4H d, 4.51 4H d×d, 3.83 4H d×d, 3.71-3.64 44H m, 3.11 12H s.

Example 43

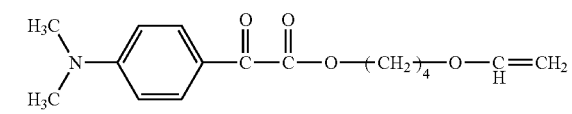

The compound of example 43 is synthesized according to example 4, starting from compound 22. The product is obtained as yellow oil. $^1$H-NMR data (ppm, in CDCl$_3$): 7.87 2H d, 6.65 2H d, 6.45 1H d×d, 4.38 2H t, 4.16 1H d, 3.98 1H d, 3.71 2H t, 3.07 6H s, 1.91-1.73 4H m.

Example 44

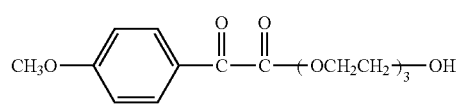

The compound of example 44 is synthesized according to the compound of example 1, starting from compound 24. The product is obtained as yellowish oil. $^1$H-NMR data (ppm, in CDCl$_3$): 8.00 2H d, 6.98 2H d, 4.52 2H d×d, 3.88 3H s, 3.82 2H d×d, 3.71-3.65 6H m, 3.62-3.57 2H d×d, 3.05 1H s.

Example 45

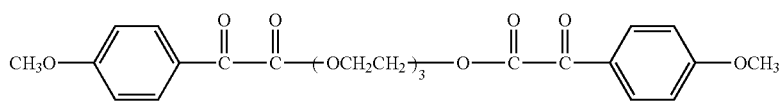

The compound of example 45 is synthesized according to the compound of example 41, starting from compound 24. The product is obtained as brownish oil. $^1$H-NMR data (ppm, in CDCl$_3$): 7.97 4H d, 6.95 4H d, 4.50 4H d×d, 3.86 6H s, 3.81 4H d×d, 3.66 4H s.

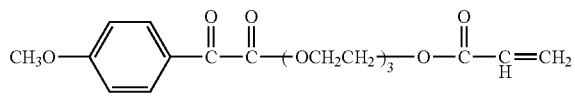

Example 46

The compound of example 46 is synthesized according to the compound of example 5, starting from compound 44. The product is obtained as yellowish oil. $^1$H-NMR data (ppm, in CDCl$_3$): 8.02 2H d, 6.97 2H d, 6.43 1H d, 6.15 1H d×d, 5.84 1H d, 4.54 2H d×d, 4.31 2H d×d, 3.91 3H s, 3.84 2H d×d, 3.75 2H d×d, 3.74-3.67 4H m.

Example 47

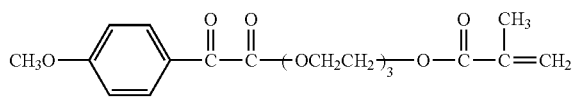

The compound of example 47 is synthesized according to the compound of example 7, starting from compound 44. The product is obtained as yellowish oil. $^1$H-NMR data (ppm, in CDCl$_3$): 8.01 2H d, 6.97 2H d, 6.12 1H s, 5.56 1H s, 4.53 2H d×d, 4.30 2H d×d, 3.89 3H s, 3.84 2H d×d, 3.74 2H d×d, 3.74-3.65 4H m, 1.95 3H s.

Example 48

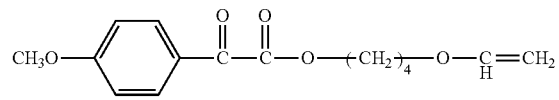

The compound of example 48 is synthesized according to the compound of example 4, starting from compound 24. The product is obtained as yellowish oil. $^1$H-NMR data (ppm, in CDCl$_3$): 8.01 2H d, 7.00 2H d, 6.48 1H d×d, 4.40 2H t, 4.16 1H d, 3.98 1H d, 3.92 3H s, 3.69 2H t, 1.77-1.66 4H m.

Example 49

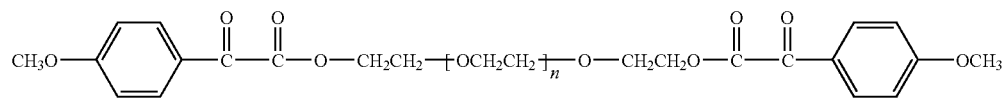

n = 11-12

The compound of example 49 is prepared according to the compound of example 3, starting from compound 24. The compound is obtained as orange oil. $^1$H-NMR data (ppm, in CDCl$_3$): 8.01 4H d, 6.96 4H d, 4.51 4H d×d, 3.88 6H s, 3.81 4H d×d, 3.72-3.57 44H m.

Example 50

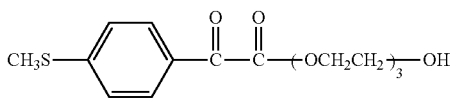

The compound of example 50 is synthesized according to the compound of example 1, starting from compound 25. The product is obtained as yellow oil. $^1$H-NMR data (ppm, in CDCl$_3$): 7.95 2H d, 7.30 2H d, 4.55 2H d×d, 3.84 2H d×d, 3.73-3.67 6H m, 3.60 2H d×d, 2.54 3H s, 2.36 1H s.

Example 51

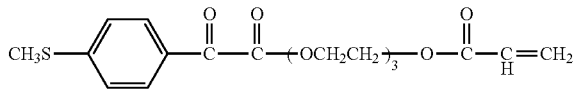

The compound of example 51 is synthesized according to the compound of example 5, starting from compound 50. The product is obtained as yellow oil. $^1$H-NMR data (ppm, in CDCl$_3$): 7.96 2H d, 7.29 2H d, 6.42 1H d, 6.18 1H d×d, 5.85 1H d, 4.55 2H d×d, 4.32 2H d×d, 3.85 2H d×d, 3.77 2H d×d, 3.75-3.68 4H m, 2.56 3H s.

Example 52

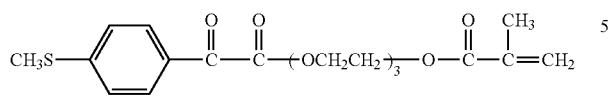

The compound of example 52 is synthesized according to the compound of example 7, starting from compound 50. The product is obtained as yellow oil. $^1$H-NMR data (ppm, in CDCl$_3$): 7.95 2H d, 7.29 2H d, 6.14 1H s, 5.58 1H s, 4.55 2H dxd, 4.32 2H dxd, 3.85 2H dxd, 3.76 2H dxd, 3.72-3.66 4H m, 2.55 3H s, 1.95 3H s.

Example 53

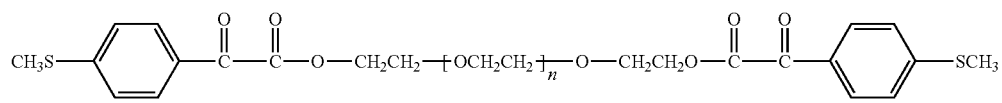

n = 11-12

The compound of example 53 is prepared according to the compound of example 3, starting from compound 25. The compound is obtained as orange oil. $^1$H-NMR data (ppm, in CDCl$_3$): 7.95 4H d, 7.29 4H d, 4.55 4H dxd, 3.84 4H dxd, 3.74-3.61 44H m, 2.55 6H s.

Example 54

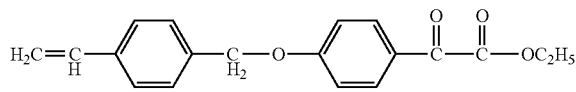

The compound of example 54 is synthesized according to the compound of example 29 from compound 26 and p-chloromethyl-styrene. The product is obtained as off-white solid. $^1$H-NMR data (ppm, in CDCl$_3$): 8.02 2H d, 7.46 2H d, 7.40 2H d, 7.07 2H d, 6.75 1H dxd, 5.79 1H d, 5.30 1H d, 5.17 2H s, 4.45 2H q, 1.44 3H t.

Example 55

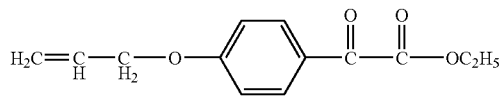

The compound of example 55 is synthesized according to the compound of example 29 from compound 26 and allyl-bromide. The product is obtained as yellowish oil. $^1$H-NMR data (ppm, in CDCl$_3$): 8.02 2H d, 6.99 2H d, 6.06 1H dxdxt, 5.44 1H d, 5.35 1H d, 4.65 2H d, 4.45 2H q, 1.44 3H t.

Example 56

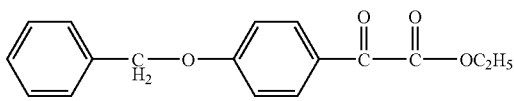 [SMILES: CCOC(=O)C(=O)c1ccc(OCc2ccccc2)cc1]

The compound of example 56 is synthesized according to the compound of example 29 from compound 26 and benzyl-bromide. The product is obtained as yellowish oil. $^1$H-NMR data (ppm, in CDCl$_3$): 8.03 2H d, 7.47-7.36 5H m, 7.06 2H d, 5.18 2H s, 4.45 2H q, 1.44 3H t.

Example 57

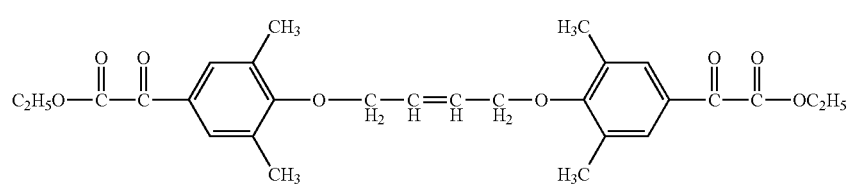

The compound of example 57 is synthesized according to the compound of example 29 from compound 23 and trans-1,4-dibromo-2-butene. The product is obtained as brownish powder.

$^1$H-NMR data (ppm, in $CDCl_3$): 7.67 4H s, 6.15 2H s, 4.48 4H s, 4.42 4H q, 2.30 12H s, 1.33 6H t.

Example 58

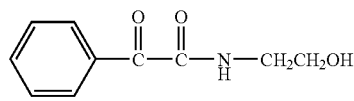

25.5 g (0.155 mol) of methyl-phenylglyoxalate and 10.43 g (0.171 mol) of ethanolamine is mixed and heated for 3 h at 100° C. The released methanol is distilled off during the reaction.

The reaction mixture is cooled to room temperature and poured into water. The water phase is extracted with ethyl acetate. After dryining and evaporation of the organic phase, the product is obtained as slightly brownish oil. $^1$H-NMR data (ppm, in $CDCl_3$): 8.23 2H d, 7.74 1H s, 7.61 1H t, 7.44 2H t, 3.76 2H t, 3.52 2H t, 3.34 1H s.

Example 59

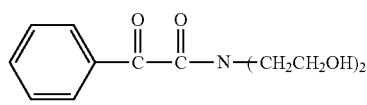

The compound of example 59 is synthesized from methyl-phenylglyoxalate and diethanolamine according to the method described for the compound of example 58 and isolated by column chromatography. The product is obtained as yellowish resin. $^1$H-NMR data of the main isomer (ppm, in $d_6$-DMSO): 7.53 2H d, 7.31 3H m, 7.16 1H s, 4.76 1H t, 4.27 1H t, 3.83 2H t, 3.55-3.21 5H m.

Example 60

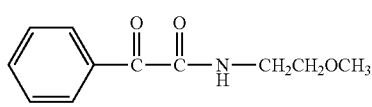

The compound of example 60 is synthesized according to the method described for compound of example 58 from methyl-phenylglyoxalate and 2-methoxy-ethylamine. The product is purified by column chromatography. The product is obtained as yellowish solid. $^1$H-NMR data (ppm, in $CDCl_3$): 8.34 2H d, 7.64 1H t, 7.50 2H t, 7.41 1H s, 3.63-3.56 4H m, 3.41 3H s.

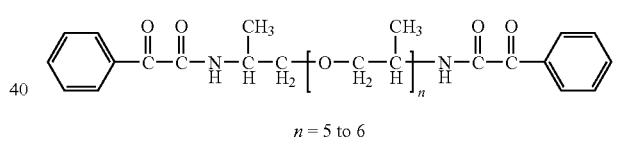

$n$ = approx. 9

Example 61

2.70 g (0.017 mol) of methylphenylglyoxalate and 10.00 g of Jeffamine XTJ-505 (product and registered trade mark of Huntsman Corporation) are mixed and heated for 6 hours at 100° C. A little excess of methylphenylglyoxalate is evaporated at high vacuum and the product is obtained as slightly brownish oil. $^1$H-NMR data (ppm, in $CDCl_3$): 8.29 t, 7.83 m, 7.68 d, 7.60 t, 7.49-7.28 m, 3.70-3.25 m, 1.30-1.05 m.

Example 62

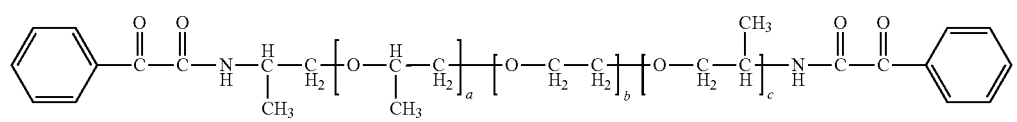

$n$ = 5 to 6

The compound of example 62 is synthesized according to the method described for the compound of example 61 from methylphenylglyoxalate and Jeffamine D-400 (product and registered trade mark of Huntsman Corporation). The product is obtained as brownish oil. $^1$H-NMR data (ppm, in $CDCl_3$): 8.30 t, 7.83 m, 7.68 d, 7.59 t, 7.49-7.18 m, 3.80-3.25 m, 1.35-1.05 m.

Example 63

The compound of example 63 is synthesized according to the method described for the compound of example 61 from methylphenylglyoxalate and Jeffamine XTJ-500 (product and registered trade mark of Huntsman Corporation). The product is obtained as brownish oil. $^1$H-NMR data (ppm, in CDCl$_3$): 8.28 t, 7.80 m, 7.70-7.63 m, 7.61-7.55 m, 7.48-7.17 m, 3.70-3.30 m, 1.30-1.00 m.

Example 64

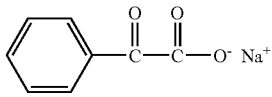

11.04 g (0.29 mol) of sodium hydroxide is dissolved in 50 ml of water, and 43.62 g (0.29 mol) phenylglyoxylic acid is added at room temperature. The water is evaporated. The product is obtained as yellowish solid. $^1$H-NMR data (ppm, in d$_6$-DMSO): 8.48 2H d, 7.56 1H t, 7.47 2H t.

Example 65

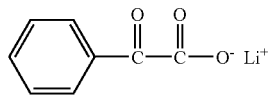

The compound of example 65 is synthesized according to the method described for the compound of example 64 from phenylglyoxylic acid and lithium hydroxide. The product is obtained as yellowish solid. $^1$H-NMR data (ppm, in d$_6$-DMSO): 8.47 2H d, 7.57 1H t, 7.47 2H t.

Example 66

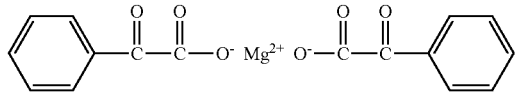

The compound of example 66 is synthesized according to the method described for the compound of example 64 from phenylglyoxylic acid and magnesium hydroxide. The product is obtained as white solid. $^1$H-NMR data (ppm, in D$_2$O): 7.86 4H d, 7.65 2H t, 7.52 4H t.

Example 67

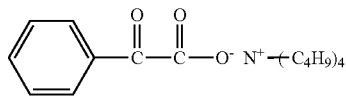

10.00 g (0.067 mol) of phenylglyoxylic acid, 21.47 g (0.067 mol) of tetrabutylammonium bromide and 5.41 g (0.133 mol) of sodium hydroxide are dissolved in 100 ml of water and the product is extracted with dichloromethane. The organic phase is washed with water and dried. The product is obtained as yellowish oil. $^1$H-NMR data (ppm, in CDCl$_3$): 7.99 2H d, 7.42 1H t, 7.33 2H t, 3.22 8H t, 1.59-1.51 8H m, 1.38-1.28 8H m, 0.90 12H t.

Example 68

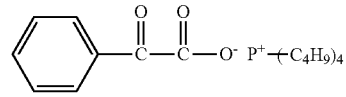

The compound of example 68 is synthesized according to the method described for the compound of example 67 from phenylglyoxylic acid, tetrabutylphosphonium bromide and sodium hydroxide. The product is obtained as yellowish solid. $^1$H-NMR data (ppm, in CDCl$_3$): 8.00 2H d, 7.45 1H t, 7.35 2H t, 2.35-2.28 8H m, 1.52-1.40 16H m, 0.90 12H t.

Example 69

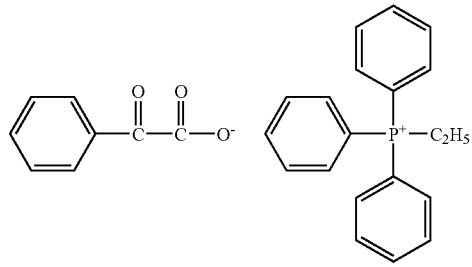 [SMILES: O=C([O-])C(=O)c1ccccc1 ; CC[P+](c1ccccc1)(c1ccccc1)c1ccccc1]

The compound of example 69 is synthesized according to the method described for the compound of example 67 from phenylglyoxylic acid, ethyltriphenylphosphonium bromide and sodium hydroxide. The product is obtained as yellowish solid. $^1$H-NMR data (ppm, in D$_2$O): 7.79-7.69 3H m, 7.63-7.52 16H m, 7.41 1H t, 3.19-3.07 2H txt, 1.24-1.10 3H d×t.

Example 70

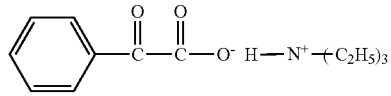

10.00 g (0.068 mol) of phenylglyoxylic acid and 6.88 g (0.068 mol) of triethylamine are dissolved in 10 ml of acetone at room temperature and the solvent is evaporated. The product is obtained as yellowish oil. $^1$H-NMR data (ppm, in CDCl$_3$): 10.00 1H b, 8.01 2H d, 7.51 1H t, 7.41 2H t, 3.09 6H q, 1.28 9H t.

Example 71

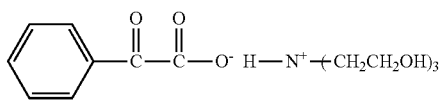

The compound of example 71 is synthesized according to the method described for the compound of example 70 from phenylglyoxylic acid and triethanolamine. The product is obtained as yellowish powder. $^1$H-NMR data (ppm, in D$_2$O): 7.88 2H d, 7.68 1H t, 7.53 2H t, 3.87 6H t, 3.38 6H t.

Example 72

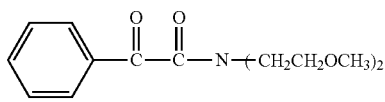

The compound of example 72 is synthesized according to the method described for the compound of example 58 from methyl-phenylglyoxalate and bis-(2-methoxy-ethyl)-amine.

The product is purified by column chromatography. The product is obtained as yellowish resin. $^1$H-NMR data (ppm, in CDCl$_3$): 8.05 2H d, 7.61 1H t, 7.48 2H t, 3.83 2H t, 3.72 2H t, 3.59 2H t, 3.47 2H t, 3.45 3H s, 3.17 3H s.

APPLICATION EXAMPLES

Example A1

Two different bisaxial oriented poylpropylene (BOPP) films and a polyethylene (PE) film are treated with corona (ceramic electrode; 0.8 mm distance to substrate; corona discharge 1×500 W at a belt speed of 3 m/min).

A 1% solution of a 1:1 molecular mixture of IRGACURE®754 and SARTOMER®259 in isoproanol is applied to the treated side of the films using a 4 μm wire bar.

IRGACURE®754, provided by Ciba Specialty Chemicals, is

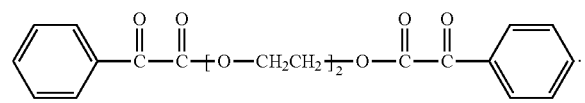

SARTOMER®259, provided by Sartomer Company, is

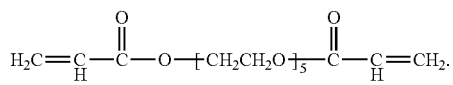

The samples are stored for a short time until the isopropanol has evaporated and the samples are dry. After drying the samples are irradiated using a UV processor with a mercury lamp with an output of 120 W/cm at a belt speed of 50 m/min.

A radiation-curable flexo cyan ink (Gemini flexo cyan, UFG 50080-408, provided by Akzo) is applied on the pretreated plastic film substrates in a thickness of 1.5 μm with a printing machine ("Prüfbau Probedruckmaschine"). The printed samples are cured in a UV processor with a mercury lamp and an output of 120 W/cm at a belt speed of 50 m/min.

The adhesive strength of the ink on the treated substrate is determined by the tape test: a Tesa EU tape is applied on cured surface. After one minute the tape is removed. The result of the adhesion is determined in a ranking between 0 and 5. A value "0" indicates that 0% of the ink is removed, while a value "5" indicates 100%, i.e. the complete, remove of the ink.

In the case of untreated samples [i.e. only steps a) and d) are performed] the ink is torn off completely (5).

With all three samples (BOPP and PE) according to the invention pretreated with a photoinitiator mixture [i.e. steps a) b) c) and d) are performed], no ink is removed (0).

Example A2

The procedure of Example A1 is repeated, however instead of the flexo cyan ink a radiation-curable white screen ink (985-UV-1 125, provided by Ruco) is used. The ink is applied with a T 140 screen (~10 μm thickness) on the pretreated plastic film substrates and the printed samples are cured in a UV processor with a mercury lamp and an output of 200 W/cm at a belt speed of 50 m/min. The adhesive strength is determined by the tape test.

In the case of untreated samples, the ink is torn off completely, corresponding to a value 5, while with all three samples (BOPP and PE) pretreated with the photoinitiator mixture, no ink is removed, corresponding to a value 0.

Example A3

The procedure of Example A1 is repeated, but instead of the solution of IRGACURE®754 and SARTOMER®259 in isoproanol, a 1% solution of a 1:1 molecular mixture of

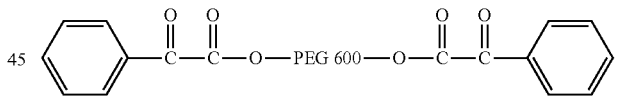

(PEG 600=ester part of polyethyleneglycol 600), the compound of example 3, and SARTOMER®259 in isopropanol is used.

The adhesive strength of the printing ink is determined by the tape test. In the case of the untreated sample, the ink is torn off completely (5), while in all three samples (BOPP and PE) pretreated with the photoinitiator mixture, no ink is removed (0).

Example A4

The procedure of example A2 is repeated, but instead of the solution of IRGACURE®754 and SARTOMER®259 in isoproanol, the photoinitiator mixture according to example A3 is used. The adhesive strength of the printing ink is determined by the tape test. In the case of the untreated sample, the ink is torn off completely (5), while in all three samples (BOPP and PE) pretreated with the photoinitiator mixture, no ink is removed (0).

Example A5

The procedure of Example A1 is repeated using a polyethylene (PE) film, but instead of the solution of IRGACURE®754 and SARTOMER®259 in isopropanol, a 1% solution of

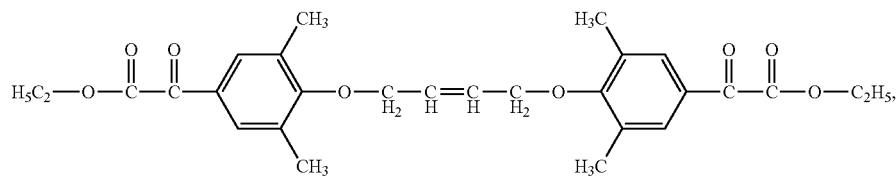

the compound of example 57, in isopropanol is applied.

The adhesive strength of the printing ink is determined by the tape test. In the case of the untreated sample, the ink is torn off considerably (4), while in the PE sample pretreated with the photoinitiator, no ink is removed (0).

Example A6

The procedure of Example A1 for the flexo cyan ink and A2 for white screen ink is repeated on all three plastic foils (two different BOPP and one PE), but instead of the solution of IRGACURE®754 and SARTOMER®259 in isopropanol, a 1% solution of

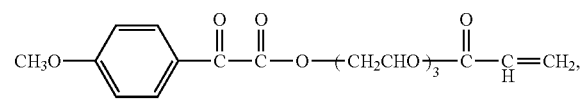

the compound of example 46, in isopropanol is applied. The adhesive strength of the printing ink is determined by the tape test. In the case of the untreated samples, the ink is torn off completely (4-5), while with all samples (BOPP and PE) pretreated with the photoinitiator (and printed either with the cyan flexo ink or the white screen ink), no ink is removed, corresponding to a value 0.

Example A7

The procedure of Example A1 (flexo cyan ink) is repeated, but instead of the solution of IRGACURE®754 and SARTOMER®259 in isopropanol, a 1% solution of

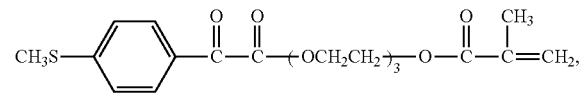

the compound of example 52, in isopropanol is applied.

The adhesive strength of the printing ink is determined by the tape test. In the case of the untreated samples, the ink is torn off completely (4-5), while with all three samples (BOPP and PE) pretreated with the photoinitiator, no ink is removed, corresponding to a value 0.

Example A8

The procedure of Example A1 (flexo cyan ink) is repeated, but instead of the solution of IRGACURE®754 and SARTOMER®259 in isopropanol, a 1% solution of

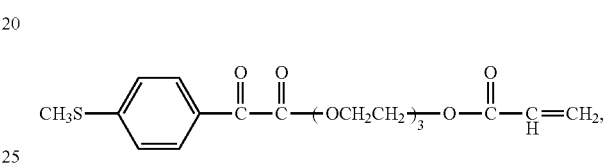

the compound of example 51, in isopropanol is applied.

The adhesive strength of the printing ink is determined by the tape test. In the case of the untreated samples, the ink is torn off completely (4-5), while with all three samples (BOPP and PE) pretreated with the photoinitiator, no ink is removed, corresponding to a value 0.

Example A9

The procedure of Example A1 (flexo cyan ink) is repeated with a bisaxial oriented polypropylene (BOPP) film, but instead of the solution of IRGACURE®754 and SARTOMER®259 in isoproanol, a 1% solution of

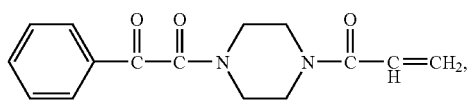

the compound of example 19, in isopropanol is applied.

The adhesive strength of the printing ink is determined by the tape test. In the case of the untreated sample, the ink is torn off completely (5), while in the BOPP sample pretreated with the photoinitiator, no ink is removed (1).

Example A10

Two different bis-axial oriented polypropylene (BOPP) films and a polyethylene (PE) film are treated with corona (ceramic electrode; 0.8 mm distance to substrate; corona discharge 1×500 W at a belt speed of 3 m/min).

A solution containing 1% of a 1:1 molecular mixture of phenylglyoxylic acid and SARTOMER®344 (polyethyleneglycole400-diacrylate from Sartomer Company) and 0.3% Synperonic T908 (surfactant from Uniqema) in water is applied to the treated side of the films using a 4 µm wire bar.

The samples are heated (50-60° C.) for a short time until the water has evaporated and the samples are dry. After drying the samples are irradiated using a UV processor with a mercury lamp with an output of 200 W/cm at a belt speed of 50 m/min.

A radiation-curable white screen ink (985-UV-1125, provided by Ruco) is used. The ink is applied with a T 140 screen (~10 μm thickness) on the pretreated plastic film substrates and the printed samples are cured under air in a UV processor with a mercury lamp with an output of 200 W/cm at a belt speed of 50 m/min.

The adhesive strength of the ink on the treated substrate is determined by the tape test. In the case of the untreated samples [i.e. only steps a) and d) are performed] the ink is torn off completely (4-5). With all three samples (BOPP and PE) according to the invention pretreated with a photoinitiator mixture [i.e. steps a) b) c) and d) are performed], no ink is removed (0).

Example A11

The procedure of Example A10 is repeated, but the photoinitiator solution is changed to a solution containing 4% of a 1:3 molecular mixture of phenylglyoxylic acid and SARTOMER®344 and 0.3% surfactant in water.

The adhesive strength of the printing ink is determined by the tape test. In the case of the untreated samples, the ink is torn off completely (4-5), while in the three samples (BOPP and PE) pretreated with the photoinitiator solution, no ink is removed (0).

Example A12

The procedure of Example A10 is repeated, but the photoinitiator solution is changed to a solution containing 4% of a 1:1 molecular mixture of phenylglyoxylic acid and SARTOMER®610 (polyethyleneglycole600-diacrylate) and 0.3% surfactant in water.

The adhesive strength of the printing ink is determined by the tape test. In the case of the untreated sample, the ink is torn off completely (4-5), while in the three samples (BOPP and PE) pretreated with the photoinitiator solution, no ink is removed (0-1).

Example A13

Two different bis-axial oriented polypropylene (BOPP) films and a polyethylene (PE) film are treated with corona (ceramic electrode; 0.8 mm distance to substrate; corona discharge 1×500 W at a belt speed of 3 m/min).

A premix with 10% of a 1:1 molecular mixture of

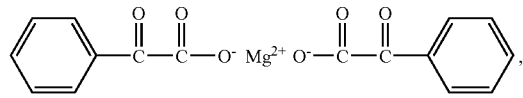

the compound of example 66 and SARTOMER®344 and 90% water is prepared. A second Mixture is prepared with 10% of the premix and 90% of isopropanol. This solution is applied to the treated side of the films using a 4 μm wire bar. The samples are stored for a short time until the isopropanol/water then has evaporated and the samples are dry. After drying the samples are irradiated using a UV processor with a mercury lamp with an output of 120 W/cm at a belt speed of 50 m/min. A radiation-curable flexo cyan ink (Gemini flexo cyan, UFG 50080-408, provided by Akzo) is applied on the pretreated plastic film substrates in a thickness of 1.5 μm with a printing machine ("Prüfbau Probedruckmaschine"). The printed samples are cured in a UV processor with a mercury lamp with an output of 120 W/cm at a belt speed of 50 m/min.

The adhesive strength of the ink on the treated substrates is determined by the tape test. In the case of the untreated samples [i.e. only steps a) and d) are performed] the ink is torn off completely (4-5). With all three samples (BOPP and PE) according to the invention pretreated with the photoinitiator mixture [i.e. steps a) b) c) and d) are performed], no ink is removed (0).

Example A14

The procedure according to Example A3 is repeated, but instead of isopropanol, water is used as solvent for the photoinitiator solution. In this case additionally 0.3% of surfactant is added to the water solution. The adhesive strength of the ink on the treated substrates is determined by the tape test. In the case of the untreated samples [i.e. only steps a) and d) are performed] the ink is torn off completely (4-5). With all three samples (BOPP and PE) according to the invention pretreated with the photoinitiator solution [i.e. steps a) b) c) and d) are performed], no ink is removed (0-1).

Example A15

The procedure according to Example A4 is repeated, but instead of isopropanol, water is used as solvent for the photoinitiator solution. In this case additionally 0.3% of surfactant is added to the water solution. The adhesive strength of the ink on the treated substrates is determined by the tape test. In the case of the untreated samples [i.e. only steps a) and d) are performed] the ink is torn off completely (4-5). With all three samples (BOPP and PE) according to the invention pretreated with the photoinitiator solution [i.e. steps a) b) c) and d) are performed], no ink is removed (0-1).

Example A15

A polyethylene film (PE) is treated with corona (ceramic electrode; 0.8 mm distance to substrate; corona discharge 1×500 W at a belt speed of 3 m/min).

A mix of a 1:1 molecular mixture of

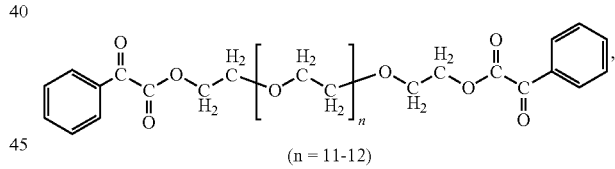

(n = 11-12)

the compound of example 3, and SARTOMER®344 is prepared and solved as a 1% solution in isopropanol. This solution is applied to the treated side of the films using a 4 μm wire bar. The samples are stored for a short time until the isopropanol has evaporated and the samples are dry. After drying the samples are treated with corona (ceramic electrode; 0.8 mm distance to substrate; corona discharge 1×500 W at a belt speed of 3 m/min).

A radiation-curable flexo cyan ink (Gemini flexo cyan, UFG 50080-408, provided by Akzo) is applied on the pretreated plastic film substrates in a thickness of 1.5 cm with a printing machine ("Prüfbau Probedruckmaschine"). The printed samples are cured in a UV processor with a mercury lamp with an output of 120 W/cm at a belt speed of 50 m/min. The adhesive strength of the ink on the treated substrates is determined by the tape test. In the case of the untreated samples [i.e. only steps a) and d) are performed] the ink is torn off completely (5). With the sample according to the invention pretreated with the photoinitiator mixture [i.e. steps a) b) c) and d) are performed], only a very small amount of ink is removed, corresponding to a value 1-2.

The invention claimed is:

1. A process for the production of a strongly adherent coating on an inorganic or organic substrate, wherein
   a) a plasma treatment, a corona discharge treatment, ozonization or ultra-violet irradiation or a flame treatment is carried out on the inorganic or organic substrate,
   b) one or more photoinitiators or mixtures of photoinitiators with monomers or/and oligomers, containing at least one ethylenically unsaturated group, or solutions, suspensions or emulsions of one or more photoinitiators or mixtures of photoinitiators with monomers or/and oligomers, containing at least one ethylenically unsaturated group, are applied to the inorganic or organic substrate to form a photoinitiator layer, and
   c) using suitable methods the photoinitiator layer is optionally dried and/or is irradiated with electromagnetic waves,
characterized in that the photoinitiators are selected from

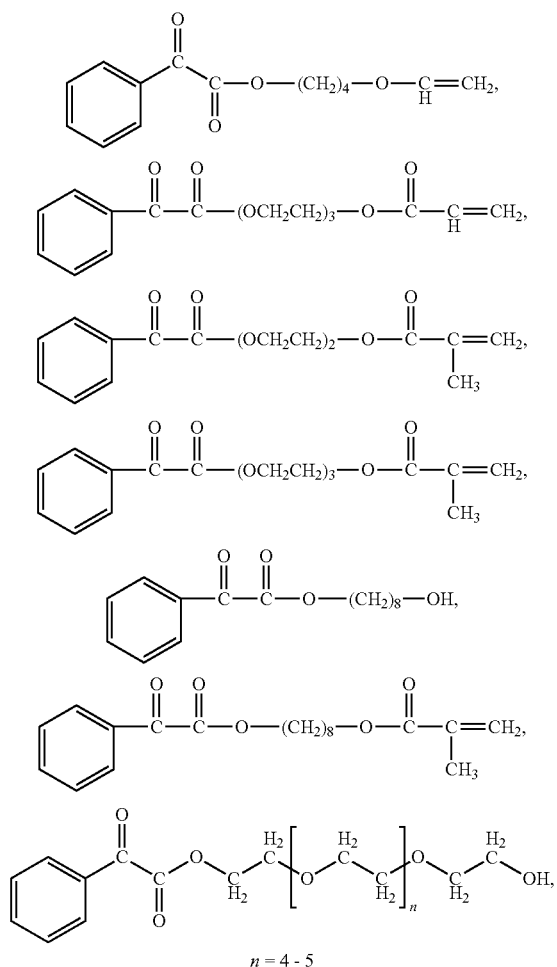

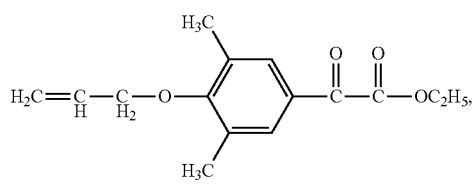

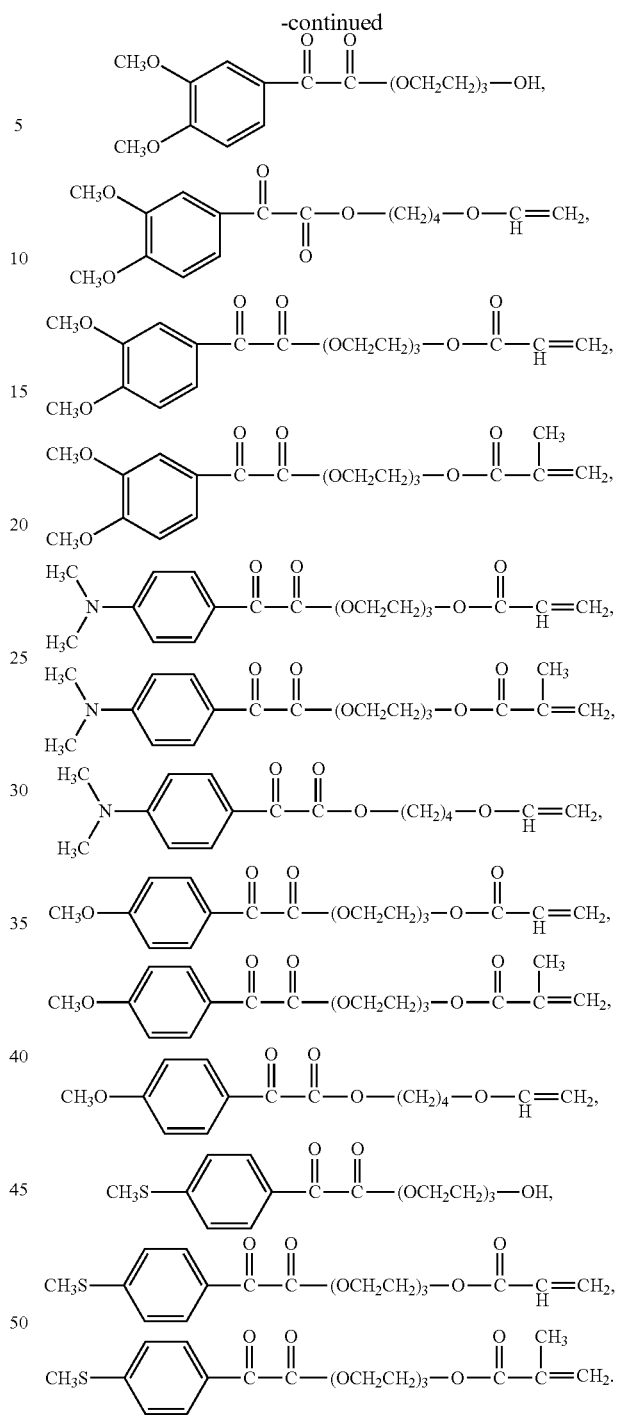

2. A process according to claim 1, wherein d) a further coating is applied and dried or cured.

3. A process according to claim 2, wherein the further coating d) is
   d1) a solvent or waterborne composition, comprising at least one polymerizable monomer, or an ethylenically unsaturated monomer or oligomer, that is cured with UV/VIS radiation or electron beam; or
   d2) a solvent or waterborne customary drying coating; or
   d3) a metal layer.

4. A process according to claim 1, wherein the photoinitiator(s) or mixtures thereof with monomers or oligomers in step b) are used in combination with one or more liquids in the form of solutions, suspensions or emulsions.

5. A process according to claim 1, wherein an inert gas or a mixture of inert gas with reactive gas is used as a gas in step a).

6. A process according to claim 1, wherein the photoinitiator layer applied in step b) has a layer thickness of up to 10 microns.

7. A process according to claim 1, wherein the photoinitiator layer applied in step b) is c) dried and/or irradiated to provide a layer with a thickness of up to 1 micron.

8. A process according to claim 1, wherein process step b) is carried out immediately after process step a) or within 24 hours after process step a).

9. A process according to claim 1, wherein the concentration of photoinitiator or photoinitiators in process step b) is from 0.0001 to 100% based on the total photoinitiator layer.

10. A process according to claim 1, wherein c) the photoinitiator layer is dried in ovens, with hot gases, heated rollers or IR or microwave radiators or by absorption.

11. A process according to claim 2, wherein c) the photoinitiator layer and/or d) the further coating is irradiated with a source that emits electromagnetic waves of wavelengths in the range from 200 nm to 700 nm, or by electron beams or by corona discharge.

12. A process according to claim 1, wherein portions of the photo-initiators, or mixtures thereof with monomers and/or oligomers, applied in process step b) that have not been crosslinked after irradiation in process step c) are removed by treatment with a solvent and/or water and/or mechanically.

13. A process according to claim 2, where the further coating is irradiated and portions of the coating are removed by treatment with a solvent and/or water and/or mechanically.

\* \* \* \* \*